(12) United States Patent
Baker, Jr. et al.

(10) Patent No.: US 9,144,606 B2
(45) Date of Patent: Sep. 29, 2015

(54) NANOEMULSION INFLUENZA VACCINE

(75) Inventors: James R. Baker, Jr., Ann Arbor, MI (US); Tarek Hamouda, Milan, MI (US); Joyce A. Sutcliffe, West Newton, MA (US)

(73) Assignee: NanoBio Corporation, Ann Arbor, MI (US)

( * ) Notice: Subject to any disclaimer, the term of this patent is extended or adjusted under 35 U.S.C. 154(b) by 998 days.

(21) Appl. No.: 12/427,517

(22) Filed: Apr. 21, 2009

(65) Prior Publication Data

US 2009/0304799 A1  Dec. 10, 2009

Related U.S. Application Data

(60) Provisional application No. 61/046,639, filed on Apr. 21, 2008, provisional application No. 61/111,319, filed on Nov. 4, 2008, provisional application No. 61/145,894, filed on Jan. 20, 2009.

(51) Int. Cl.
| | |
|---|---|
| A61K 39/145 | (2006.01) |
| C07K 14/005 | (2006.01) |
| C12N 7/00 | (2006.01) |
| A61K 9/107 | (2006.01) |
| A61K 39/00 | (2006.01) |
| A61K 39/12 | (2006.01) |

(52) U.S. Cl.
CPC .............. *A61K 39/145* (2013.01); *A61K 9/1075* (2013.01); *A61K 39/00* (2013.01); *A61K 39/12* (2013.01); *C07K 14/005* (2013.01); *C12N 7/00* (2013.01); *A61K 2039/5252* (2013.01); *A61K 2039/543* (2013.01); *A61K 2039/55566* (2013.01); *A61K 2039/58* (2013.01); *A61K 2039/70* (2013.01); *C12N 2760/16134* (2013.01); *C12N 2760/16234* (2013.01)

(58) Field of Classification Search
None
See application file for complete search history.

(56) References Cited

U.S. PATENT DOCUMENTS

| | | | |
|---|---|---|---|
| 4,826,687 A | 5/1989 | Nerome et al. | |
| 4,895,452 A | 1/1990 | Yiournas et al. | |
| 5,103,497 A | 4/1992 | Hicks | |
| 5,962,298 A | 10/1999 | Fiers et al. | |
| 6,015,832 A | 1/2000 | Baker, Jr. et al. | |
| 6,194,546 B1 | 2/2001 | Newton et al. | |
| 6,506,803 B1 | 1/2003 | Baker, Jr. et al. | |
| 6,559,189 B2 | 5/2003 | Baker, Jr. et al. | |
| 6,635,676 B2 | 10/2003 | Baker, Jr. et al. | |
| 6,861,244 B2 | 3/2005 | Barrett et al. | |
| 7,192,595 B2 | 3/2007 | Arnon et al. | |
| 7,314,624 B2 | 1/2008 | Baker et al. | |
| 2004/0043041 A1 | 3/2004 | Baker et al. | |
| 2005/0208083 A1 | 9/2005 | Annis | |
| 2006/0251684 A1 | 11/2006 | Annis et al. | |
| 2006/0257426 A1 | 11/2006 | Baker et al. | |
| 2007/0036831 A1 | 2/2007 | Baker et al. | |
| 2007/0054834 A1 | 3/2007 | Baker | |
| 2007/0116709 A1 | 5/2007 | O'Hagan et al. | |
| 2008/0254066 A1* | 10/2008 | Baker et al. ................ | 424/206.1 |

FOREIGN PATENT DOCUMENTS

| | | | |
|---|---|---|---|
| EP | 1 156 781 B1 | | 11/2001 |
| WO | WO 00/50006 | | 8/2000 |
| WO | WO 01/22992 | * | 4/2001 |
| WO | WO 2004/030608 | | 4/2004 |
| WO | WO 2005/027872 A2 | | 3/2005 |

OTHER PUBLICATIONS

Sanofi Pasteur 271/371 Fluzone® , 372 Fluzone® High-Dose, 390 Fluzone® Intradermal Seasonal Influenza vaccine FDA package insert, May 2011.*
thepharmaletter, accessed at <<http://www.thepharmaletter.com/listing/mergers-acquisitions/vaccines?tagid%5B%5D=40>> on Jan. 10, 2014.*
International Search Report for related International Patent Application No. PCT/US2009/041243 completed Sep. 25, 2009.
Written Opinion of the International Searching Authority for related International Patent Application No. PCT/US2009/041243 completed Sep. 25, 2009.
Myc et al., "Development of Immune Response that Protects Mice from Viral Pneumonitis After a Single Intranasal Immunization with Influenza a Virus and Nanoemulsion," Vaccine, vol. 21, No. 2526, pp. 3801-3814 (2003).
[Abstract] Hamouda et al., "A Novel Nanoemulsion Adjuvant Enhancing the Immune Response to beta-Propiolactone Inactivated Influenza Virus Using a Nasal Route in a Ferret Model," *Inter. Sci. Conf. On Antimicro. Agents & Chemotherapy*, vol. 48, p. 346 (2008).
Sandhu et al., "Influenza in the Older Adult, Indications for the Use of Vaccines and Antiviral Therapy," *Geriatrics*, vol. 56, pp. 223-231 (2001).
Mutsch et al., "Use of Inactivated Intranasal Influenza Vaccine and the Risk of Bell's Palsy in Switzerland," *N. Engl. J. Med.*, vol. 350, No. 9, pp. 896-903 (2004).
Bielinska et al., "A Novel, Killed-Virus Nasal Vaccinia Virus Vaccine," *Clin. Vaccine Immunol.*, 15(2): pp. 348-358 (2008).
Bielinska et al., "Mucosal Immunization with a Novel Nanoemulsion-Based Recombinant Anthrax Protective Antigen Vaccine Protects against Bacillus anthracis Spore Challenge," *Infect Immun.*, 75(8): pp. 4020-4029 (2007).
Bielinska et al., "Nasal Immunization with a Recombinant HIV gp120 and Nanoemulsion Adjuvant Produces Th1 Polarized Responses and Neutralizing Antibodies to Primary HIV Type 1 Isolates," *AIDS Research and Human Retroviruses*, 24(2): pp. 271-281 (2008).
Couch et al., "Improvement of Inactivated Influenza Virus Vaccines," *J. Infect. Dis.*, 176(Suppin. 1): pp. S38-S44 (1997).
Cox et al., "Global Epidemiology of Influenza, Past and Present," *Ann. Rev. Of Med.*, 51: pp. 407-421 (2000).
Eickhoff et al.,"Workshop summary: Aluminum in vaccines," *Vaccine*, 20(Supplet 3): pp. S1-S4 (2002).

(Continued)

*Primary Examiner* — Benjamin P Blumel
(74) *Attorney, Agent, or Firm* — Foley & Lardner LLP

(57) ABSTRACT

The present invention relates to methods for inducing an immune response to influenza in a subject comprising administering a nanoemulsion vaccine composition comprising an influenza immunogen or protein.

9 Claims, 26 Drawing Sheets

(56) References Cited

OTHER PUBLICATIONS

International Preliminary Report on Patentability cited in related International Patent Application No. PCT/US2009/041243, issued Oct. 26, 2010.

Makidon et al., "Pre-Clinical Evaluation of a Novel Nanoemulsion-Based Hepatitis B Mucosal Vaccine," *PLoS One*. 3(8): pp. 1-15 (2008).

Meyers, (Meyers, Surfactant Science and Technology, VCH Publishers Inc., New York, pp. 231-245 (1992).

Offit et al., "Addressing Parents' Concerns: Do Vaccines Contain Harmful Preservatives, Adjuvants, Additives, or Residuals?" *Pediatrics*, 112(6):pp. 1394-1401 (2003).

Reichert et al., "The Japanese Experience with Vaccinating School Children Against Influenza," *N. Engl. J. Med.*, vol. 344, pp. 889-896 (2001).

Reichert T. A., "The Japanese Program of Vaccination of School Children Against Influenza; Implications for Control of the Disease," *Semin. Pediatr. Infect. Dis.*, 13, pp. 104-111 (2002)

Schild et al., "A Single Radial Immunodiffusion Technique for the Assay of Influenza Haemagglutinin Antigen: Proposals for an Assay Method for the Haemagglutinin Content of Influenza Vaccines," *Bull. WHO*, 52, pp. 223-231 (1975).

Shoji et al., "Plant-expressed HA as a seasonal influenza vaccine candidate," Vaccine 26(23): pp. 2930-2934, (2008).

Shoji et al., "Plant-derived hemagglutinin protects ferrets against challenge infection with the A/Indonesia/05/05 strain of avian influenza," Vaccine; 27, pp. 1087-1092 (2008).

Warren et al., "Pharmacological and Toxicological Studies on Cetylpyridinium Chloride, A New Germicide," *J. Pharmacol. Exp. Ther.*, 74, pp. 401-408 (1942).

Wood et al., "An Improved Single Radial Immunodiffusion Technique for the Assay of Influenza Haemagglutinin Antigen; Application for Potency Determinators of Inactivated Whole Virus and Subunit Vaccines," *J. Biol. Stand.*, 5, pp. 237-247 (1977).

European Communication dated Mar. 10, 2014, issued in related European Patent Application No. 09 734 640.7.

\* cited by examiner

FIG. 17

Figure 19. IgA in Bronchial Aveolar Lavage Fluid at 15 Weeks

Secretory IgA was found in Bronchial Aveolar Lavage fluid from vaccinated mice

Figure 20. Serum IgG Screen Four Weeks After Prime Immunization in CD-1 Mice

Figure 21

HAI titer response in Rabbits following Immunization

A/Brisbane H1N1

HAI titer response in Rabbits following Immunization
B/Florida

Transmission Electron Micrograph of 7.5 µg Fluzone® 2008-2009 Vaccine

Three distinct structures corresponding to viral antigen particles contained in Fluzone® 2008-2009 vaccine [≈25nm (round), ≈100nm (round), and ≈100nm (crescent)].

Transmission Electron Micrograph of 7.5μg Fluzone® Mixed With 5%$W_{80}$5EC

The majority of viral antigen particles are

Transmission Electron Micrograph of 7.5µg Fluzone® Mixed With 20%$W_{80}$5EC

Viral antigen particles can be seen associated with the nanoemulsion droplets.
*Circled areas are representative of viral antigen particles

NANOEMULSION INFLUENZA VACCINE

CROSS-REFERENCE TO RELATED APPLICATIONS

This application claims benefit of U.S. Provisional Patent Application No. 61/046,639, filed on Apr. 21, 2008; U.S. Provisional Patent Application No. 61/111,319, filed on Nov. 4, 2008; and U.S. Provisional Patent Application No. 61/145,894, filed on Jan. 20, 2009. These applications are incorporated by reference in their entirety.

FIELD OF INVENTION

The present invention provides methods, compositions and kits for inducing an immune response to influenza in a subject. The methods comprise administering to a subject a nanoemulsion vaccine, wherein the nanoemulsion vaccine comprises droplets having an average diameter of less than about 1000 nm. The nanoemulsion vaccine comprises (a) an aqueous phase, (b) at least one oil, (c) at least one surfactant, (d) at least one organic solvent, and (d) at least one influenza immunogen, recombinant influenza protein, or a combination thereof. Upon administration, a human or animal subject produces a protective immune response after at least one or more than one administrations of the nanoemulsion vaccine. The present invention further provides methods and compositions for inactivating a pathogen comprising incubating the pathogen in a nanoemulsion according to the invention. The pathogen may be a bacterium, fungus, protozoa or a virus, such as influenza.

BACKGROUND OF THE INVENTION

Influenza is a serious public health threat, routinely killing hundreds of thousands of people worldwide each year, and millions during pandemics. Approximately 36,000 people die in the U.S. each year from influenza, primarily the elderly, young children and immune-compromised patients. The disease is caused by RNA viruses of the family Orthomyxoviridae, which includes three species that cause disease in vertebrates, including birds and mammals, such as humans. Of these three species, influenza A virus and influenza B virus are the most common disease agents in humans.

Influenza A virus is the pathogen associated with all known flu pandemics and is currently the most virulent form of the virus. A number of distinct serotypes have been isolated, including H1N1, H1N2, H2N2, H3N1, H3N2, H3N8, H5N1, H5N2, H5N3, H5N8, H5N9, H7N1, H7N2, H7N3, H7N4, H7N7, H9N2 and H10N7. These serotypes are classified according to two viral surface proteins, hemagglutinin (H or HA) and neuroaminidase (N or NA). Within these serotypes, isolates are further characterized by a standard nomenclature specifying virus type, geographical location where first isolated, sequential number of isolation, year of isolation, and HA and NA subtype. For instance, one such isolate is A/Wisconsin/67/2005 (H3N2).

Due to the highly variable and mutable nature of influenza antigens, developing a vaccine has proven difficult. However, no reliable treatment is available for influenza, and vaccination is the most proven method for protecting against the disease and its serious complications. The vaccine must be reformulated and readministered each year in anticipation of the serotypes of the virus predicted to be prevalent in a population each flu season, and is therefore considered a "seasonal" vaccine. Typically, the most common human vaccine is a combination of two influenza A subtypes and one influenza B strain.

Despite vigorous campaigns to promote vaccination, vaccination rates in most U.S. populations remain low, far below the U.S. government's target of 60%, with higher target percentages of high risk populations, such as the target of 90% of nursing home patients. High risk populations include the elderly, children, both juvenile and infant, pregnant women and immunocompromised patients. The U.S. Centers for Disease Control reported that only 9% to 10% children with asthma received the vaccine in 2000, and less than 10% of pregnant women. ("Prevention and Control of Influenza", Centers for Disease Control, Apr. 12, 2002.) Predictably, the rate of vaccination in less developed countries is much lower.

Presently, the most common influenza vaccines are administered by injection, these include Fluvirin®, Afluria®, FluLaval®, Fluarix®, Agrippal®, Influvac®, Mastaflu®, and Fluzone®. FluMist® is an intranasal influenza vaccine currently approved in the U.S. for use in patients between the ages of 2 and 50 years of age. For children between the ages of 2 and 8 years of age, two doses are required for vaccination, which requires two visits to a health care provider and incurs more costs. Further, no influenza vaccine is available for elderly patients that is not administered by injection. Finally, storage requirements can greatly affect both the cost and availability of influenza vaccines, as the recall of Fluvirin® in 2006 due to improper storage temperatures created shortages of the vaccine in New England.

As with most vaccines, greater immunogenicity is also sought as it correlates with greater efficacy in humans. The prior art has typically disclosed the use of recombinant proteins (e.g., U.S. Pat. Nos. 7,192,595; 6,194,546; 5,962,298), as well as the addition of adjuvants such as aluminum (U.S. Pat. No. 6,861,244) and muramyldipeptide (U.S. Pat. No. 4,826,687) to compositions to increase the immunogenicity. However, there still exists a need to develop highly effective influenza vaccines with improved storage stability and ease of administration, which are characteristics of the nanoemulsion vaccines of the present invention.

Prior teachings related to nanoemulsions are described in U.S. Pat. No. 6,015,832, which is directed to methods of inactivating Gram-positive bacteria, a bacterial spore, or Gram-negative bacteria. The methods comprise contacting the Gram-positive bacteria, bacterial spore, or Gram-negative bacteria with a bacteria-inactivating (or bacterial-spore inactivating) emulsion. U.S. Pat. No. 6,506,803 is directed to methods of killing or neutralizing microbial agents (e.g., bacterial, virus, spores, fungus, on or in humans using an emulsion. U.S. Pat. No. 6,559,189 is directed to methods for decontaminating a sample (human, animal, food, medical device, etc.) comprising contacting the sample with a nanoemulsion. The nanoemulsion, when contacted with bacteria, virus, fungi, protozoa or spores, kills or disables the pathogens. The antimicrobial nanoemulsion comprises a quaternary ammonium compound, one of ethanol/glycerol/PEG, and a surfactant. U.S. Pat. No. 6,635,676 is directed to two different compositions and methods of decontaminating samples by treating a sample with either of the compositions. Composition 1 comprises an emulsion that is antimicrobial against bacteria, virus, fungi, protozoa, and spores. The emulsions comprise an oil and a quaternary ammonium compound. U.S. Pat. No. 7,314,624 is directed to methods of inducing an immune response to an immunogen comprising treating a subject via a mucosal surface with a combination of an immunogen and a nanoemulsion. The nanoemulsion comprises oil, ethanol, a surfactant, a quaternary ammonium compound, and distilled water. US-2005-0208083-A1 and US-2006-0251684-A1 are directed to nanoemulsions having droplets with preferred sizes. US-2007-0054834-A1 is directed to compositions comprising quaternary ammonium halides and methods of using the same to treat infectious conditions. The quaternary ammonium compound may be provided as part of an emulsion. Finally, US-2007-0036831-A1 is directed to nanoemulsions comprising an anti-inflammatory agent. However, none of these references teach the methods, compositions and kits of the present invention.

In particular, U.S. Pat. No. 7,314,624 describes nanoemulsion vaccines. However, this reference does not teach the ability to induce a protective immune response to influenza with a single dose of nanoemulsion.

Thus, to increase influenza vaccination, particularly in high risk populations, there is a need for influenza vaccines that are not administered by injection for elderly patients, as well as single dose vaccines for children. The nanoemulsion composition of the present invention provides such a vaccine, which further shows improved immunogenicity and greater stability during storage.

SUMMARY OF THE INVENTION

The present invention provides methods, compositions and kits for inducing an immune response to influenza in a subject. The methods comprise administering to a subject a nanoemulsion vaccine, wherein the nanoemulsion vaccine comprises droplets having an average diameter of less than about 1000 nm. The nanoemulsion vaccine further comprises (a) an aqueous phase, (b) at least one oil, (c) at least one surfactant, (d) at least one organic solvent, (e) at least one influenza immunogen, recombinant influenza protein, and (f) optionally comprising at least one chelating agent, or any combination thereof. The human or animal subject can produce a protective immune response after at least one administration of the nanoemulsion vaccine. In one embodiment, the subject undergoes seroconversion after a single administration of the nanoemulsion vaccine. In a further embodiment, the subject is selected from adults, elderly subjects, juvenile subjects, infants, high risk subjects, pregnant women, and immunocompromised subjects. In another embodiment, the nanoemulsion vaccine may be administered intranasally.

In another embodiment of the invention, the nanoemulsion lacks an organic solvent.

The nanoemulsion vaccine adjuvant can be combined with an antigen or the nanoemulsion vaccine adjuvant can be sequentially administered with an antigen. Alternatively, or in combination, the nanoemulsion vaccine adjuvant can be administered to a subject having exposure to an antigen (i.e., prophylactic exposure, environmental exposure, etc.). Thus, in a method of the invention, the nanoemulsion vaccine adjuvant can comprise at least one influenza immunogen, recombinant influenza protein, or a combination thereof; or the nanoemulsion can be sequentially administered with one or more of such an influenza immunogen, or the subject can have been exposed to such an influenza immunogen. Furthermore, additional adjuvants may be added to the nanoemulsion vaccine.

The nanoemulsion of the present invention may be combined with one or more commercial influenza vaccines, or the nanoemulsion may be sequentially administered with one or more commercial influenza vaccines. In one embodiment of the invention, the influenza immunogen, recombinant influenza protein, or a combination thereof to be used in the nanoemulsion vaccine is present in a commercially available influenza vaccine; e.g., the nanoemulsion of the invention is used as an adjuvant for a commercially available influenza vaccine. Examples of such commercial influenza vaccines include, but are not limited to, FluMist®, Afluria®, FluLaval®, Fluarix®, Fluvirin®, Agrippal®, Influvac®, Mastaflu®, Fluzone®, any other commercially available influenza vaccine, or a combination thereof, and it may be formulated as a liquid dispersion, gel, aerosol, pulmonary aerosol, nasal aerosol ointment, cream, or solid dose. In addition, the composition may be combined with commercial vaccines for a pandemic influenza virus, such as H5N1, such as Sanofi Pasteur H5N1 vaccine, GSK H5N1 adjuvanted vaccine, Novartis H5N1 MF59 vaccine, and Sinovac H5N1 vaccine (China).

The present invention further provides methods and compositions for inactivating a pathogen comprising incubating the pathogen in a nanoemulsion according to the invention under conditions such that the pathogen is inactivated to pharmaceutical standards. The nanoemulsion comprises droplets having an average diameter of less than about 1000 nm, and (a) an aqueous phase, (b) at least one oil, (c) at least one surfactant, (d) at least one organic solvent, and (e) optionally at least one chelating agent. The pathogen may be a bacterium, protozoan, fungus or virus, such as influenza.

The foregoing general description and following brief description of the drawings and the detailed description are exemplary and explanatory and are intended to provide further explanation of the invention as claimed. Other objects, advantages, and novel features will be readily apparent to those skilled in the art from the following detailed description of the invention.

DESCRIPTION OF THE DRAWINGS

Figure 17:
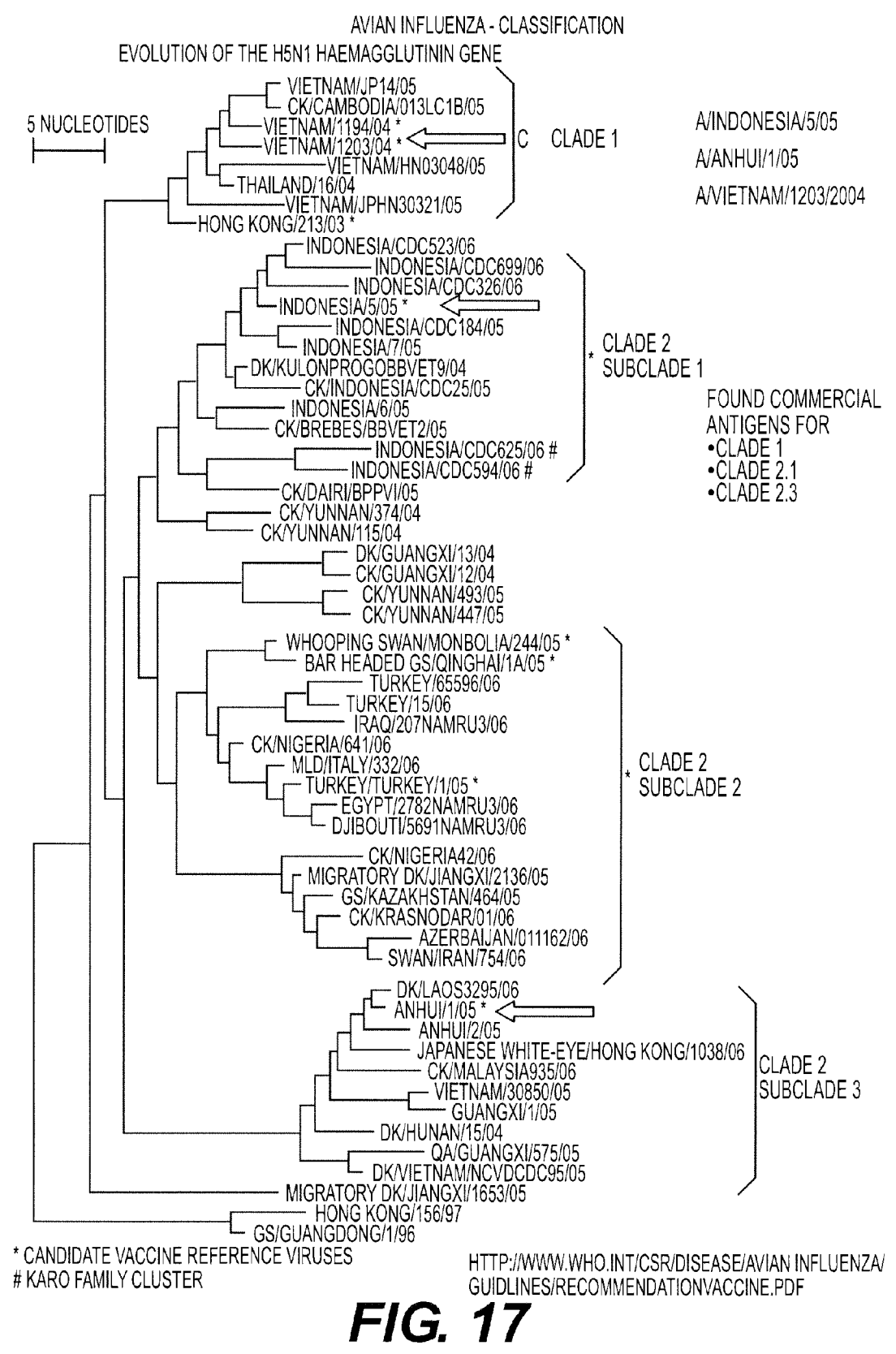

FIG. 17 shows the relationship between different clades of avian influenza virus.

FIG. 21 shows the geometric mean HAI titer response to the nanoemulsion vaccine described in Example 7 in rabbits against A/Brisbane 59 (H1N1).

DETAILED DESCRIPTION OF THE INVENTION

Figure 1:
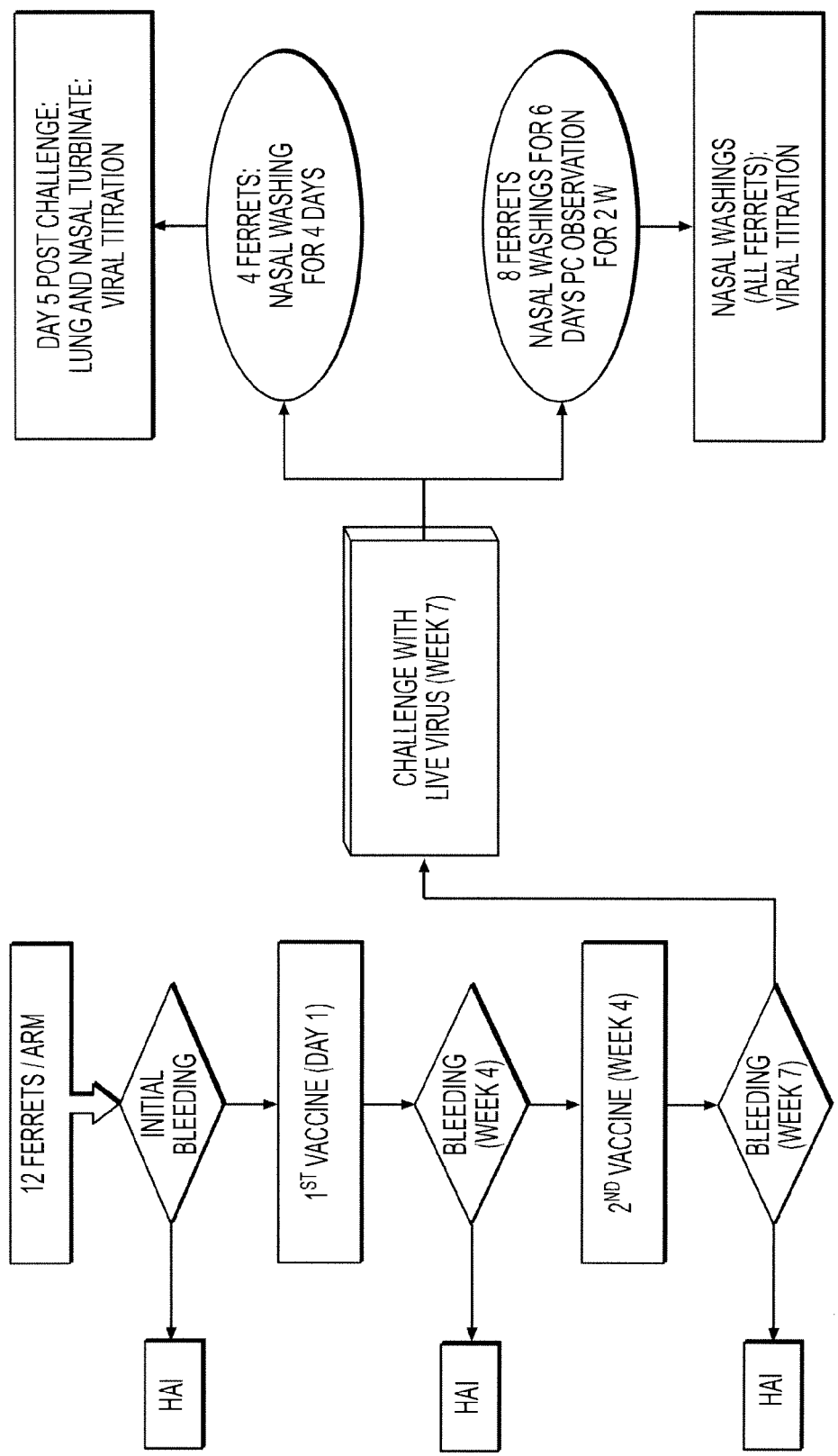
FIG. 1 shows the study design to determine the immune response in ferrets given either nanoemulsion vaccine or other vaccines.

The present invention provides methods, compositions and kits for the stimulation of an immune response to an immunogen. It has been found that nanoemulsion vaccines of the present invention can surprisingly increase the immune response of a subject to the immunogen provided therein.

The methods comprise administering to a subject a nanoemulsion vaccine, wherein the nanoemulsion vaccine comprises droplets having an average diameter of less than about 1000 nm. The nanoemulsion vaccine further comprises (a) an aqueous phase, (b) at least one oil, (c) at least one surfactant, (d) at least one organic solvent, (e) at least one influenza immunogen, recombinant influenza protein, and (f) optionally comprising at least one chelating agent, or any combination thereof. In another embodiment of the invention, the nanoemulsion lacks an organic solvent.

The human or animal subject can produce a protective immune response after at least one administration of the nanoemulsion vaccine. In one embodiment, the subject undergoes seroconversion after a single administration of the nanoemulsion vaccine. In a further embodiment, the subject is selected from adults, elderly subjects, juvenile subjects, infants, high risk subjects, pregnant women, and immunocompromised subjects. In another embodiment, the nanoemulsion vaccine may be administered intranasally.

The nanoemulsion compositions of the invention function as a vaccine adjuvant. Adjuvants serve to: (1) bring the antigen—the substance that stimulates the specific protective immune response—into contact with the immune system and influence the type of immunity produced, as well as the quality of the immune response (magnitude or duration); (2) decrease the toxicity of certain antigens; (3) reduce the amount of antigen needed for a protective response; (4) reduce the number of doses required for protection; (5) provide greater cross-reactivity and protection to heterologous influenza strains; (6) enhance immunity in poorly responding subsets of the population and/or (7) provide solubility to some vaccines components.

The nanoemulsion vaccine adjuvants are particularly useful for adjuvanting influenza vaccines.

Influenza has been established as a serious human affliction that can cause localized epidemics and global pandemics of acute respiratory infections. Each year the influenza virus is responsible for 20,000 to 40,000 deaths and up to 300,000 hospitalization cases in the U.S. (Sandhu et al., "Influenza in the Older Adult, Indications for the Use of Vaccines and Antiviral Therapy," *Geriatrics,* 56:223-231 (2001)). In the pandemic of 1918, it is widely believed that in excess of 40 million people died.

Although children and younger adults experience more cases of infection, severe illness is more common in the elderly, immunocompromised individuals, or those with chronic illnesses such as asthma, diabetes, kidney failure, and heart disease. The annual epidemics run from November to March in the Northern Hemisphere, and from April to September in the Southern Hemisphere (Cox et al., "Global Epidemiology of Influenza, Past and Present," *Ann. Rev. of Med.,* 51:407-421 (2000)).

Immunization, with current inactivated vaccines given parenterally, is effective at reducing mortality, attenuating the symptoms of the disease, and minimizing the sequelae associated with influenza. It has also been proposed that immunization of young children, identified as enhancing ongoing viral transmission in communities (Reichert T. A., "The Japanese Program of Vaccination of School Children Against Influenza; Implications for Control of the Disease," *Semin. Pediatr. Infect. Dis.,* 13:104-111 (2002); Reichert et al., "The Japanese Experience with Vaccinating School Children Against Influenza," *N. Engl. J. Med.,* 344:889-896 (2001)), might significantly reduce the spread of influenza virus in the community. Therefore, the development of an efficacious and highly tolerable vaccine, suitable for all members of a community, would be of great benefit. The majority of current vaccines have several limitations, including non-biodegradability, a depot effect, inflammation, and induration at the site of injection, and either a weak, or nocellular immune response. Attempts to increase antibody response by increasing the antigen content per dose have not always resulted in improved immunogenicity (Couch et al., "Improvement of Inactivated Influenza Virus Vaccines," *J. Infect. Dis.*, 176 (Suppln. 1): S38-S44 (1997)). Thus, the present invention, directed to nanoemulsion vaccine adjuvants providing greater efficacy and tolerability, satisfies a long felt need in the art.

Nanoemulsions are oil-in-water emulsions composed of nanometer sized droplets with surfactant(s) at the oil-water interface. Because of their size, the nanoemulsion droplets are pinocytosed by dendritic cells triggering cell maturation and efficient antigen presentation to the immune system. When mixed with different antigens, nanoemulsion adjuvants elicit and up-modulate strong humoral and cellular $T_H1$-type responses as well as mucosal immunity (Makidon et al., "Pre-Clinical Evaluation of a Novel Nanoemulsion-Based Hepatitis B Mucosal Vaccine," PLoS ONE. 3(8): 2954; 1-15 (2008); Hamouda et al., "A Novel Nanoemulsion Adjuvant Enhancing The Immune Response from Intranasal Influenza Vaccine in Mice in National Foundation for Infectious Disease," 11th Annual Conference on Vaccine Research. Baltimore, Md. (2008); Myc et al., "Development of immune response that protects mice from viral pneumonitis after a single intranasal immunization with influenza A virus and nanoemulsion," *Vaccine*, 21(25-26):3801-14 (2003); Bielinska et al., "Mucosal Immunization with a Novel Nanoemulsion-Based Recombinant Anthrax Protective Antigen Vaccine Protects against *Bacillus anthracis* Spore Challenge," *Infect Immun.*, 75(8): 4020-9 (2007); Bielinska et al., "Nasal Immunization with a Recombinant HIV gp120 and Nanoemulsion Adjuvant Produces Th1 Polarized Responses and Neutralizing Antibodies to Primary HIV Type 1 Isolates," *AIDS Research and Human Retroviruses*, 24(2): 271-81 (2008); Bielinska et al., "A Novel, Killed-Virus Nasal Vaccinia Virus Vaccine," *Clin. Vaccine Immunol.*, 15(2): 348-58 (2008); Warren et al., "Pharmacological and Toxicological Studies on Cetylpyridinium Chloride, A New Germicide," *J. Pharmacol. Exp. Ther.*, 74:401-8) (1942)). Examples of such antigens include protective antigen (PA) of anthrax (Bielinska et al., Infect. Immun., 75(8): 4020-9 (2007)), whole vaccinia virus (Bielinska et al., Clin. Vaccine Immunol., 15(2): 348-58 (2008)) or gp120 protein of Human Immune Deficiency Virus (Bielinska et al., AIDS Research and Human Retroviruses. 24(2): 271-81 (2008)). These studies demonstrate the broad application of the nanoemulsion adjuvant with a variety of antigens including recombinant proteins.

Robust immune responses to influenza have been generated in ferrets with β-propiolactone (βPL) or formaldehyde inactivated viruses and whole live viruses, which are inactivated and/or adjuvanted when mixed with the $W_{80}5EC$ nanoemulsion that has inherent antiviral activity, as well as $W_{80}5EC$-adjuvanted commercial vaccines, Fluvirin® and Fluzone®.

The nanoemulsion vaccines of the present invention may surprisingly stimulate the immune response utilizing less antigen than is required by currently used vaccines. Further, vaccines comprising the nanoemulsions of the present invention may require fewer administrations and may generate stronger responses in subjects that have typically shown weaker responses to currently used vaccines. For example, following at least one administration, the nanoemulsion vaccines may result in a greater immune response in a subject as compared to that generated by administration of a commercial influenza vaccine, influenza vaccine, or pandemic flu vaccine in the absence of a nanoemulsion.

The nanoemulsion vaccine adjuvant can be combined with an antigen or the nanoemulsion vaccine adjuvant can be sequentially administered with an antigen. Alternatively, or in combination, the nanoemulsion vaccine adjuvant can be administered to a subject having exposure to an antigen (i.e., prophylactic exposure, environmental exposure, etc.). Thus, in a method of the invention, the nanoemulsion vaccine adjuvant can comprise at least one influenza immunogen, recombinant influenza protein, or a combination thereof, or the nanoemulsion can be sequentially administered with one or more of such an influenza immunogen, or the subject can have been exposed to such an influenza immunogen. Furthermore, additional adjuvants may be added to the nanoemulsion vaccine.

The nanoemulsion of the present invention may be combined with one or more commercial influenza vaccines, such as Fluvirin® and Fluzone®, or the nanoemulsion may be sequentially administered with one or more commercial influenza vaccines. For example, the antigen can be an influenza antigen, and the nanoemulsion composition can be a vaccine to prevent, treat or ameliorate infection by influenza. The nanoemulsion vaccine comprises droplets having an average diameter of less than about 1000 nm, and the nanoemulsion vaccine comprises an aqueous phase, at least one oil, at least one surfactant or detergent, at least one organic solvent, at least one immunogen, and optionally at least one chelating agent. In one embodiment of the invention, the surfactant present in the nanoemulsion vaccine is a cationic surfactant. More than one surfactant or detergent can be present in the nanoemulsion vaccines of the invention. For example, the nanoemulsion vaccines can comprise any combination of a non-ionic, ionic, cationic, anionic, and/or zwitterionic surfactant, including two or more surfactants of the same type. The nanoemulsions of the invention can also comprise, for example, a cationic surfactant in combination with a non-ionic surfactant, or in combination with an anionic, and/or zwitterionic, and/or cationic surfactant and/or any combination thereof. In another embodiment of the invention, the nanoemulsion vaccine further comprises a chelating agent. The nanoemulsion vaccine may induce a protective immune response after at least one administration. Moreover, the immune response may be protective against one or more strains or serotypes of influenza.

The nanoemulsion vaccine can be administered to a subject which has not previously received an influenza vaccine, and the nanoemulsion vaccine can be administered to a subject who had previously received an influenza vaccine. The nanoemulsion vaccine can be given in at least a single administration annually to address seasonal influenza, pandemic flu, or a combination thereof. At least one administration of the nanoemulsion vaccine can be given to provide sustained protection, or more than one administration of the nanoemulsion vaccine can be given to provide sustained protection.

The composition can be applied using any pharmaceutically acceptable method, such as for example, intranasal, buccal, sublingual, oral, rectal, ocular, parenteral (intravenously, intradermally, intramuscularly, subcutaneously, intracisternally, intraperitoneally), pulmonary, intravaginal, locally administered, topically administered, topically administered after scarification, mucosally administered, via an aerosol, or via a buccal or nasal spray formulation. Further, the nanoemulsion vaccine can be formulated into any pharmaceutically acceptable dosage form, such as a liquid dispersion, gel, aerosol, pulmonary aerosol, nasal aerosol, ointment, cream, semi-solid dosage form, and a suspension. Further, the composition may be a controlled release formulation, sustained release formulation, immediate release formulation, or any combination thereof. Further, the composition may be a transdermal delivery system such as a patch or administered by a pressurized or pneumatic device (i.e., a "gene gun").

The present invention further comprises methods for inactivating a pathogen comprising incubating the pathogen in a nanoemulsion of the present invention. The nanoemulsion comprises droplets having an average diameter of less than about 1000 nm, and the nanoemulsion comprises an aqueous phase, at least one oil, at least one surfactant or detergent, at least one organic solvent, and optionally at least one chelating agent. In one embodiment of the invention, the surfactant present in the nanoemulsion vaccine is a cationic surfactant. More than one surfactant or detergent can be present in the nanoemulsion vaccines of the invention. The nanoemulsion vaccines for example can comprise any combination of a non-ionic, ionic, anionic, cationic, or zwitterionic surfactants, including two or more of the same type of surfactant. For example, the nanoemulsion can comprise a cationic surfactant in combination with a non-ionic surfactant or in combination with an anionic, and/or zwitterionic, and/or cationic surfactant. In another embodiment of the invention, the nanoemulsion further comprises a chelating agent.

In one embodiment of the invention, the nanoemulsion comprises droplets having an average diameter of less than about 1000 nm and: (a) an aqueous phase; (b) about 1% oil to about 80% oil; (c) about 0.1% to about 50% organic solvent; (d) about 0.001% to about 10% of a surfactant or detergent; or (e) any combination thereof. In another embodiment of the invention, the nanoemulsion vaccine comprises: (a) an aqueous phase; (b) about 1% oil to about 80% oil; (c) about 0.1% to about 50% organic solvent; (d) about 0.001% to about 10% of a surfactant or detergent; (e) at least one influenza immunogen, recombinant influenza protein, or a combination thereof, or (f) any combination thereof. In another embodiment of the invention, the nanoemulsion lacks an organic solvent.

The quantities of each component present in the nanoemulsion and/or nanoemulsion vaccine refer to a therapeutic nanoemulsion and/or nanoemulsion vaccine.

In one embodiment, the nanoemulsion vaccine can comprise about 0.001 μg to about 90 μg of each influenza antigen strain, per dose. In a further embodiment, the nanoemulsion vaccine can comprise about 15 μg or less/HA influenza strain, per dose. In another embodiment, the nanoemulsion vaccine can comprise more than one influenza immunogen.

In one embodiment, the nanoemulsion vaccine droplets have an average diameter selected from the group consisting of less than about 1000 nm, less than about 950 nm, less than about 900 nm, less than about 850 nm, less than about 800 nm, less than about 750 nm, less than about 700 nm, less than about 650 nm, less than about 600 nm, less than about 550 nm, less than about 500 nm, less than about 450 nm, less than about 400 nm, less than about 350 nm, less than about 300 nm, less than about 250 nm, less than about 200 nm, less than about 150 nm, less than about 100 nm, greater than about 50 nm, greater than about 70 nm, greater than about 125 nm, and any combination thereof.

In one embodiment, the nanoemulsion and/or nanoemulsion vaccine comprises a cationic surfactant which is cetylpyridinium chloride (CPC). CPC may have a concentration in the nanoemulsion and/or nanoemulsion vaccine of less than about 5.0% and greater than about 0.001%, or further, may have a concentration of less than about 5%, less than about 4.5%, less than about 4.0%, less than about 3.5%, less than about 3.0%, less than about 2.5%, less than about 2.0%, less than about 1.5%, less than about 1.0%, less than about 0.90%, less than about 0.80%, less than about 0.70%, less than about 0.60%, less than about 0.50%, less than about 0.40%, less than about 0.30%, less than about 0.20%, less than about 0.10%, greater than about 0.001%, greater than about 0.002%, greater than about 0.003%, greater than about 0.004%, greater than about 0.005%, greater than about 0.006%, greater than about 0.007%, greater than about 0.008%, greater than about 0.009%, and greater than about 0.010%.

In a further embodiment, the nanoemulsion and/or nanoemulsion vaccine comprising a non-ionic surfactant, such as a polysorbate surfactant, which may be polysorbate 80 or polysorbate 20, and may have a concentration of about 0.01% to about 5.0%, or about 0.1% to about 3% of polysorbate 80. The nanoemulsion vaccine may further comprise at least one preservative. In another embodiment of the invention, the nanoemulsion vaccine comprises a chelating agent.

Safety Profiles

At present, there is no U.S. FDA approved seasonal influenza vaccine that contains an adjuvant. A US FDA approved adjuvant used in various vaccines is Alum. There are three general types of aluminum-containing adjuvants: Aluminum hydroxide, Aluminum phosphate, and Potassium aluminum sulfate (often called "Alum"). The US licensed vaccines for children that contain aluminum adjuvants include diphtheria-tetanus-pertussis vaccine), and diphtheria-tetanus-acellular pertussis vaccine.

Aluminum is a very abundant element in the environment, and all infants are exposed to aluminum in the environment. Offit et al., "Addressing Parents' Concerns: Do Vaccines Contain Harmful Preservatives, Adjuvants, Additives, or Residuals?" *Pediatrics,* 112(6):1394-1401 (2003). Moreover, a relationship between high levels of aluminum exposure and neurological effects has been shown, as individuals with kidney failure—who were exposed to large quantities of aluminum when undergoing dialysis—developed serious neurological effects.

In addition to potential neurological effects, aluminum-containing vaccines have frequently resulted in local reactions such as redness, swelling and/or tenderness at the injection site. More severe local reactions such as large areas of swelling, sterile abscesses, subcutaneous (SC) nodules (small lumps under the skin some of which have inflammation in the tissue), and allergic responses are less common. Eickhoff et al., (2002). *Workshop summary: Aluminum in vaccines. Vaccine,* 20(Supplet 3):S1-S4. In contrast to aluminum-based vaccine adjuvants, the nanoemulsion vaccine adjuvants of the invention contain no components having any known adverse reactions or toxicity.

In addition, in contrast to currently known vaccine adjuvants such as Alum, the nanoemulsion vaccine adjuvants can be administered intranasally as well as intramuscularly (or subcutaneously, intravenously—i.e., any suitable method of administration can be used for vaccines comprising a nanoemulsion according to the invention). Vaccine adjuvants such as Alum can only be administered intramuscularly (IM).

Moreover, unlike many vaccine adjuvants currently in development (but not yet approved), the nanoemulsion vaccine adjuvants do not produce an inflammatory response. Inflammation caused by a vaccine adjuvant can be highly undesirable, particularly for a nasally administered vaccine.

In another embodiment of the invention, upon administration the nanoemulsion vaccine adjuvant and/or vaccine comprising a nanoemulsion vaccine adjuvant produce no inflammation correlated with the vaccine adjuvant, minimal inflammation correlated with the vaccine adjuvant, or nominal inflammation correlated with the vaccine adjuvant, where "nominal" is defined as less than a 5% increase in inflammation.

For example, concerns have been raised regarding Bell's palsy and the potential for olfactory nerve trafficking and olfactory bulb inflammation with intranasal vaccines. This concern was based upon preclinical and clinical data related to Nasalflu® (Berna Biotech Ltd), an intranasal influenza vaccine that contained a bacterial toxin adjuvant, *Escherichia coli* heat-labile toxin (LT). Reports regarding Nasalflu® found a strong association between vaccination and incidence of Bell's palsy with a 19 times higher risk versus control. "Intranasal Influenza Vaccine and the Risk of Bell's Palsy in Switzerland," *N. Engl. J. Med.,* 350:896-903 (2004). Data in mice indicated that toxins so administered could transit the cribiform plate via the olfactory nerve to reach the olfactory bulb and cause inflammation of the olfactory region of the brain.

The etiology of Bell's palsy is unclear, with a variety of associations with infectious conditions having been reported. Seventh (facial) nerve compression within the fallopian canal, which has a diameter of only 0.7 mm, can be caused by local inflammation and this is currently accepted as the most probable explanation which again can be caused by a variety of infectious or inflammatory processes. Cases of Bell's palsy have been reported following influenza virus infection and vaccination with licensed vaccines including both intranasal as well as intramuscular vaccines but no causal association has been established except in the case of NasalFlu®.

The weight of evidence, as outlined below and supported by the data that follow, suggests that there is negligible or no risk for development of Bell's palsy associated with the use of an intranasally administered nanoemulsion vaccine according to the invention as:

1. A vaccine containing a nanoemulsion vaccine adjuvant (such as NB-1008 described herein) does not contain bacterial toxins, endotoxins or cytokines that have been previously associated with Bell's palsy following intranasal delivery in humans.
2. The nanoemulsion vaccine adjuvants (such as $W_{80}5EC$-adjuvant) are composed of water (USP), an oil such as highly refined soybean oil (USP), an alcohol such as anhydrous ethanol (USP), and surfactants, such as polysorbate 80 (NF) and the cationic surfactant cetylpyridinium chloride (USP). The nanoemulsion vaccine adjuvants of the invention, such as $W_{80}5EC$-adjuvant, are inherently antimicrobial and undergo endotoxin and microbial limit testing. All the ingredients are included on the FDA list of inactive ingredients for Approved Drug Products.
3. The adjuvant or the adjuvant combined with antigen does not penetrate below the basement membrane of the nasal mucosa in mice and does not transit to the olfactory bulb.
4. The cribiform plate, olfactory bulbs, brain pituitary, trigeminal and facial nerves in rabbits after intranasal administration of a nanoemulsion vaccine were normal with no evidence of inflammation. In addition, multiple sections of cranial nerves in the cross section of the nasal turbinates appeared normal with no evidence of inflammation.

A. Definitions

The present invention is described herein using several definitions, as set forth below and throughout the application.

As used herein, "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

The term "nanoemulsion," as used herein, includes dispersions or droplets, as well as other lipid structures that can form as a result of hydrophobic forces that drive apolar residues (i.e., long hydrocarbon chains) away from water and drive polar head groups toward water, when a water immiscible oily phase is mixed with an aqueous phase. These other lipid structures include, but are not limited to, unilamellar, paucilamellar, and multilamellar lipid vesicles, micelles, and lamellar phases.

The term "subject" as used herein refers to organisms to be treated by the compositions of the present invention. Such organisms include animals (domesticated animal species, wild animals), and humans.

The term "surfactant" refers to any molecule having both a polar head group, which energetically prefers solvation by water, and a hydrophobic tail which is not well solvated by water. The term "cationic surfactant" refers to a surfactant with a cationic head group. The term "anionic surfactant" refers to a surfactant with an anionic head group. The term "non-ionic surfactant: refers to a surfactant with uncharged head groups. The term "zwitterioninc surfactant refers to a surfactant with both cationic and anionic head groups.

The terms "Hydrophile-Lipophile Balance Index Number" and "HLB Index Number" refer to an index for correlating the chemical structure of surfactant molecules with their surface activity. The HLB Index Number may be calculated by a variety of empirical formulas as described by Meyers, (Meyers, Surfactant Science and Technology, VCH Publishers Inc., New York, pp. 231-245 [1992]), incorporated herein by reference. As used herein, the HLB Index Number of a surfactant is the HLB Index Number assigned to that surfactant in McCutcheon's Volume 1: Emulsifiers and Detergents North American Edition, 1996 (incorporated herein by reference). The HLB Index Number ranges from 0 to about 70 or more for commercial surfactants. Hydrophilic surfactants with high solubility in water and solubilizing properties are at the high end of the scale, while surfactants with low solubility in water which are good solubilizers of water in oils are at the low end of the scale.

The terms "buffer" or "buffering agents" refer to materials which when added to a solution, cause the solution to resist changes in pH.

The terms "chelator" or "chelating agent" refer to any materials having more than one atom with a lone pair of electrons that are available to bond to a metal ion.

The terms "pharmaceutically acceptable" or "pharmacologically acceptable," as used herein, refer to compositions that do not substantially produce adverse allergic or adverse immunological reactions when administered to a host (e.g., an animal or a human). Such formulations include any pharmaceutically acceptable dosage form. Examples of such pharmaceutically acceptable dosage forms include, but are not limited to, dips, sprays, seed dressings, stem injections, lyophilized dosage forms, sprays, and mists. As used herein, "pharmaceutically acceptable carrier" includes any and all solvents, dispersion media, coatings, wetting agents (e.g., sodium lauryl sulfate), isotonic and absorption delaying agents, disintegrants (e.g., potato starch or sodium starch glycolate), and the like.

As used herein, the term "intranasal(ly)" refers to application of the compositions of the present invention to the surface of the skin and mucosal cells and tissues of the nasal passages, e.g., nasal mucosa, sinus cavity, nasal turbinates, or other tissues and cells which line the nasal passages.

As used herein, the term "topical(ly)" refers to application of the compositions of the present invention to the surface of the skin and mucosal cells and tissues (e.g., buccal, lingual, sublingual, masticatory, respiratory or nasal mucosa, nasal turbinates and other tissues and cells which line hollow organs or body cavities).

As used herein, the term "topically active agents" refers to compositions of the present invention that are applied to skin or mucosal surfaces.

As used herein, the term "systemically active drugs" is used broadly to indicate a substance or composition whose administration is not necessarily near the infection source and whose levels can be measured at sites quite distant from the site of administration (e.g., oral drug administration where levels of the drug are found in the bloodstream or in tissues or organs).

B. Properties of the Nanoemulsion Vaccines of the Invention

The nanoemulsions and/or nanoemulsion vaccines of the present invention, upon pharmaceutically acceptable administration, are capable of stimulating an immune response to an immunogen. The immunogen may be any bacterial, protozoan, viral or fungal antigen, and is typically administered in the composition comprising the nanoemulsion vaccine. In one embodiment, the immunogen can be an influenza immunogen or any subcomponent/fragment of the immunogen. In one embodiment, the antigen is a recombinant antigen. Methods of making recombinant antigens are well known in the art. An example of one method of making recombinant antigens is described by Shoji et al., "Plant-expressed HA as a seasonal influenza vaccine candidate," *Vaccine* 26(23): 2930-2934, 2008.

The nanoemulsion vaccine effectively prevents, treats or ameliorates infection of a subject by a pathogen comprising the immunogen. The nanoemulsion vaccine induces a protective immune response in a subject upon administration, following at least one administration. The nanoemulsion and/or nanoemulsion vaccine is not systemically toxic to a subject.

C. Stability of the Nanoemulsion Vaccines of the Invention

The nanoemulsions and/or nanoemulsion vaccines of the invention can be stable at about 40° C. and about 75% relative humidity for a time period of at least up to about 2 days, at least up to about 2 weeks, at least up to about 1 month, at least up to about 3 months, at least up to about 6 months, at least up to about 12 months, at least up to about 18 months, at least up to about 2 years, at least up to about 2.5 years, or at least up to about 3 years.

In another embodiment of the invention, the nanoemulsions and/or nanoemulsion vaccines of the invention can be stable at about 25° C. and about 60% relative humidity for a time period of at least up least up to about 2 days, at least up to about 2 weeks, to about 1 month, at least up to about 3 months, at least up to about 6 months, at least up to about 12 months, at least up to about 18 months, at least up to about 2 years, at least up to about 2.5 years, or at least up to about 3 years, at least up to about 3.5 years, at least up to about 4 years, at least up to about 4.5 years, or at least up to about 5 years.

Further, the nanoemulsions and/or nanoemulsion vaccines of the invention can be stable at about 4° C. for a time period of at least up to about 1 month, at least up to about 3 months, at least up to about 6 months, at least up to about 12 months, at least up to about 18 months, at least up to about 2 years, at least up to about 2.5 years, at least up to about 3 years, at least up to about 3.5 years, at least up to about 4 years, at least up to about 4.5 years, at least up to about 5 years, at least up to about 5.5 years, at least up to about 6 years, at least up to about 6.5 years, or at least up to about 7 years.

The nanoemulsions and/or nanoemulsion vaccines of the invention can be stable at about −20° C. for a time period of at least up to about 1 month, at least up to about 3 months, at least up to about 6 months, at least up to about 12 months, at least up to about 18 months, at least up to about 2 years, at least up to about 2.5 years, at least up to about 3 years, at least up to about 3.5 years, at least up to about 4 years, at least up to about 4.5 years, at least up to about 5 years, at least up to about 5.5 years, at least up to about 6 years, at least up to about 6.5 years, or at least up to about 7 years.

These stability parameters are also applicable to nanoemulsion adjuvants and/or nanoemulsion vaccines.

D. Pathogens

Any immunogen from any pathogen may be used with the methods of the present invention. As the nanoemulsions and/or nanoemulsion vaccines may increase the immunogenecity of any immunogen, the methods are not limited to any particular immunogen or pathogen. For example, an immunogen from a bacteria, virus, protozoa or fungus may be used. The immunogen may be a part of the pathogen or the whole pathogen. For example, the immunogen may be a peptide, a glycoprotein, or an entire organism. The immunogen may be native or recombinant, mutated and/or may comprise heterologous elements, such as a fusion polypeptide, to increase immunogenicity or aid in purification or formulation. Any immunogen known in the art may be used with the nanoemulsions of the present invention, and a person of skill in the art would readily ascertain suitable immunogens.

In one embodiment, an immunogen from influenza virus may be used, including, but not limited to immunogens from influenza A virus, influenza B virus or influenza C virus. More specifically, the influenza pathogen may be, for example, one or more of:

(1) inactivated influenza virus, a recombinant immunogenic variant of an inactivated influenza virus, or an immunogenic fragment of an inactivated influenza virus;

(2) H5N1, a recombinant immunogenic variant of H5N1, or an immunogenic fragment of H5N1;

(3) H1N1, a recombinant immunogenic variant of H1N1, or an immunogenic fragment of H1N1;

(4) H1N2, a recombinant immunogenic variant of H1N2, or an immunogenic fragment of H1N2;

(5) H3N2, a recombinant immunogenic variant of H3N2, or an immunogenic fragment of H3N2;

(6) H2N2, a recombinant immunogenic variant of H2N2, or an immunogenic fragment of H2N2;

(7) H7N7, a recombinant immunogenic variant of H7N7, or an immunogenic fragment of H7N7;

(8) H9N2, a recombinant immunogenic variant of H9N2, or an immunogenic fragment of H9N2;

(9) H7N2, a recombinant immunogenic variant of H7N2, or an immunogenic fragment of H7N2;

(10) H7N3, a recombinant immunogenic variant of H7N3, or an immunogenic fragment of H7N3;

(11) H10N7, a recombinant immunogenic variant of H10N7, or an immunogenic fragment of H10N7;

(12) H1, a recombinant immunogenic variant of H1, or an immunogenic fragment of H1;

(13) H2, a recombinant immunogenic variant of H2, or an immunogenic fragment of H2;

(14) H3, a recombinant immunogenic variant of H3, or an immunogenic fragment of H3;

(15) H5, a recombinant immunogenic variant of H5, or an immunogenic fragment of H5;

(16) H7, a recombinant immunogenic variant of H7, or an immunogenic fragment of H7;

(17) H9, a recombinant immunogenic variant of H9, or an immunogenic fragment of H9;

(18) N1, a recombinant immunogenic variant of N1, or an immunogenic fragment of N1;
(19) N2, a recombinant immunogenic variant of N2, or an immunogenic fragment of N2;
(20) N3, a recombinant immunogenic variant of N3, or an immunogenic fragment of N3;
(21) N7, a recombinant immunogenic variant of N7, or an immunogenic fragment of N7;
(22) a seasonal influenza strain, a recombinant immunogenic variant of a seasonal influenza strain, or an immunogenic fragment of a seasonal influenza strain;
(23) a pandemic influenza strain, a recombinant immunogenic variant of a pandemic influenza strain, or an immunogenic fragment of a pandemic influenza strain;
(24) an influenza A virus strain, a recombinant immunogenic variant of an influenza A virus strain, or an immunogenic fragment of an influenza A virus strain;
(25) an influenza B virus strain, a recombinant immunogenic variant of an influenza B virus strain, or an immunogenic fragment of an influenza B virus strain;
(26) an influenza C virus strain, a recombinant immunogenic variant of an influenza C virus strain, or an immunogenic fragment of an influenza C virus strain;
(27) A/New Caledonia/20/99 lineage;
(28) A/Fujian/411/2002 lineage;
(29) A/Kumamoto/102/2002 lineage;
(30) A/Wyoming/3/2003 lineage;
(31) A/Wellington/1/2004 lineage;
(32) A/California/7/2004 lineage;
(33) A/New York/55/2004 lineage;
(34) A/Solomon Islands/3/2006 lineage;
(35) A/Wisconsin/67/2005 lineage;
(36) A/Hiroshima/52/2005 lineage;
(37) A/Brisbane/1 0/2007 lineage;
(38) B/Hong Kong/330/2001 lineage;
(39) B/Shandong/7/97 lineage;
(40) B/Hong Kong/1434/2002 lineage;
(41) B/Brisbane/32/2002 lineage;
(42) B/Shanghai/361/2002 lineage;
(43) B/Jiangsu/10/2003 lineage;
(44) B/Jilin/20/2003 lineage;
(45) B/Malaysia/2506/2004 lineage;
(46) B/Florida/4/2006 lineage,
(47) B/Victoria/2/87 lineage,
(48) B/Yamagata/16/88 lineage,
(49) C/Aichi/1/99 lineage,
(50) C/Sao Paulo/378/82 lineage,
(51) C/Yamagata/26/81 lineage,
(52) C/Aichi/1/81 lineage,
(53) C/Aomori/74 lineage,
(54) C/Mississippi/80 lineage,
(55) any new strain or subtype that may arise due to antigenic drift and/or mutation; or
(56) any combination thereof.

E. Immune Response

The immune response of the subject can be measured by determining the titer and/or presence of antibodies against the immunogen after administration of the nanoemulsion vaccine to evaluate the humoral response to the immunogen. Seroconversion refers to the development of specific antibodies to an immunogen and may be used to evaluate the presence of a protective immune response. Such antibody-based detection is often measured using Western blotting or enzyme-linked immunosorbent (ELISA) assays or hemagglutination inhibition assays (HAI). Persons of skill in the art would readily select and use appropriate detection methods.

Another method for determining the subject's immune response is to determine the cellular immune response, such as through immunogen-specific cell responses, such as cytotoxic T lymphocytes, or immunogen-specific lymphocyte proliferation assay. Additionally, challenge by the pathogen may be used to determine the immune response, either in the subject, or, more likely, in an animal model. A person of skill in the art would be well versed in the methods of determining the immune response of a subject and the invention is not limited to any particular method.

F. Nanoemulsion Vaccines

The term "nanoemulsion", as defined herein, refers to a dispersion or droplet or any other lipid structure. Typical lipid structures contemplated in the invention include, but are not limited to, unilamellar, paucilamellar and multilamellar lipid vesicles, micelles and lamellar phases.

The nanoemulsion and/or nanoemulsion vaccine of the present invention comprises droplets having an average diameter size, less than about 1,000 nm, less than about 950 nm, less than about 900 nm, less than about 850 nm, less than about 800 nm, less than about 750 nm, less than about 700 nm, less than about 650 nm, less than about 600 nm, less than about 550 nm, less than about 500 nm, less than about 450 nm, less than about 400 nm, less than about 350 nm, less than about 300 nm, less than about 250 nm, less than about 200 nm, less than about 150 nm, or any combination thereof. In one embodiment, the droplets have an average diameter size greater than about 125 nm and less than or equal to about 600 nm. In a different embodiment, the droplets have an average diameter size greater than about 50 nm or greater than about 70 nm, and less than or equal to about 125 nm.

1. Aqueous Phase

The aqueous phase can comprise any type of aqueous phase including, but not limited to, water (e.g., $H_2O$, distilled water, purified water, water for injection, de-ionized water, tap water) and solutions (e.g., phosphate buffered saline (PBS) solution). In certain embodiments, the aqueous phase comprises water at a pH of about 4 to 10, preferably about 6 to 8. The water can be deionized (hereinafter "$DiH_2O$"). In some embodiments the aqueous phase comprises phosphate buffered saline (PBS). The aqueous phase may further be sterile and pyrogen free.

2. Organic Solvents

Organic solvents in the nanoemulsion vaccines of the invention include, but are not limited to, $C_1$-$C_{12}$ alcohol, diol, triol, dialkyl phosphate, tri-alkyl phosphate, such as tri-n-butyl phosphate, semi-synthetic derivatives thereof, and combinations thereof. In one aspect of the invention, the organic solvent is an alcohol chosen from a nonpolar solvent, a polar solvent, a protic solvent, or an aprotic solvent.

Suitable organic solvents for the nanoemulsion vaccine include, but are not limited to, ethanol, methanol, isopropyl alcohol, glycerol, medium chain triglycerides, diethyl ether, ethyl acetate, acetone, dimethyl sulfoxide (DMSO), acetic acid, n-butanol, butylene glycol, perfumers alcohols, isopropanol, n-propanol, formic acid, propylene glycols, glycerol, sorbitol, industrial methylated spirit, triacetin, hexane, benzene, toluene, diethyl ether, chloroform, 1,4-dixoane, tetrahydrofuran, dichloromethane, acetone, acetonitrile, dimethylformamide, dimethyl sulfoxide, formic acid, semi-synthetic derivatives thereof, and any combination thereof.

3. Oil Phase

The oil in the nanoemulsion vaccine of the invention can be any cosmetically or pharmaceutically acceptable oil. The oil can be volatile or non-volatile, and may be chosen from animal oil, vegetable oil, natural oil, synthetic oil, hydrocarbon oils, silicone oils, semi-synthetic derivatives thereof, and combinations thereof.

Suitable oils include, but are not limited to, mineral oil, squalene oil, flavor oils, silicon oil, essential oils, water insoluble vitamins, Isopropyl stearate, Butyl stearate, Octyl palmitate, Cetyl palmitate, Tridecyl behenate, Diisopropyl adipate, Dioctyl sebacate, Menthyl anthranhilate, Cetyl octanoate, Octyl salicylate, Isopropyl myristate, neopentyl glycol dicarpate cetols, Ceraphyls®, Decyl oleate, diisopropyl adipate, $C_{12-15}$ alkyl lactates, Cetyl lactate, Lauryl lactate, Isostearyl neopentanoate, Myristyl lactate, Isocetyl stearoyl stearate, Octyldodecyl stearoyl stearate, Hydrocarbon oils, Isoparaffin, Fluid paraffins, Isododecane, Petrolatum, Argan oil, Canola oil, Chile oil, Coconut oil, corn oil, Cottonseed oil, Flaxseed oil, Grape seed oil, Mustard oil, Olive oil, Palm oil, Palm kernel oil, Peanut oil, Pine seed oil, Poppy seed oil, Pumpkin seed oil, Rice bran oil, Safflower oil, Tea oil, Truffle oil, Vegetable oil, Apricot (kernel) oil, Jojoba oil (simmondsia chinensis seed oil), Grapeseed oil, Macadamia oil, Wheat germ oil, Almond oil, Rapeseed oil, Gourd oil, Soybean oil, Sesame oil, Hazelnut oil, Maize oil, Sunflower oil, Hemp oil, Bois oil, Kuki nut oil, Avocado oil, Walnut oil, Fish oil, berry oil, allspice oil, juniper oil, seed oil, almond seed oil, anise seed oil, celery seed oil, cumin seed oil, nutmeg seed oil, leaf oil, basil leaf oil, bay leaf oil, cinnamon leaf oil, common sage leaf oil, eucalyptus leaf oil, lemon grass leaf oil, melaleuca leaf oil, oregano leaf oil, patchouli leaf oil, peppermint leaf oil, pine needle oil, rosemary leaf oil, spearmint leaf oil, tea tree leaf oil, thyme leaf oil, wintergreen leaf oil, flower oil, chamomile oil, clary sage oil, clove oil, geranium flower oil, hyssop flower oil, jasmine flower oil, lavender flower oil, manuka flower oil, Marhoram flower oil, orange flower oil, rose flower oil, ylang-ylang flower oil, Bark oil, cassia Bark oil, cinnamon bark oil, sassafras Bark oil, Wood oil, camphor wood oil, cedar wood oil, rosewood oil, sandalwood oil), rhizome (ginger) wood oil, resin oil, frankincense oil, myrrh oil, peel oil, bergamot peel oil, grapefruit peel oil, lemon peel oil, lime peel oil, orange peel oil, tangerine peel oil, root oil, valerian oil, Oleic acid, Linoleic acid, Oleyl alcohol, Isostearyl alcohol, semi-synthetic derivatives thereof, and any combinations thereof.

The oil may further comprise a silicone component, such as a volatile silicone component, which can be the sole oil in the silicone component or can be combined with other silicone and non-silicone, volatile and non-volatile oils. Suitable silicone components include, but are not limited to, methylphenylpolysiloxane, simethicone, dimethicone, phenyltrimethicone (or an organomodified version thereof), alkylated derivatives of polymeric silicones, cetyl dimethicone, lauryl trimethicone, hydroxylated derivatives of polymeric silicones, such as dimethiconol, volatile silicone oils, cyclic and linear silicones, cyclomethicone, derivatives of cyclomethicone, hexamethylcyclotrisiloxane, octamethylcyclotetrasiloxane, decamethylcyclopentasiloxane, volatile linear dimethylpolysiloxanes, isohexadecane, isoeicosane, isotetracosane, polyisobutene, isooctane, isododecane, semi-synthetic derivatives thereof, and combinations thereof.

The volatile oil can be the organic solvent, or the volatile oil can be present in addition to an organic solvent. Suitable volatile oils include, but are not limited to, a terpene, monoterpene, sesquiterpene, carminative, azulene, menthol, camphor, thujone, thymol, nerol, linalool, limonene, geraniol, perillyl alcohol, nerolidol, famesol, ylangene, bisabolol, farnesene, ascaridole, chenopodium oil, citronellal, citral, citronellol, chamazulene, yarrow, guaiazulene, chamomile, semi-synthetic derivatives, or combinations thereof.

In one aspect of the invention, the volatile oil in the silicone component is different than the oil in the oil phase.

4. Surfactants

The surfactant in the nanoemulsion vaccine of the invention can be a pharmaceutically acceptable ionic surfactant, a pharmaceutically acceptable nonionic surfactant, a pharmaceutically acceptable cationic surfactant, a pharmaceutically acceptable anionic surfactant, or a pharmaceutically acceptable zwitterionic surfactant.

Exemplary useful surfactants are described in Applied Surfactants: Principles and Applications. Tharwat F. Tadros, Copyright 8 2005 WILEY-VCH Verlag GmbH & Co. KGaA, Weinheim ISBN: 3-527-30629-3), which is specifically incorporated by reference.

Further, the surfactant can be a pharmaceutically acceptable ionic polymeric surfactant, a pharmaceutically acceptable nonionic polymeric surfactant, a pharmaceutically acceptable cationic polymeric surfactant, a pharmaceutically acceptable anionic polymeric surfactant, or a pharmaceutically acceptable zwitterionic polymeric surfactant. Examples of polymeric surfactants include, but are not limited to, a graft copolymer of a poly(methyl methacrylate) backbone with multiple (at least one) polyethylene oxide (PEO) side chain, polyhydroxystearic acid, an alkoxylated alkyl phenol formaldehyde condensate, a polyalkylene glycol modified polyester with fatty acid hydrophobes, a polyester, semi-synthetic derivatives thereof, or combinations thereof.

Surface active agents or surfactants, are amphipathic molecules that consist of a non-polar hydrophobic portion, usually a straight or branched hydrocarbon or fluorocarbon chain containing 8-18 carbon atoms, attached to a polar or ionic hydrophilic portion. The hydrophilic portion can be nonionic, ionic or zwitterionic. The hydrocarbon chain interacts weakly with the water molecules in an aqueous environment, whereas the polar or ionic head group interacts strongly with water molecules via dipole or ion-dipole interactions. Based on the nature of the hydrophilic group, surfactants are classified into anionic, cationic, zwitterionic, nonionic and polymeric surfactants.

Suitable surfactants include, but are not limited to, ethoxylated nonylphenol comprising 9 to 10 units of ethyleneglycol, ethoxylated undecanol comprising 8 units of ethyleneglycol, polyoxyethylene (20) sorbitan monolaurate, polyoxyethylene (20) sorbitan monopalmitate, polyoxyethylene (20) sorbitan monostearate, polyoxyethylene (20) sorbitan monooleate, sorbitan monolaurate, sorbitan monopalmitate, sorbitan monostearate, sorbitan monooleate, ethoxylated hydrogenated ricin oils, sodium laurylsulfate, a diblock copolymer of ethyleneoxyde and propyleneoxyde, Ethylene Oxide-Propylene Oxide Block Copolymers, and tetra-functional block copolymers based on ethylene oxide and propylene oxide, Glyceryl monoesters, Glyceryl caprate, Glyceryl caprylate, Glyceryl cocate, Glyceryl erucate, Glyceryl hydroxysterate, Glyceryl isostearate, Glyceryl lanolate, Glyceryl laurate, Glyceryl linolate, Glyceryl myristate, Glyceryl oleate, Glyceryl PABA, Glyceryl palmitate, Glyceryl ricinoleate, Glyceryl stearate, Glyceryl thiglycolate, Glyceryl dilaurate, Glyceryl dioleate, Glyceryl dimyristate, Glyceryl disterate, Glyceryl sesuioleate, Glyceryl stearate lactate, Polyoxyethylene cetyl/stearyl ether, Polyoxyethylene cholesterol ether, Polyoxyethylene laurate or dilaurate, Polyoxyethylene stearate or distearate, polyoxyethylene fatty ethers, Polyoxyethylene lauryl ether, Polyoxyethylene stearyl ether, polyoxyethylene myristyl ether, a steroid, Cholesterol, Beta-sitosterol, Bisabolol, fatty acid esters of alcohols, isopropyl myristate, Aliphati-isopropyl n-butyrate, Isopropyl n-hexanoate, Isopropyl n-decanoate, Isproppyl palmitate, Octyldodecyl myristate, alkoxylated alcohols, alkoxylated acids, alkoxylated amides, alkoxylated sugar derivatives, alkoxylated derivatives of natural oils and waxes, polyoxyethylene polyoxypropylene block copolymers, nonoxynol-14, PEG-8 laurate, PEG-6 Cocoamide, PEG-20 methylglucose sesquistearate, PEG40 lanolin, PEG-40 castor oil, PEG-40 hydrogenated castor oil, polyoxyethylene fatty ethers, glyceryl diesters, polyoxyethylene stearyl ether, polyoxyethylene myristyl ether, and polyoxyethylene lauryl ether, glyceryl dilaurate, glyceryl dimystate, glyceryl distearate, semi-synthetic derivatives thereof, or mixtures thereof.

Additional suitable surfactants include, but are not limited to, non-ionic lipids, such as glyceryl laurate, glyceryl myristate, glyceryl dilaurate, glyceryl dimyristate, semi-synthetic derivatives thereof, and mixtures thereof.

In additional embodiments, the surfactant is a polyoxyethylene fatty ether having a polyoxyethylene head group ranging from about 2 to about 100 groups, or an alkoxylated alcohol having the structure $R_5$—(OCH$_2$ CH$_2$)$_y$—OH, wherein $R_5$ is a branched or unbranched alkyl group having from about 6 to about 22 carbon atoms and y is between about 4 and about 100, and preferably, between about 10 and about 100. Preferably, the alkoxylated alcohol is the species wherein $R_5$ is a lauryl group and y has an average value of 23.

In a different embodiment, the surfactant is an alkoxylated alcohol which is an ethoxylated derivative of lanolin alcohol. Preferably, the ethoxylated derivative of lanolin alcohol is laneth-10, which is the polyethylene glycol ether of lanolin alcohol with an average ethoxylation value of 10.

Nonionic surfactants include, but are not limited to, an ethoxylated surfactant, an alcohol ethoxylated, an alkyl phenol ethoxylated, a fatty acid ethoxylated, a monoalkaolamide ethoxylated, a sorbitan ester ethoxylated, a fatty amino ethoxylated, an ethylene oxide-propylene oxide copolymer, Bis(polyethylene glycol bis[imidazoyl carbonyl]), nonoxynol-9, Bis(polyethylene glycol bis[imidazoyl carbonyl]), Brij® 35, Brij® 56, Brij® 72, Brij® 76, Brij® 92V, Brij® 97, Brij® 58P, Cremophor® EL, Decaethylene glycol monododecyl ether, N-Decanoyl-N-methylglucamine, n-Decyl alpha-D-glucopyranoside, Decyl beta-D-maltopyranoside, n-Dodecanoyl-N-methylglucamide, n-Dodecyl alpha-D-maltoside, n-Dodecyl beta-D-maltoside, n-Dodecyl beta-D-maltoside, Heptaethylene glycol monodecyl ether, Heptaethylene glycol monododecyl ether, Heptaethylene glycol monotetradecyl ether, n-Hexadecyl beta-D-maltoside, Hexaethylene glycol monododecyl ether, Hexaethylene glycol monohexadecyl ether, Hexaethylene glycol monooctadecyl ether, Hexaethylene glycol monotetradecyl ether, Igepal CA-630, Igepal CA-630, Methyl-6-O-(N-heptylcarbamoyl)-alpha-D-glucopyranoside, Nonaethylene glycol monododecyl ether, N-Nonanoyl-N-methylglucamine, N-Nonanoyl-N-methylglucamine, Octaethylene glycol monodecyl ether, Octaethylene glycol monododecyl ether, Octaethylene glycol monohexadecyl ether, Octaethylene glycol monooctadecyl ether, Octaethylene glycol monotetradecyl ether, Octyl-beta-D-glucopyranoside, Pentaethylene glycol monodecyl ether, Pentaethylene glycol monododecyl ether, Pentaethylene glycol monohexadecyl ether, Pentaethylene glycol monohexyl ether, Pentaethylene glycol monooctadecyl ether, Pentaethylene glycol monooctyl ether, Polyethylene glycol diglycidyl ether, Polyethylene glycol ether W-1, Polyoxyethylene 10 tridecyl ether, Polyoxyethylene 100 stearate, Polyoxyethylene 20 isohexadecyl ether, Polyoxyethylene 20 oleyl ether, Polyoxyethylene 40 stearate, Polyoxyethylene 50 stearate, Polyoxyethylene 8 stearate, Polyoxyethylene bis(imidazolyl carbonyl), Polyoxyethylene 25 propylene glycol stearate, Saponin from Quillaja bark, Span® 20, Span® 40, Span® 60, Span® 65, Span® 80, Span® 85, Tergitol, Type 15-S-12, Tergitol, Type 15-S-30, Tergitol, Type 15-S-5, Tergitol, Type 15-S-7, Tergitol, Type 15-S-9, Tergitol, Type NP-10, Tergitol, Type NP-4, Tergitol, Type NP-40, Tergitol, Type NP-7, Tergitol, Type NP-9, Tergitol, Tergitol, Type TMN-10, Tergitol, Type TMN-6, Tetradecyl-beta-D-maltoside, Tetraethylene glycol monodecyl ether, Tetraethylene glycol monododecyl ether, Tetraethylene glycol monotetradecyl ether, Triethylene glycol monodecyl ether, Triethylene glycol monododecyl ether, Triethylene glycol monohexadecyl ether, Triethylene glycol monooctyl ether, Triethylene glycol monotetradecyl ether, Triton CF-21, Triton CF-32, Triton DF-12, Triton DF-16, Triton GR-5M, Triton QS-15, Triton QS-44, Triton X-100, Triton X-102, Triton X-15, Triton X-151, Triton X-200, Triton X-207, Triton® X-100, Triton® X-114, Triton® X-165, Triton® X-305, Triton® X-405, Triton® X-45, Triton® X-705-70, TWEEN® 20, TWEEN® 21, TWEEN® 40, TWEEN® 60, TWEEN® 61, TWEEN® 65, TWEEN® 80, TWEEN® 81, TWEEN® 85, Tyloxapol, n-Undecyl beta-D-glucopyranoside, semi-synthetic derivatives thereof, or combinations thereof.

In addition, the nonionic surfactant can be a poloxamer. Poloxamers are polymers made of a block of polyoxyethylene, followed by a block of polyoxypropylene, followed by a block of polyoxyethylene. The average number of units of polyoxyethylene and polyoxypropylene varies based on the number associated with the polymer. For example, the smallest polymer, Poloxamer 101, consists of a block with an average of 2 units of polyoxyethylene, a block with an average of 16 units of polyoxypropylene, followed by a block with an average of 2 units of polyoxyethylene. Poloxamers range from colorless liquids and pastes to white solids. In cosmetics and personal care products, Poloxamers are used in the formulation of skin cleansers, bath products, shampoos, hair conditioners, mouthwashes, eye makeup remover and other skin and hair products. Examples of Poloxamers include, but are not limited to, Poloxamer 101, Poloxamer 105, Poloxamer 108, Poloxamer 122, Poloxamer 123, Poloxamer 124, Poloxamer 181, Poloxamer 182, Poloxamer 183, Poloxamer 184, Poloxamer 185, Poloxamer 188, Poloxamer 212, Poloxamer 215, Poloxamer 217, Poloxamer 231, Poloxamer 234, Poloxamer 235, Poloxamer 237, Poloxamer 238, Poloxamer 282, Poloxamer 284, Poloxamer 288, Poloxamer 331, Poloxamer 333, Poloxamer 334, Poloxamer 335, Poloxamer 338, Poloxamer 401, Poloxamer 402, Poloxamer 403, Poloxamer 407, Poloxamer 105 Benzoate, and Poloxamer 182 Dibenzoate.

Suitable cationic surfactants include, but are not limited to, a quarternary ammonium compound, an alkyl trimethyl ammonium chloride compound, a dialkyl dimethyl ammonium chloride compound, a cationic halogen-containing compound, such as cetylpyridinium chloride, Benzalkonium chloride, Benzalkonium chloride, Benzyldimethylhexadecylammonium chloride, Benzyldimethyltetradecylammonium chloride, Benzyldodecyldimethylammonium bromide, Benzyltrimethylammonium tetrachloroiodate, Dimethyldioctadecylammonium bromide, Dodecylethyldimethylammonium bromide, Dodecyltrimethylammonium bromide, Dodecyltrimethylammonium bromide, Ethylhexadecyldimethylammonium bromide, Girard's reagent T, Hexadecyltrimethylammonium bromide, Hexadecyltrimethylammonium bromide, N,N',N'-Polyoxyethylene(10)-N-tallow-1,3-diaminopropane, Thonzonium bromide, Trimethyl(tetradecyl)ammonium bromide, 1,3,5-Triazine-1,3,5(2H,4H,6H)-triethanol, 1-Decanaminium, N-decyl-N,N-dimethyl-, chloride, Didecyl dimethyl ammonium chloride, 2-(2-(p-Diisobutyl)cresosxy)ethoxy)ethyl dimethyl benzyl ammonium chloride, 2-(2-(p-(Diisobutyl)phenoxy)ethoxy)ethyl dimethyl benzyl ammonium chloride, Alkyl 1 or 3 benzyl-1-(2-hydroxethyl)-2-imidazolinium chloride, Alkyl bis(2-hydroxyethyl)benzyl ammonium chloride, Alkyl demethyl benzyl ammonium chloride, Alkyl dimethyl 3,4-dichlorobenzyl ammonium chloride (100% C12), Alkyl dimethyl 3,4-dichlorobenzyl ammonium chloride (50% C14, 40% C12, 10% C16), Alkyl dimethyl 3,4-dichlorobenzyl ammonium chloride (55% C14, 23% C12, 20% C16), Alkyl dimethyl benzyl ammonium chloride, Alkyl dimethyl benzyl ammonium chloride (100% C14), Alkyl dimethyl benzyl ammonium chloride (100% C16), Alkyl dimethyl benzyl ammonium chloride (41% C14, 28% C12), Alkyl dimethyl benzyl ammonium chloride (47% C12, 18% C14), Alkyl dimethyl benzyl ammonium chloride (55% C16, 20% C14), Alkyl dimethyl benzyl ammonium chloride (58% C14, 28% C16), Alkyl dimethyl benzyl ammonium chloride (60% C14, 25% C12), Alkyl dimethyl benzyl ammonium chloride (61% C11, 23% C14), Alkyl dimethyl benzyl ammonium chloride (61% C12, 23% C14), Alkyl dimethyl benzyl ammonium chloride (65% C12, 25% C14), Alkyl dimethyl benzyl ammonium chloride (67% C12, 24% C14), Alkyl dimethyl benzyl ammonium chloride (67% C12, 25% C14), Alkyl dimethyl benzyl ammonium chloride (90% C14, 5% C12), Alkyl dimethyl benzyl ammonium chloride (93% C14, 4% C12), Alkyl dimethyl benzyl ammonium chloride (95% C16, 5% C18), Alkyl dimethyl benzyl ammonium chloride, Alkyl didecyl dimethyl ammonium chloride, Alkyl dimethyl benzyl ammonium chloride, Alkyl dimethyl benzyl ammonium chloride (C12-16), Alkyl dimethyl benzyl ammonium chloride (C12-18), Alkyl dimethyl benzyl ammonium chloride, dialkyl dimethyl benzyl ammonium chloride, Alkyl dimethyl dimethybenzyl ammonium chloride, Alkyl dimethyl ethyl ammonium bromide (90% C14, 5% C16, 5% C12), Alkyl dimethyl ethyl ammonium bromide (mixed alkyl and alkenyl groups as in the fatty acids of soybean oil), Alkyl dimethyl ethylbenzyl ammonium chloride, Alkyl dimethyl ethylbenzyl ammonium chloride (60% C14), Alkyl dimethyl isopropylbenzyl ammonium chloride (50% C12, 30% C14, 17% C16, 3% C18), Alkyl trimethyl ammonium chloride (58% C18, 40% C 16, 1% C14, 1% C12), Alkyl trimethyl ammonium chloride (90% C18, 10% C16), Alkyldimethyl (ethylbenzyl) ammonium chloride (C12-18), Di-(C8-10)-alkyl dimethyl ammonium chlorides, Dialkyl dimethyl ammonium chloride, Dialkyl methyl benzyl ammonium chloride, Didecyl dimethyl ammonium chloride, Diisodecyl dimethyl ammonium chloride, Dioctyl dimethyl ammonium chloride, Dodecyl bis(2-hydroxyethyl)octyl hydrogen ammonium chloride, Dodecyl dimethyl benzyl ammonium chloride, Dodecylcarbamoyl methyl dinethyl benzyl ammonium chloride, Heptadecyl hydroxyethylimidazolinium chloride, Hexahydro-1,3,5-tris(2-hydroxyethyl)-s-triazine, Hexahydro-1,3,5-tris(2-hydroxyethyl)-s-triazine, Myristalkonium chloride (and) Quat RNIUM 14, N,N-Dimethyl-2-hydroxypropylammonium chloride polymer, n-Tetradecyl dimethyl benzyl ammonium chloride monohydrate, Octyl decyl dimethyl ammonium chloride, Octyl dodecyl dimethyl ammonium chloride, Octyphenoxyethoxyethyl dimethyl benzyl ammonium chloride, Oxydiethylenebis(alkyl dimethyl ammonium chloride), Quaternary ammonium compounds, dicoco alkyldimethyl, chloride, Trimethoxysily propyl dimethyl octadecyl ammonium chloride, Trimethoxysilyl quats, Trimethyl dodecylbenzyl ammonium chloride, semi-synthetic derivatives thereof, and combinations thereof.

Exemplary cationic halogen-containing compounds include, but are not limited to, cetylpyridinium halides, cetyltrimethylammonium halides, cetyldimethylethylammonium halides, cetyldimethylbenzylammonium halides, cetyltributylphosphonium halides, dodecyltrimethylammonium halides, or tetradecyltrimethylammonium halides. In some particular embodiments, suitable cationic halogen containing compounds comprise, but are not limited to, cetylpyridinium chloride (CPC), cetyltrimethylammonium chloride, cetylbenzyldimethylammonium chloride, cetylpyridinium bromide (CPB), cetyltrimethylammonium bromide (CTAB), cetyidimethylethylammonium bromide, cetyltributylphosphonium bromide, dodecyltrimethylammonium bromide, and tetrad ecyltrimethylammonium bromide. In particularly preferred embodiments, the cationic halogen containing compound is CPC, although the compositions of the present invention are not limited to formulation with an particular cationic containing compound.

Suitable anionic surfactants include, but are not limited to, a carboxylate, a sulphate, a sulphonate, a phosphate, chenodeoxycholic acid, chenodeoxycholic acid sodium salt, cholic acid, ox or sheep bile, Dehydrocholic acid, Deoxycholic acid, Deoxycholic acid, Deoxycholic acid methyl ester, Digitonin, Digitoxigenin, N,N-Dimethyldodecyl amine N-oxide, Docusate sodium salt, Glycochenodeoxycholic acid sodium salt, Glycocholic acid hydrate, synthetic, Glycocholic acid sodium salt hydrate, synthetic, Glycodeoxycholic acid monohydrate, Glycodeoxycholic acid sodium salt, Glycodeoxycholic acid sodium salt, Glycolithocholic acid 3-sulfate disodium salt, Glycolithocholic acid ethyl ester, N-Lauroylsarcosine sodium salt, N-Lauroylsarcosine solution, N-Lauroylsarcosine solution, Lithium dodecyl sulfate, Lithium dodecyl sulfate, Lithium dodecyl sulfate, Lugol solution, Niaproof 4, Type 4, 1 -Octanesulfonic acid sodium salt, Sodium 1-butanesulfonate, Sodium 1-decanesulfonate, Sodium 1-decanesulfonate, Sodium 1-dodecanesulfonate, Sodium 1-heptanesulfonate anhydrous, Sodium 1-heptanesulfonate anhydrous, Sodium 1-nonanesulfonate, Sodium 1-propanesulfonate monohydrate, Sodium 2-bromoethanesulfonate, Sodium cholate hydrate, Sodium choleate, Sodium deoxycholate, Sodium deoxycholate monohydrate, Sodium dodecyl sulfate, Sodium hexanesulfonate anhydrous, Sodium octyl sulfate, Sodium pentanesulfonate anhydrous, Sodium taurocholate, Taurochenodeoxycholic acid sodium salt, Taurodeoxycholic acid sodium salt monohydrate, Taurohyodeoxycholic acid sodium salt hydrate, Taurolithocholic acid 3-sulfate disodium salt, Tauroursodeoxycholic acid sodium salt, Trizma® dodecyl sulfate, TWEEN® 80, Ursodeoxycholic acid, semi-synthetic derivatives thereof, and combinations thereof.

Suitable zwitterionic surfactants include, but are not limited to, an N-alkyl betaine, lauryl amindo propyl dimethyl betaine, an alkyl dimethyl glycinate, an N-alkyl amino propionate, CHAPS, minimum 98% (TLC), CHAPS, SigmaUltra, minimum 98% (TLC), CHAPS, for electrophoresis, minimum 98% (TLC), CHAPSO, minimum 98%, CHAPSO, SigmaUltra, CHAPSO, for electrophoresis, 3-(Decyldimethylammonio)propanesulfonate inner salt, 3-Dodecyldimethylammonio)propanesulfonate inner salt, SigmaUltra, 3-(Dodecyldimethylammonio)propanesulfonate inner salt, 3-(N,N-Dimethylmyristylammonio)propanesulfonate, 3-(N,N-Dimethyloctadecylammonio)propanesulfonate, 3-(N,N-Dimethyloctylammonio)propanesulfonate inner salt, 3-(N,N-Dimethylpalmitylammonio)propanesulfonate, semi-synthetic derivatives thereof, and combinations thereof.

In some embodiments, the nanoemulsion vaccine comprises a cationic surfactant, which can be cetylpyridinium chloride. In other embodiments of the invention, the nanoemulsion vaccine comprises a cationic surfactant, and the concentration of the cationic surfactant is less than about 5.0% and greater than about 0.001%. In yet another embodiment of the invention, the nanoemulsion vaccine comprises a cationic surfactant, and the concentration of the cationic surfactant is selected from the group consisting of less than about 5%, less than about 4.5%, less than about 4.0%, less than about 3.5%, less than about 3.0%, less than about 2.5%, less than about 2.0%, less than about 1.5%, less than about 1.0%, less than about 0.90%, less than about 0.80%, less than about 0.70%, less than about 0.60%, less than about 0.50%, less than about 0.40%, less than about 0.30%, less than about 0.20%, or less than about 0.10%. Further, the concentration of the cationic agent in the nanoemulsion vaccine is greater than about 0.002%, greater than about 0.003%, greater than about 0.004%, greater than about 0.005%, greater than about 0.006%, greater than about 0.007%, greater than about 0.008%, greater than about 0.009%, greater than about 0.010%, or greater than about 0.001%. In one embodiment, the concentration of the cationic agent in the nanoemulsion vaccine is less than about 5.0% and greater than about 0.001%.

In another embodiment of the invention, the nanoemulsion vaccine comprises at least one cationic surfactant and at least one non-cationic surfactant. The non-cationic surfactant is a nonionic surfactant, such as a polysorbate (Tween), such as polysorbate 80 or polysorbate 20. In one embodiment, the non-ionic surfactant is present in a concentration of about 0.01% to about 5.0%, or the non-ionic surfactant is present in a concentration of about 0.1% to about 3%. In yet another embodiment of the invention, the nanoemulsion vaccine comprises a cationic surfactant present in a concentration of about 0.01 % to about 2%, in combination with a nonionic surfactant.

5. Additional Ingredients

Additional compounds suitable for use in the nanoemulsion vaccines of the invention include but are not limited to one or more solvents, such as an organic phosphate-based solvent, bulking agents, coloring agents, pharmaceutically acceptable excipients, a preservative, pH adjuster, buffer, chelating agent, etc. The additional compounds can be admixed into a previously emulsified nanoemulsion vaccine, or the additional compounds can be added to the original mixture to be emulsified. In certain of these embodiments, one or more additional compounds are admixed into an existing nanoemulsion composition immediately prior to its use.

Suitable preservatives in the nanoemulsion vaccines of the invention include, but are not limited to, cetylpyridinium chloride, benzalkonium chloride, benzyl alcohol, chlorhexidine, imidazolidinyl urea, phenol, potassium sorbate, benzoic acid, bronopol, chlorocresol, paraben esters, phenoxyethanol, sorbic acid, alpha-tocophernol, ascorbic acid, ascorbyl palmitate, butylated hydroxyanisole, butylated hydroxytoluene, sodium ascorbate, sodium metabisulphite, citric acid, edetic acid, semi-synthetic derivatives thereof, and combinations thereof. Other suitable preservatives include, but are not limited to, benzyl alcohol, chlorhexidine (bis(p-chlorophenyldiguanido)hexane), chlorphenesin (3-(-4-chloropheoxy)-propane-1,2-diol), Kathon C G (methyl and methylchloroisothiazolinone), parabens (methyl, ethyl, propyl, butyl hydrobenzoates), phenoxyethanol(2-phenoxyethanol), sorbic acid (potassium sorbate, sorbic acid), Phenonip (phenoxyethanol, methyl, ethyl, butyl, propyl parabens), Phenoroc (phenoxyethanol 0.73%, methyl paraben 0.2%, propyl paraben 0.07%), Liquipar Oil (isopropyl, isobutyl, butylparabens), Liquipar PE (70% phenoxyethanol, 30% liquipar oil), Nipaguard MPA (benzyl alcohol (70%), methyl & propyl parabens), Nipaguard MPS (propylene glycol, methyl & propyl parabens), Nipasept (methyl, ethyl and propyl parabens), Nipastat (methyl, butyl, ethyl and propyel parabens), Elestab 388 (phenoxyethanol in propylene glycol plus chlorphenesin and methylparaben), and Killitol (7.5% chlorphenesin and 7.5% methyl parabens).

The nanoemulsion vaccine may further comprise at least one pH adjuster. Suitable pH adjusters in the nanoemulsion vaccine of the invention include, but are not limited to, diethyanolamine, lactic acid, monoethanolamine, triethylanolamine, sodium hydroxide, sodium phosphate, semi-synthetic derivatives thereof, and combinations thereof.

In addition, the nanoemulsion vaccine can comprise a chelating agent. In one embodiment of the invention, the chelating agent is present in an amount of about 0.0005% to about 1%. Examples of chelating agents include, but are not limited to, ethylenediamine, ethylenediaminetetraacetic acid (EDTA), phytic acid, polyphosphoric acid, citric acid, gluconic acid, acetic acid, lactic acid, and dimercaprol, and a preferred chelating agent is ethylenediaminetetraacetic acid.

The nanoemulsion vaccine can comprise a buffering agent, such as a pharmaceutically acceptable buffering agent. Examples of buffering agents include, but are not limited to, 2-Amino-2-methyl-1,3-propanediol, ≥99.5% (NT), 2-Amino-2-methyl-1-propanol, ≥99.0% (GC), L-(+)-Tartaric acid, ≥99.5% (T), ACES, ≥99.5% (T), ADA, ≥99.0% (T), Acetic acid, ≥99.5% (GC/T), Acetic acid, for luminescence, ≥99.5% (GC/T), Ammonium acetate solution, for molecular biology, ~5 M in $H_2O$, Ammonium acetate, for luminescence, ≥99.0% (calc. on dry substance, T), Ammonium bicarbonate, ≥99.5% (T), Ammonium citrate dibasic, ≥99.0% (T), Ammonium formate solution, 10 M in $H_2O$, Ammonium formate, ≥99.0% (calc. based on dry substance, NT), Ammonium oxalate monohydrate, ≥99.5% (RT), Ammonium phosphate dibasic solution, 2.5 M in $H_2O$, Ammonium phosphate dibasic, ≥99.0% (T), Ammonium phosphate monobasic solution, 2.5 M in $H_2O$, Ammonium phosphate monobasic, ≥99.5% (T), Ammonium sodium phosphate dibasic tetrahydrate, ≥99.5% (NT), Ammonium sulfate solution, for molecular biology, 3.2 M in $H_2O$, Ammonium tartrate dibasic solution, 2 M in $H_2O$ (colorless solution at 20° C.), Ammonium tartrate dibasic, ≥99.5% (T), BES buffered saline, for molecular biology, 2× concentrate, BES, ≥99.5% (T), BES, for molecular biology, ≥99.5% (T), BICINE buffer Solution, for molecular biology, 1 M in $H_2O$, BICINE, ≥99.5% (T), BIS-TRIS, ≥99.0% (NT), Bicarbonate buffer solution, >0.1 M $Na_2CO_3$, >0.2 M $NaHCO_3$, Boric acid, ≥99.5% (T), Boric acid, for molecular biology, ≥99.5% (T), CAPS, ≥99.0% (TLC), CHES, ≥99.5% (T), Calcium acetate hydrate, ≥99.0% (calc. on dried material, KT), Calcium carbonate, precipitated, ≥99.0% (KT), Calcium citrate tribasic tetrahydrate, ≥98.0% (calc. on dry substance, KT), Citrate Concentrated Solution, for molecular biology, 1 M in $H_2O$, Citric acid, anhydrous, ≥99.5% (T), Citric acid, for luminescence, anhydrous, ≥99.5% (T), Diethanolamine, ≥99.5% (GC), EPPS, ≥99.0% (T), Ethylenediaminetetraacetic acid disodium salt dihydrate, for molecular biology, ≥99.0% (T), Formic acid solution, 1.0 M in $H_2O$, Gly-Gly-Gly, ≥99.0% (NT), Gly-Gly, ≥99.5% (NT), Glycine, ≥99.0% (NT), Glycine, for luminescence, ≥99.0% (NT), Glycine, for molecular biology, ≥99.0% (NT), HEPES buffered saline, for molecular biology, 2× concentrate, HEPES, ≥99.5% (T), HEPES, for molecular biology, ≥99.5% (T), Imidazole buffer Solution, 1 M in $H_2O$, Imidazole, ≥99.5% (GC), Imidazole, for luminescence, ≥99.5% (GC), Imidazole, for molecular biology, ≥99.5% (GC), Lipoprotein Refolding Buffer, Lithium acetate dihydrate, ≥99.0% (NT), Lithium citrate tribasic tetrahydrate, ≥99.5% (NT), MES hydrate, ≥99.5% (T), MES monohydrate, for luminescence, ≥99.5% (T), MES solution, for molecular biology, 0.5 M in $H_2O$, MOPS, ≥99.5% (T), MOPS, for luminescence, ≥99.5% (T), MOPS, for molecular biology, ≥99.5% (T), Magnesium acetate solution, for molecular biology, ~1 M in H$_2$O, Magnesium acetate tetrahydrate, ≥99.0% (KT), Magnesium citrate tribasic nonahydrate, ≥98.0% (calc. based on dry substance, KT), Magnesium formate solution, 0.5 M in H$_2$O, Magnesium phosphate dibasic trihydrate, ≥98.0% (KT), Neutralization solution for the in-situ hybridization for in-situ hybridization, for molecular biology, Oxalic acid dihydrate, ≥99.5% (RT), PIPES, ≥99.5% (T), PIPES, for molecular biology, ≥99.5% (T), Phosphate buffered saline, solution (autoclaved), Phosphate buffered saline, washing buffer for peroxidase conjugates in Western Blotting, 10× concentrate, Piperazine, anhydrous, ≥99.0% (T), Potassium D-tartrate monobasic, ≥99.0% (T), Potassium acetate solution, for molecular biology, Potassium acetate solution, for molecular biology, 5 M in H$_2$O, Potassium acetate solution, for molecular biology, ~1 M in H$_2$O, Potassium acetate, ≥99.0% (NT), Potassium acetate, for luminescence, ≥99.0% (NT), Potassium acetate, for molecular biology, ≥99.0% (NT), Potassium bicarbonate, ≥99.5% (T), Potassium carbonate, anhydrous, ≥99.0% (T), Potassium chloride, ≥99.5% (AT), Potassium citrate monobasic, ≥99.0% (dried material, NT), Potassium citrate tribasic solution, 1 M in H$_2$O, Potassium formate solution, 14 M in H$_2$O, Potassium formate, ≥99.5% (NT), Potassium oxalate monohydrate, ≥99.0% (RT), Potassium phosphate dibasic, anhydrous, ≥99.0% (T), Potassium phosphate dibasic, for luminescence, anhydrous, ≥99.0% (T), Potassium phosphate dibasic, for molecular biology, anhydrous, ≥99.0% (T), Potassium phosphate monobasic, anhydrous, ≥99.5% (T), Potassium phosphate monobasic, for molecular biology, anhydrous, ≥99.5% (T), Potassium phosphate tribasic monohydrate, ≥95% (T), Potassium phthalate monobasic, ≥99.5% (T), Potassium sodium tartrate solution, 1.5 M in H$_2$O, Potassium sodium tartrate tetrahydrate, ≥99.5% (NT), Potassium tetraborate tetrahydrate, ≥99.0% (T), Potassium tetraoxalate dihydrate, ≥99.5% (RT), Propionic acid solution, 1.0 M in H$_2$O, STE buffer solution, for molecular biology, pH 7.8, STET buffer solution, for molecular biology, pH 8.0, Sodium 5,5-diethylbarbiturate, ≥99.5% (NT), Sodium acetate solution, for molecular biology, ~3 M in H$_2$O, Sodium acetate trihydrate, ≥99.5% (NT), Sodium acetate, anhydrous, ≥99.0% (NT), Sodium acetate, for luminescence, anhydrous, ≥99.0% (NT), Sodium acetate, for molecular biology, anhydrous, ≥99.0% (NT), Sodium bicarbonate, ≥99.5% (T), Sodium bitartrate monohydrate, ≥99.0% (T), Sodium carbonate decahydrate, ≥99.5% (T), Sodium carbonate, anhydrous, ≥99.5% (calc. on dry substance, T), Sodium citrate monobasic, anhydrous, ≥99.5% (T), Sodium citrate tribasic dihydrate, ≥99.0% (NT), Sodium citrate tribasic dihydrate, for luminescence, ≥99.0% (NT), Sodium citrate tribasic dihydrate, for molecular biology, ≥99.5% (NT), Sodium formate solution, 8 M in H$_2$O, Sodium oxalate, ≥99.5% (RT), Sodium phosphate dibasic dihydrate, ≥99.0% (T), Sodium phosphate dibasic dihydrate, for luminescence, ≥99.0% (T), Sodium phosphate dibasic dihydrate, for molecular biology, ≥99.0% (T), Sodium phosphate dibasic dodecahydrate, ≥99.0% (T), Sodium phosphate dibasic solution, 0.5 M in H$_2$O, Sodium phosphate dibasic, anhydrous, ≥99.5% (T), Sodium phosphate dibasic, for molecular biology, ≥99.5% (T), Sodium phosphate monobasic dihydrate, ≥99.0% (T), Sodium phosphate monobasic dihydrate, for molecular biology, ≥99.0% (T), Sodium phosphate monobasic monohydrate, for molecular biology, ≥99.5% (T), Sodium phosphate monobasic solution, 5 M in H$_2$O, Sodium pyrophosphate dibasic, ≥99.0% (T), Sodium pyrophosphate tetrabasic decahydrate, ≥99.5% (T), Sodium tartrate dibasic dihydrate, ≥99.0% (NT), Sodium tartrate dibasic solution, 1.5 M in H$_2$O (colorless solution at 20° C.), Sodium tetraborate decahydrate, ≥99.5% (T), TAPS, ≥99.5% (T), TES, ≥99.5% (calc. based on dry substance, T), TM buffer solution, for molecular biology, pH 7.4, TNT buffer solution, for molecular biology, pH 8.0, TRIS Glycine buffer solution, 10× concentrate, TRIS acetate—EDTA buffer solution, for molecular biology, TRIS buffered saline, 10× concentrate, TRIS glycine SDS buffer solution, for electrophoresis, 10× concentrate, TRIS phosphate—EDTA buffer solution, for molecular biology, concentrate, 10× concentrate, Tricine, ≥99.5% (NT), Triethanolamine, ≥99.5% (GC), Triethylamine, ≥99.5% (GC), Triethylammonium acetate buffer, volatile buffer, ~1.0 M in H$_2$O, Triethylammonium phosphate solution, volatile buffer, ~1.0 M in H$_2$O, Trimethylammonium acetate solution, volatile buffer, ~1.0 M in H$_2$O, Trimethylammonium phosphate solution, volatile buffer, ~1 M in H$_2$O, Tris-EDTA buffer solution, for molecular biology, concentrate, 100× concentrate, Tris-EDTA buffer solution, for molecular biology, pH 7.4, Tris-EDTA buffer solution, for molecular biology, pH 8.0, Trizma® acetate, ≥99.0% (NT), Trizma® base, ≥99.8% (T), Trizma® base, ≥99.8% (T), Trizma® base, for luminescence, ≥99.8% (T), Trizma® base, for molecular biology, ≥99.8% (T), Trizma® carbonate, ≥98.5% (T), Trizma® hydrochloride buffer solution, for molecular biology, pH 7.2, Trizma® hydrochloride buffer solution, for molecular biology, pH 7.4, Trizma® hydrochloride buffer solution, for molecular biology, pH 7.6, Trizma® hydrochloride buffer solution, for molecular biology, pH 8.0, Trizma® hydrochloride, ≥99.0% (AT), Trizma® hydrochloride, for luminescence, ≥99.0% (AT), Trizma® hydrochloride, for molecular biology, ≥99.0% (AT), and Trizma® maleate, ≥99.5% (NT).

The nanoemulsion vaccine can comprise one or more emulsifying agents to aid in the formation of emulsions. Emulsifying agents include compounds that aggregate at the oil/water interface to form a kind of continuous membrane that prevents direct contact between two adjacent droplets. Certain embodiments of the present invention feature nanoemulsion vaccines that may readily be diluted with water or another aqueous phase to a desired concentration without impairing their desired properties.

G. Pharmaceutical Compositions

The nanoemulsion vaccines of the invention may be formulated into pharmaceutical compositions that comprise the nanoemulsion vaccine in a therapeutically effective amount and suitable, pharmaceutically-acceptable excipients for pharmaceutically acceptable delivery. Such excipients are well known in the art.

By the phrase "therapeutically effective amount" it is meant any amount of the nanoemulsion vaccine that is effective in preventing, treating or ameliorating a disease caused by the pathogen associated with the immunogen administered in the composition comprising the nanoemulsion vaccine. By "protective immune response" it is meant that the immune response associated with prevention, treating, or amelioration of a disease. Complete prevention is not required, though is encompassed by the present invention. The immune response can be evaluated using the methods discussed herein or by any method known by a person of skill in the art.

Intranasal administration includes administration via the nose, either with or without concomitant inhalation during administration. Such administration is typically through contact by the composition comprising the nanoemulsion vaccine with the nasal mucosa, nasal turbinates or sinus cavity. Administration by inhalation comprises intranasal administration, or may include oral inhalation. Such administration may also include contact with the oral mucosa, bronchial mucosa, and other epithelia.

Exemplary dosage forms for pharmaceutical administration are described herein. Examples include but are not limited to liquids, ointments, creams, emulsions, lotions, gels, bioadhesive gels, sprays, aerosols, pastes, foams, sunscreens, capsules, microcapsules, suspensions, pessary, powder, semi-solid dosage form, etc.

The pharmaceutical compositions may be formulated for immediate release, sustained release, controlled release, delayed release, or any combinations thereof, into the epidermis or dermis. In some embodiments, the formulations may comprise a penetration-enhancing agent. Suitable penetration-enhancing agents include, but are not limited to, alcohols such as ethanol, triglycerides and aloe compositions. The amount of the penetration-enhancing agent may comprise from about 0.5% to about 40% by weight of the formulation.

The nanoemulsion vaccines of the invention can be applied and/or delivered utilizing electrophoretic delivery/electrophoresis. Further, the composition may be a transdermal delivery system such as a patch or administered by a pressurized or pneumatic device (i.e., "gene gun").

Such methods, which comprise applying an electrical current, are well known in the art.

The pharmaceutical compositions for administration may be applied in a single administration or in multiple administrations.

If applied topically, the nanoemulsion may be occluded or semi-occluded. Occlusion or semi-occlusion may be performed by overlaying a bandage, polyoleofin film, article of clothing, impermeable barrier, or semi-impermeable barrier to the topical preparation.

An exemplary nanoemulsion adjuvant composition according to the invention is designated "$W_{80}5EC$" adjuvant. The composition of $W_{80}5EC$ adjuvant is shown in the table below (Table 1). The mean droplet size for the $W_{80}5EC$ adjuvant is ~400 nm. All of the components of the nanoemulsion are included on the FDA inactive ingredient list for Approved Drug Products.

TABLE 1

$W_{80}5EC$ Formulation

| Function | $W_{80}5EC$-Adjuvant<br>Mean Droplet Size ≈ 400 nm |
|---|---|
| Aqueous Diluent | Purified Water, USP |
| Hydrophobic Oil (Core) | Soybean Oil, USP (super refined) |
| Organic Solvent | Dehydrated Alcohol, USP (anhydrous ethanol) |
| Surfactant | Polysorbate 80, NF |
| Emulsifying Agent Preservative | Cetylpyridinium Chloride, USP |

The nanoemulsion adjuvants are formed by emulsification of an oil, purified water, nonionic detergent, organic solvent and surfactant, such as a cationic surfactant. An exemplary specific nanoemulsion adjuvant is designated as "60% $W_{80}5EC$". The 60% $W_{80}5EC$-adjuvant is composed of the ingredients shown in Table 2 below: purified water, USP; soybean oil USP; Dehydrated Alcohol, USP [anhydrous ethanol]; Polysorbate 80, NF and cetylpyridinium chloride, USP (CPCAll components of this exemplary nanoemulsion are included on the FDA list of approved inactive ingredients for Approved Drug Products.

TABLE 2

Composition of 60% $W_{80}5EC$-Adjuvant (w/w %)

| Ingredients | 60% $W_{80}5EC$ |
|---|---|
| Purified Water, USP | 54.10% |
| Soybean Oil, USP | 37.67% |
| Dehydrated Alcohol, USP (anhydrous ethanol) | 4.04% |
| Polysorbate 80, NF | 3.55% |
| Cetylpyridinium Chloride, USP | 0.64% |

H. Methods of Manufacture

The nanoemulsions of the invention can be formed using classic emulsion forming techniques. See e.g., U.S. 2004/0043041. In an exemplary method, the oil is mixed with the aqueous phase under relatively high shear forces (e.g., using high hydraulic and mechanical forces) to obtain a nanoemulsion comprising oil droplets having an average diameter of less than about 1000 nm. Some embodiments of the invention employ a nanoemulsion having an oil phase comprising an alcohol such as ethanol. The oil and aqueous phases can be blended using any apparatus capable of producing shear forces sufficient to form an emulsion, such as French Presses or high shear mixers (e.g., FDA approved high shear mixers are available, for example, from Admix, Inc., Manchester, N.H.). Methods of producing such emulsions are described in U.S. Pat. Nos. 5,103,497 and 4,895,452, herein incorporated by reference in their entireties.

In an exemplary embodiment, the nanoemulsions used in the methods of the invention comprise droplets of an oily discontinuous phase dispersed in an aqueous continuous phase, such as water or PBS. The nanoemulsions of the invention are stable, and do not deteriorate even after long storage periods. Certain nanoemulsions of the invention are non-toxic and safe when swallowed, inhaled, or contacted to the skin of a subject.

The compositions of the invention can be produced in large quantities and are stable for many months at a broad range of temperatures. The nanoemulsion can have textures ranging from that of a semi-solid cream to that of a thin lotion, to that of a liquid and can be applied topically by any pharmaceutically acceptable method as stated above, e.g., by hand, or nasal drops/spray.

As stated above, at least a portion of the emulsion may be in the form of lipid structures including, but not limited to, unilamellar, multilamellar, and paucliamellar lipid vesicles, micelles, and lamellar phases.

The present invention contemplates that many variations of the described nanoemulsions will be useful in the methods of the present invention. To determine if a candidate nanoemulsion is suitable for use with the present invention, three criteria are analyzed. Using the methods and standards described herein, candidate emulsions can be easily tested to determine if they are suitable. First, the desired ingredients are prepared using the methods described herein, to determine if a nanoemulsion can be formed. If a nanoemulsion cannot be formed, the candidate is rejected. Second, the candidate nanoemulsion should form a stable emulsion. A nanoemulsion is stable if it remains in emulsion form for a sufficient period to allow its intended use. For example, for nanoemulsions that are to be stored, shipped, etc., it may be desired that the nanoemulsion remain in emulsion form for months to years. Typical nanoemulsions that are relatively unstable, will lose their form within a day. Third, the candidate nanoemulsion should have efficacy for its intended use. For example, the emulsions of the invention should kill or disable influenza virus to a detectable level, or induce a protective immune response to a detectable level. The nanoemulsion of the invention can be provided in many different types of containers and delivery systems. For example, in some embodiments of the invention, the nanoemulsions are provided in a cream or other solid or semi-solid form. The nanoemulsions of the invention may be incorporated into hydrogel formulations.

The nanoemulsions can be delivered (e.g., to a subject or customers) in any suitable container. Suitable containers can be used that provide one or more single use or multi-use dosages of the nanoemulsion for the desired application. In some embodiments of the invention, the nanoemulsions are provided in a suspension or liquid form. Such nanoemulsions can be delivered in any suitable container including spray bottles and any suitable pressurized spray device. Such spray bottles may be suitable for delivering the nanoemulsions intranasally or via inhalation.

These nanoemulsion-containing containers can further be packaged with instructions for use to form kits.

The invention is further described by reference to the following examples, which are provided for illustration only. The invention is not limited to the examples, but rather includes all variations that are evident from the teachings provided herein. All publicly available documents referenced herein, including but not limited to U.S. patents, are specifically incorporated by reference.

EXAMPLES

Example 1

Virus Inactivation 1.1 Virus Preparation

Influenza H3N2 Strain A/Wisconsin/67/2005 was obtained from the Centers for Disease Control. The virus was propagated in the allantoic cavity of 10 day embryonic hens' eggs according to standard procedures. The allantoic fluid was clarified by low speed centrifugation. The influenza virus was concentrated from the low speed supernatant by high speed centrifugation and purified using a sucrose gradient.

1.2 Virus Inactivation

To compare the effectiveness of inactivation of influenza by nanoemulsion compositions with the standard method of β-propiolactone (βPL) inactivation, virus generated in Section 1.1 was treated as follows.

The nanoemulsion (NE) composition was formulated according to Table 3.

TABLE 3

Nanoemulsion composition

| Component | Concentration v/v |
|---|---|
| Water | 84.7% |
| Soybean Oil | 12.6% |
| Ethanol | 1.35% |
| Polysorbate 80 | 1.18% |
| Cetylpyridinium chloride (CPC) | 0.2% |

Method of Nanoemulsion Inactivation: For inactivation, the virus was incubated with NE at a final concentration of 20% at 37° C. for four hours, then the virus was stored at 4° C. and tested for the presence of infectious particles.

Conventional Method of Inactivation: βPL was added to the virus at a final concentration of 0.1% v/v for 24 hours at 4° C. followed by inactivation of the βPL at 37° C. for 2 hours. Following inactivation with βPL, nanoemulsion vaccines were prepared by mixing the nanoemulsion with the βPL-inactivated virus. The vaccine was stored at 4° C. until administered.

Results: To test for the absence of infectious influenza particles in the vaccine preparations, samples of the inactivated virus mixtures were incubated on MDCK cells (obtained from the American Type Culture Collection) to assess residual infectivity through three serial passages. No infection was observed at the assay detection limit for both inactivation methods, indicating that infectious virus was inactivated.

Example 2

Efficacy of Nanoemulsion Influenza Vaccine in Animal Model

The goal of this study was to ascertain the efficacy of vaccine with nanoemulsion to protect against subsequent infection by H3N2 virus in a ferret model.

Ferret Study #1

Ferret study #1 was an investigation to evaluate the adjuvant properties of the $W_{80}5EC$-adjuvant with whole influenza virus inactivated by various methods.

2.1 Animals:

Approximately 5-to 8-month-old, influenza naive, castrated and descented, male Fitch ferrets (*Mustela putorius furo*) were used in this study.

Ferret prebleed serum was tested for the presence of hemagglutination inhibiting (HAI) antibodies to currently circulating human influenza viruses using HAI assay. Animals demonstrating an HAI titer of >10 hemagglutination units (HAU) were excluded from the study. Animals were quarantined in an ABSL-3 (Animal biosafety level) facility for a period of at least 4-7 days. During the quarantine period animals were assessed for general animal health. Approximately 4 days prior to treatment animals were implanted with a temperature transponder (BioMedic Data Systems, Inc., Seaford, Del.).

Ferrets were housed in an AAALAC-accredited facility. All procedures were in accordance with the NRC Guide for the Care and Use of Laboratory Animals, the Animal Welfare Act, and the CDC•NIH Biosafety in Microbiological and Biomedical Laboratories. All experiments with influenza virus were conducted in a registered ABSL-2/BSL-2 facility.

2.2 Treatment (Dosing) and Blood Collection:

The formulations were stored at 4° C. prior to use. Ten groups of ferrets (N=12/group) were treated on days 1 and 28. The treatment schedule was as given in FIG. 1 and Table 4 below:

TABLE 4

Dosing of ferrets with test article

| Dose Group | Article Administered | Dose Route | HA Dose Level (µg) | Treatment Dose Volume (µL/nare) | Challenge Dose Volume (mL/nare) | # Animals |
|---|---|---|---|---|---|---|
| 1 | $W_{80}5EC$- | IN | 7.5 | 250 | 0.5 | 12 |
| 2 | Inactivated | IN | 15 | 250 | 0.5 | 12 |
| 3 | Wisconsin Virus | IN | 45 | 250 | 0.5 | 12 |
| 4 | βPL-inactivated | IN | 7.5 | 250 | 0.5 | 12 |

TABLE 4-continued

Dosing of ferrets with test article

| Dose Group | Article Administered | Dose Route | HA Dose Level (μg) | Treatment Dose Volume (μL/nare) | Challenge Dose Volume (mL/nare) | # Animals |
|---|---|---|---|---|---|---|
| 5 | Wisconsin virus + | IN | 15 | 250 | 0.5 | 12 |
| 6 | $W_{80}5EC$ | IN | 45 | 250 | 0.5 | 12 |
| 7 | βPL-inactivated Wisconsin virus | IN | 15 | 250 | 0.5 | 12 |
| 8 | βPL-inactivated Wisconsin virus | IM | 15 | 250/thigh | 0.5 | 12 |
| 9 | Fluvirin ® (βPL-Inactivated) | IM | 0 | 250/thigh | 0.5 | 12 |
| 10 | PBS control | IN | 0 | 250 | 0.5 | 12 |

Blood was collected on Day 1 (prior to vaccination), Day 27 (prior to revaccination) and Day 48 (prior to challenge).

Previously seronegative ferrets were challenged with $10^6$ $EID_{50}$ (Egg Infectious Dose$_{50}$) of A/Wisconsin/67/2005 (H3N2) virus on day 49 following vaccination with the same virus. Nasal washes were collected on days 1, 2, 3, 4 and 6 after challenge and titrated for viral concentration. Subgroups of the ferrets were sacrificed on day 5 post challenge to determine viral load in the nasal turbinates and lung.

The animals were observed twice daily for morbidity and mortality, and clinical signs, body weights and body temperatures were evaluated weekly.

2.3 Preparation and Characterization of Influenza Virus for Challenge:

The H3N2 influenza virus, A/Wisconsin/67/2005, was provided by the CDC (Atlanta, Ga.), amplified in embryonated eggs, and used to challenge ferrets. The virus was assessed to have a 50% egg infectious dose of $1\times10^{11.25}$ $EID_{50}$/mL. For challenge, the virus was adjusted to $10^6$ $EID_{50}$/mL.

2.4 Challenge and Monitoring of Ferrets:

On Day 49 ferrets were challenged with $10^6$ $EID_{50}$/mL of A/Wisconsin/67/2005. At the time of challenge, ferrets were first anesthetized followed by intranasal (I.N.) administration of virus with a total of $1\times10^6$ $EID_{50}$/mL of A/Wisconsin/67/2005 in a volume of 1.0 ml PBS, delivered to the nostrils (0.5 ml/nostril) according to standard procedures.

Ferrets were examined daily for clinical signs of infection including weight loss, change in temperature, nasal and ocular discharge, dyspnea, neurological signs.

2.5 Collection of Ferret Nasal Wash, Lungs, Nasal Turbinate and Lung Samples:

Ferrets were sedated and weighed. Nasal wash (NW) samples were collected by flushing the nares with PBS, 1% BSA and antibiotic solution (0.5 ml/nare), allowing the ferret to sneeze into a Petri dish and collection of the expelled PBS solution on Days 1, 2, 3, 4, 5 and 6 post challenge and processed according to standard procedures. Nasal washes were collected in tubes, placed on dry ice and subsequently stored at ≤−70° C. until viral load determination was done in embroynated eggs. On Day 54 four animals per group were necropsied; samples of lung, lung flush and nasal turbinates were collected, stored at −80° C. until viral load determination was done in embroynated hens' eggs.

Ferrets were euthanized on Day 63.

2.6 HAI Titers in Vaccinated Animals:

Ferret sera were treated with receptor-destroying enzyme (RDE-Tx) according to established procedures (WHO 2004). RDE-Tx sera were serially two-fold diluted in v-bottom microtiter plates. An equal volume of virus, adjusted to approximately 8 HAU/50 μl, was added to each well. The plates were covered and incubated at room temperature for 30 minutes followed by the addition of 0.5% turkey erythrocytes (TRBC). The plates were mixed by agitation, covered, and the TRBC were allowed to settle for 30 minutes at room temperature. The HAI titer was determined by the reciprocal dilution of the last row which contained non-agglutinated TRBC. Positive and negative serum controls were included for each plate. Samples were run in singlet in two independent assays. Results were compared and samples with a >2-fold difference in titer were repeated in a third assay. Geometric mean titers (GMT) were determined on the duplicate results.

2.7 Viral Load Determination in Nasal Wash Samples:

Frozen nasal wash samples were resuspended in PBS-Ab [Phosphate buffered saline supplemented with antibiotics (100 U/mL Penicillin, 100 μg/mL Streptomycin, 50 μg/mL Gentamicin)] to make 10% w/v suspension and homogenized. The homogenates were clarified by centrifugation and the resulting supernatants were serially diluted ($log_{10}$) in PBS-Ab. Ten day old embryonated chicken eggs (S&G Poultry, Clanton Ala.) were inoculated in triplicate with serially diluted tissue/nasal wash homogenates, 0.1 mL/egg, and incubated for approximately 24 Hr at 33° C. without $CO_2$. Virus growth was assessed for tissue/nasal wash homogenates by determination of HA positivity of allantoic fluid using 0.5% v/v TRBC. The 50% endpoint was determined by the method of Reed and Muench (Reed, L. J., and H. Muench. 1938. A simple method of estimating 50 per cent end-points. Amer. Jour. Hygiene, 27: 493-497.) from egg dilutions testing positive for HA activity in HRBC. Results were expressed as $EID_{50}$/ml. The initial sample dilution of 1:100 (1% w/v) was utilized to achieve a final sample volume sufficient for use in the assay; therefore, the limit of detection was $1\times10^{1.5}$ $EID_{50}$/100 μL or $1\times10^{2.5}$/$EID_{50}$/ml.

2.8 Cross Reactivity with Other Antigens:

Vaccinated ferrets were tested for antibody titers against H3N2 strains A/California and A/Panama, as well as H1N1 strain A/Solomon Islands, Influenza B strain B/Malaysia and H5N1 strain A/Vietnam, which were not used for challenging the ferrets.

Ferret sera were treated with receptor-destroying enzyme (RDE-Tx) according to established procedures (WHO 2004). RDE-Tx sera were serially two-fold diluted in v-bottom microtiter plates. An equal volume of virus (depending on the assay), adjusted to approximately 8 HAU/50 μl, was added to each well. The plates were covered and incubated at room temperature for 30 minutes followed by the addition of 0.5% turkey erythrocytes (TRBC). The plates were mixed by agitation, covered, and the TRBC were allowed to settle for 30 minutes at room temperature. The HAI titer was determined by the reciprocal dilution of the last row which contained non-agglutinated TRBC. Positive and negative serum controls were included for each plate. Samples were run in singlet in two independent assays. Results were compared and samples with a >2-fold difference in titer were repeated in a third assay. Geometric mean titers (GMT) were determined on the duplicate results.

2.9 Results

Immune Response of Vaccinated Ferrets

Figure 2:
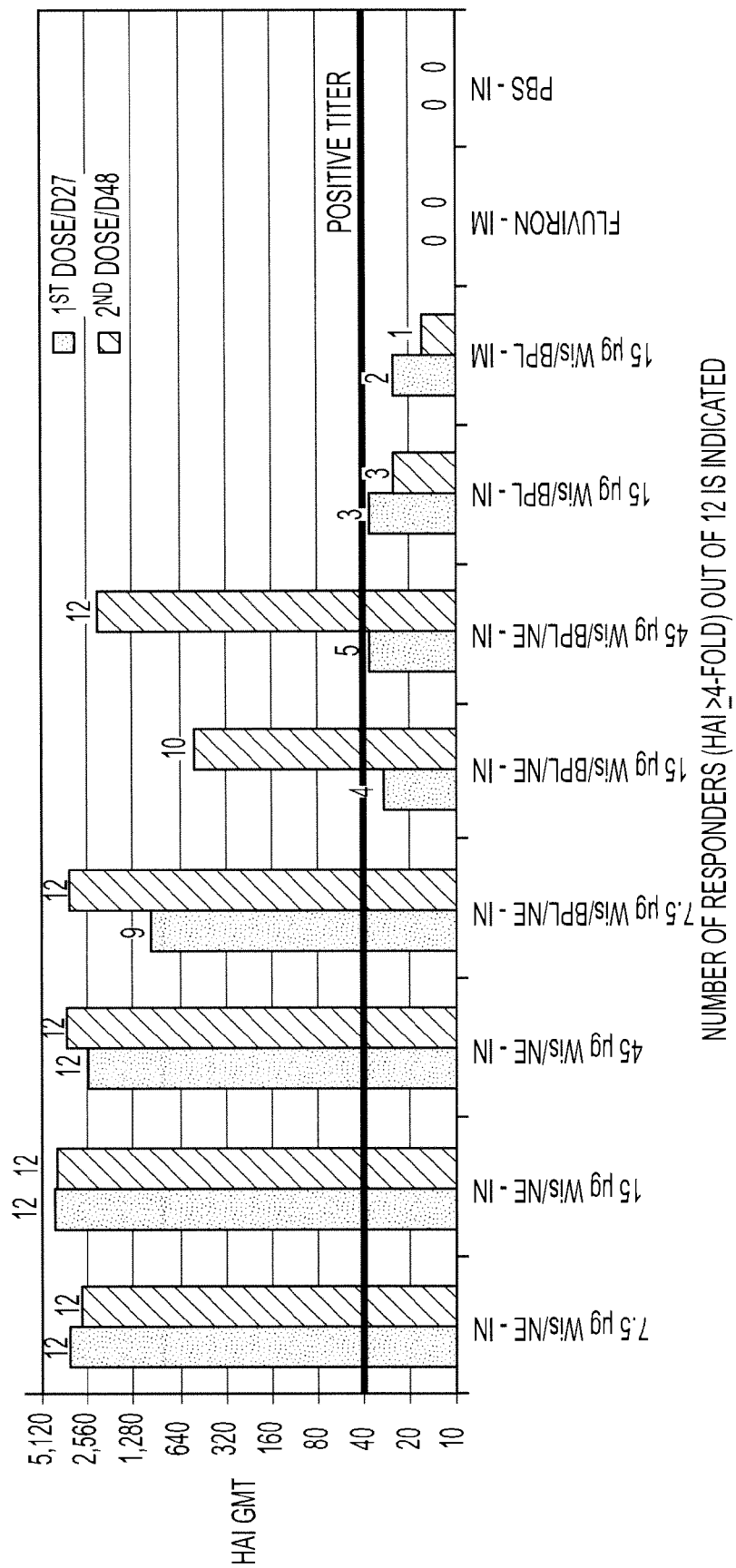
FIG. 2 shows the geometric mean of the inhibitory hemagglutinin antibody titers (HAI) response to the nanoemulsion vaccine compositions described in Example 2 in ferrets following one or two immunizations.
Figure 3:
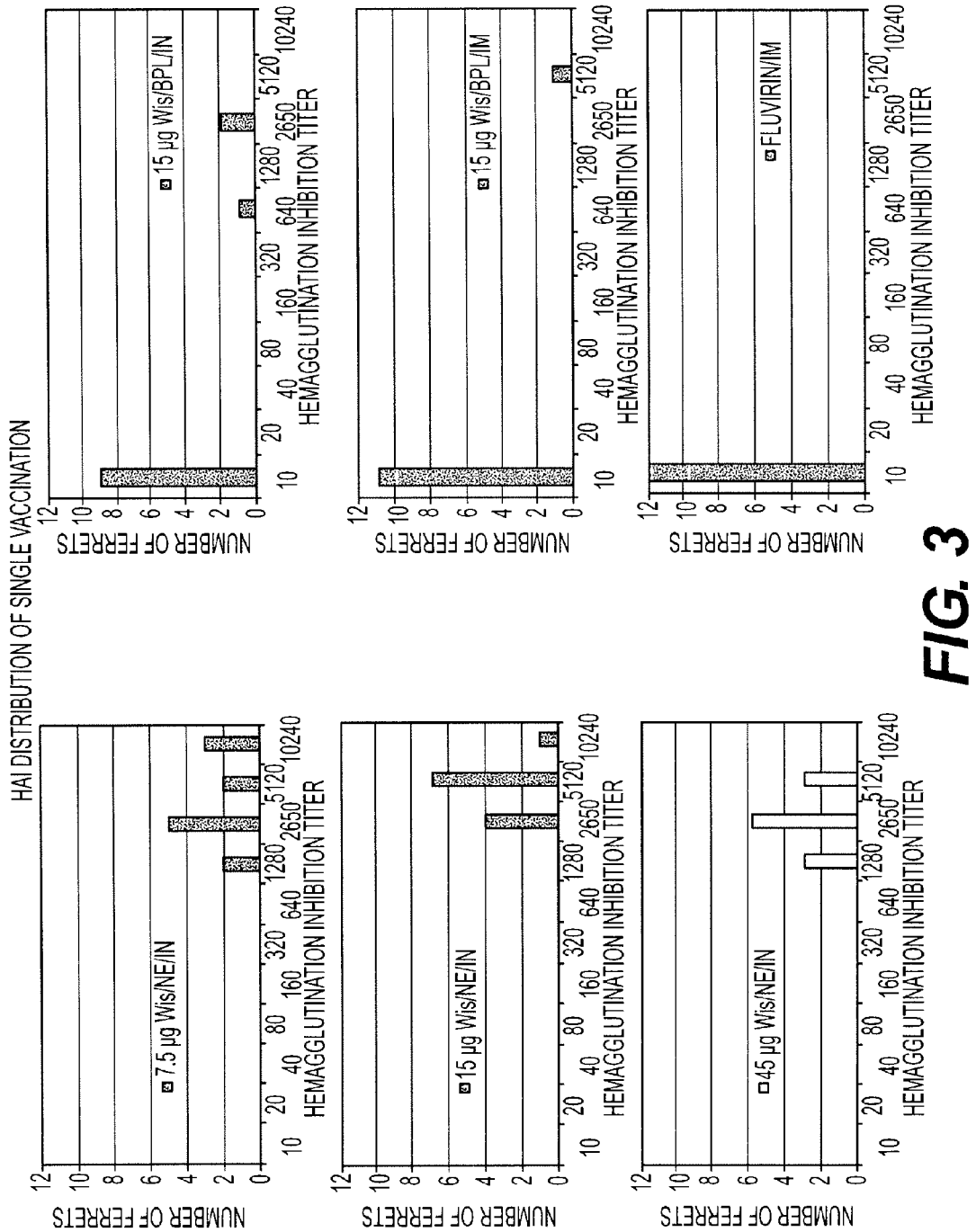
FIG. 3 shows the distribution of HAI in ferrets after a single dose of the nanoemulsion vaccines described in Example 2.
Figure 4:
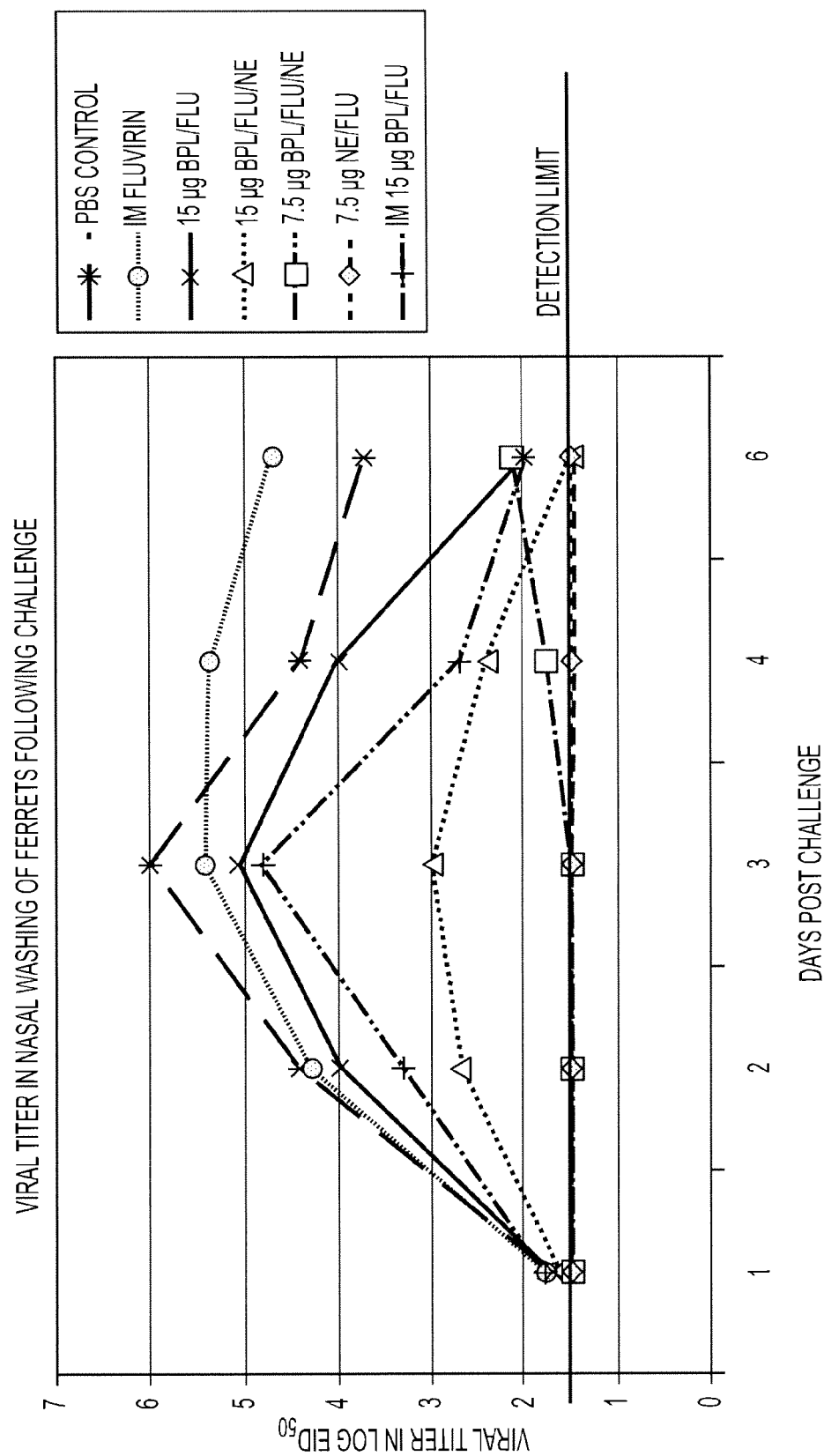
FIG. 4 shows the viral titer in nasal washing of ferrets following challenge by the vaccine compositions described in Example 2.
Figure 5:
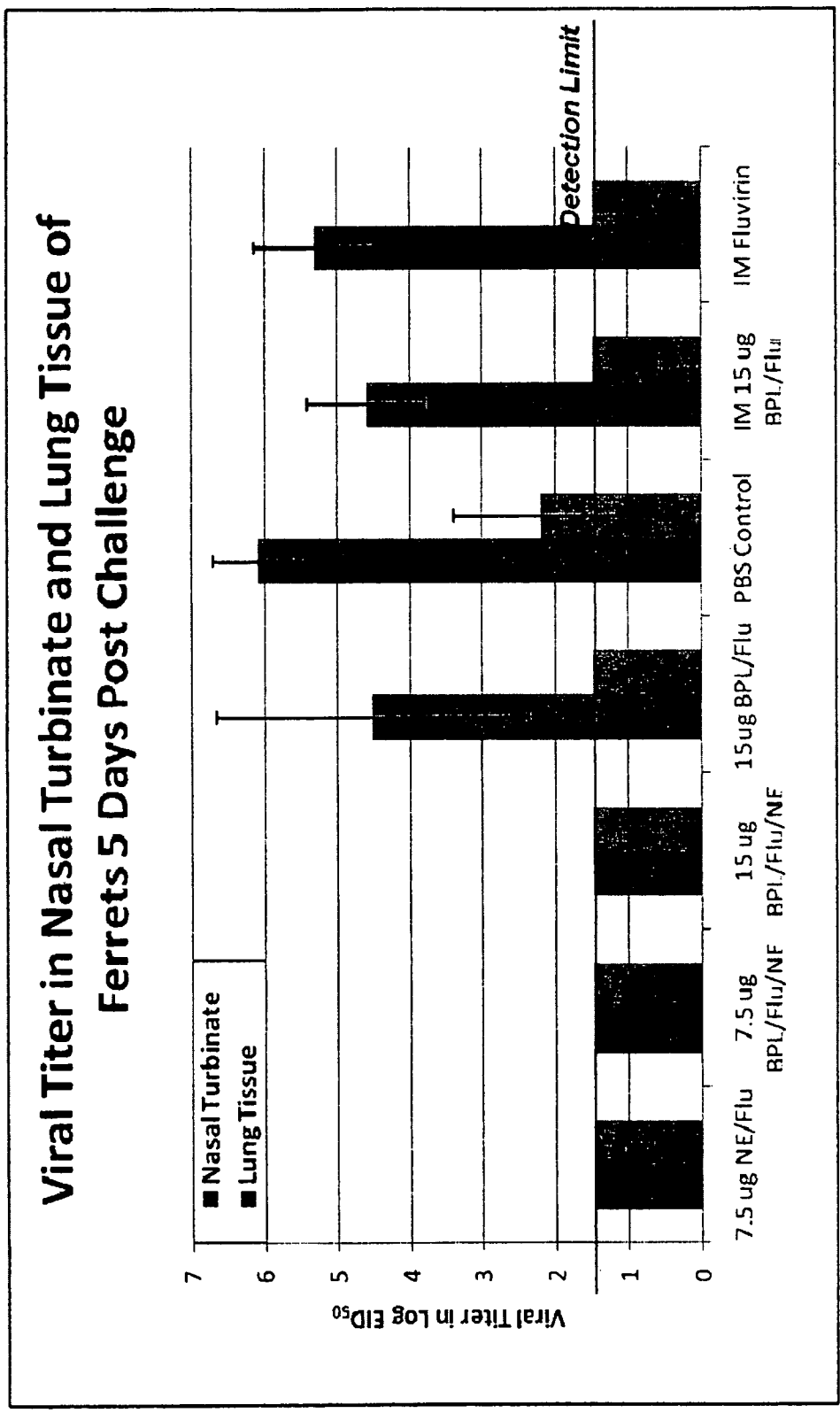
FIG. 5 shows the viral titer in nasal turbinate and lung tissue of ferrets five days post challenge by the vaccine compositions described in Example 2.
Figure 6:
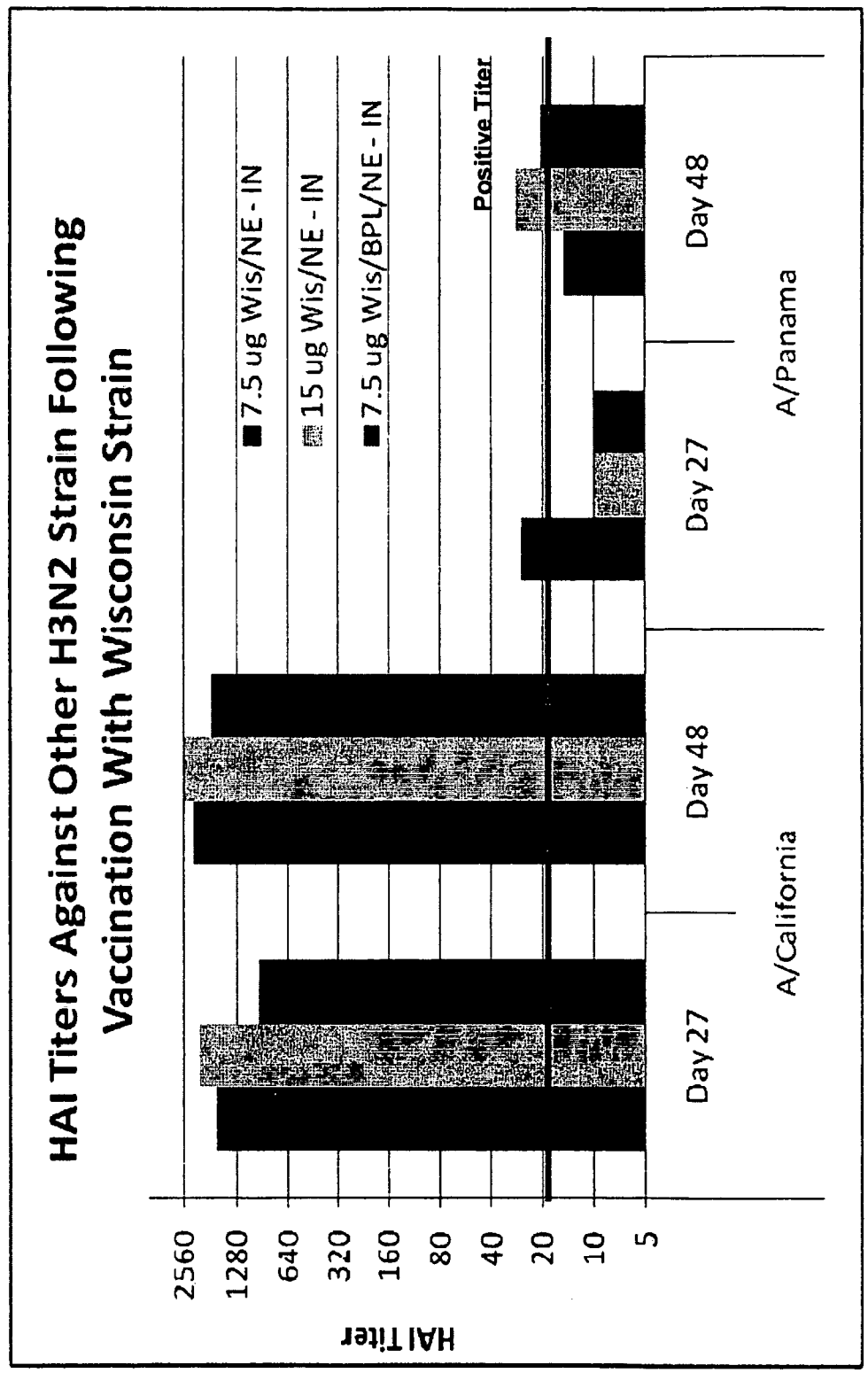
FIG. 6 shows the cross reactivity of the ferrets immunized by the vaccine compositions described in Example 2 against other H3N2 antigens.

The immune response of control and vaccinated ferrets is given in Table 5 and FIGS. 2 and 3.

TABLE 5

Ferret Study #1: Hemagglutination Inhibition (HAI) Geometric Mean Titers (GMT) and Seroconversion Rates Following 1 and 2 Doses of A/Wisconsin/67/2005 (H3N2) Virus, With and Without $W_{80}5EC$-Adjuvant

| Arm # | Vaccine | # of animals/ Arm | Route | Total HA Dose (μg) | Day 27 after 1 dose of vaccine HAI GMT[1] | Day 27 after 1 dose of vaccine Sero-conversion[2] | Day 48 after 2 doses of vaccine HAI GMT | Day 48 after 2 doses of vaccine Sero-conversion |
|---|---|---|---|---|---|---|---|---|
| 1 | $W_{80}5EC$- | 12 | IN[3] | 7.5 | 3620 | 100% | 2727 | 100% |
| 2 | Inactivated | 12 | IN | 15 | 4305 | 100% | 4191 | 100% |
| 3 | Wisconsin Virus | 12 | IN | 45 | 2560 | 100% | 3535 | 100% |
| 4 | βPL- | 12 | IN | 7.5 | 959 | 75% | 3470 | 100% |
| 5 | inactivated | 12 | IN | 15 | 30 | 33% | 528 | 83% |
| 6 | Wisconsin virus + $W_{80}5EC$ | 12 | IN | 45 | 36 | 42% | 2134 | 100% |
| 7 | βPL-inactivated Wisconsin virus | 12 | IN | 15 | 36 | 25% | 25 | 25% |
| 8 | βPL-inactivated Wisconsin virus | 12 | IM[4] | 15 | 25 | 17% | 16 | 8% |
| 9 | Fluvirin ® (βPL-Inactivated) | 12 | IM | 15 | 10 | 0% | 10 | 0% |
| 10 | PBS control | 12 | IN | 0 | 10 | 0% | 10 | 0% |

[1]Geometric Mean Titer to Wisconsin H3N2

[2]Responder defined as HAI >40

[3]IN Intranasal

[4]IM Intramuscular

For $W_{80}5EC$ -Inactivated Wisconsin Virus (7.5 μg), $W_{80}5EC$ -Inactivated Wisconsin Virus (15 μg) and $W_{80}5EC$ -Inactivated Wisconsin Virus (45 μg) given intranasally, 100% of the animals exhibited positive HAI titers 27 days after first immunization. The titers increased or remain constant 21 days post second vaccination. The robustness of the response after a single vaccine in naïve ferrets was unexpected and not usually seen with other vaccine preparations.

For βPL-inactivated Wisconsin virus+$W_{80}5EC$ (7.5 μg), 75% of the animals showed HAI titers 27 days after first vaccination, with all animals responding after the second vaccination. 25% of the ferrets responded when treated with βPL-inactivated Wisconsin virus+$W_{80}5EC$ (15 μg) after the first vaccination while the responders increased to 10/12 ferrets after the second vaccination. When the amount of influenza antigen was 45 μg (βPL-inactivated Wisconsin virus+$W_{80}5EC$), about 40% of the animals responded with positive HAI titers on day 27. One hundred percent of the animals in the latter group exhibited a positive immune response on Day 48 (21 days after second vaccination). As a control for these intranasal vaccinations, βPL inactivated virus without nanoemulsion adjuvant (15 μg) group given intranasally showed significantly less response, with only 25% of the animals responding with low titers after either the first or second vaccination. The commercial vaccine, Fluvirin, when given intramuscularly (IM) did not provoke any immune response after one or two vaccinations. βPL inactivated virus given IM provoked an insignificant response after either vaccination. The control group animals that received PBS also did not exhibit any HAI titers after either vaccination.

Viral Load Determination

Nasal wash samples collected on Days 1, 2, 3, 4, 5 and 6 post challenge were determined for viral load in embroynated eggs.

On Day 54, four animals per group were necropsied and lung and nasal turbinates were collected for viral load determination. FIGS. 4 and 5 show the viral titers in nasal wash samples and in lung and nasal turbinates of animals challenged with H3N2 (A/Wisconsin) virus. The ferrets received vaccine show inhibited virus growth in the nasal wash and in the nasal turbinates.

Cross Reactivity

As shown in FIG. 6, the vaccinated ferrets exhibit cross reactivity against certain H3N2 antigen tested.

Clinical Assessment of Vaccinated Ferrets

The average daily weight change for each group of surviving ferrets relative to baseline weight at the day of challenge was recorded. The change in weight of the control as well as treatment groups was within 4% of their baseline weight during the course of the study. The temperature change of the control and the treated groups varied between +1% and −3% of their original temperature at the day of challenge. No drastic weight or temperature change of the ferrets was observed.

2.10 Summary

An unexpectedly robust immune response to a single intranasal inoculation of nanoemulsion-inactivated influenza virus (Wisconsin strain) was seen in naïve ferrets, even when the dose of influenza antigen was two-fold lower than most commercial seasonal vaccines. Not only were the HAI titers high, all animals receiving the nanoemulsion-inactivated vaccine seroconverted. When the nanoemulsion was mixed with βPL-inactivated influenza antigen, the best response after a single vaccination was seen with the lowest amount of antigen, 7.5 µg. A second vaccination with βPL-inactivated influenza antigen boosted nearly all the ferrets to high HAI titers, signifying the potential of the nanoemulsion to act as an adjuvant to even dose-sparing amounts of βPL-inactivated influenza antigen. The immune response resulting from nanoemulsion inactivation of virus represents a potential paradigm shift in vaccinology.

Example 3

Efficacy of Nanoemulsion Influenza Vaccine in Animal Model

The goal of this study was to ascertain if the efficacy of commercial seasonal influenza vaccines with nanoemulsion adjuvant protects against subsequent infection by H3N2 in a ferret model.

Ferret Study #2

Ferret study #2 was designed to examine immune responses to increasing total HA antigen doses of 7.5, 22.5 and 36 µg mixed with 20% $W_{80}5EC$ after one and two doses. HAI titers to A/Wisconsin (H3N2), A/Solomon Islands (H1N1) and B/Malaysia contained in the commercial Fluvirin® and Fluzone® (2007-2008) vaccines were evaluated (Table 6).

TABLE 6

Ferret Study #2: Design

| | | # Ferrets/Arm | | | |
|---|---|---|---|---|---|
| Vaccine | Route | 45 µg total HA | 36 µg total HA | 22.5 µg total HA | 7.5 µg total HA |
| Fluvirin ® + 20% $W_{80}5EC$ | IN | | 9 | 10 | 10 |
| Fluvirin ® | IN | | 9 | | |
| Fluvirin ® | IM | 9 | | | |
| Fluzone ® + 20% $W_{80}5EC$ | IN | | 10 | 10 | 10 |
| Fluzone ® | IN | | 9 | | |
| Fluzone ® | IM | | | 9 | |
| PBS control | IN | | | 9 | |

3.1 Animals:

The ferrets were prepared and handled according to essentially the same protocol as described in Example 2, section 2.1.

3.2 Treatment (Dosing) and Blood Collection:

The formulations were stored at 4° C. prior to use. Eleven groups of ferrets (N=9 or 10/group) were treated on days 0 and 28. The treatment schedule was as given in Table 7 below:

TABLE 7

Dosing of ferrets with test article

| Dose Group | Article Administered | Dose Route | Total HA Dose Level (µg) | Treatment Dose Volume (µL/nare) | Challenge Dose Volume (mL/nare) | # Animals |
|---|---|---|---|---|---|---|
| 1 | Fluvirin ® + 20% $W_{80}5EC$ | IN | 36 | 250 | 0.5 | 9 |
| 2 | Fluvirin ® + 20% $W_{80}5EC$ | IN | 22.5 | 250 | 0.5 | 10 |
| 3 | Fluvirin ® + 20% $W_{80}5EC$ | IN | 7.5 | 250 | 0.5 | 10 |
| 4 | Fluvirin ® | IM | 36 | 250 | 0.5 | 9 |
| 5 | Fluvirin ® | IM | 45 | 250/thigh | 0.5 | 9 |
| 6 | Fluzone ® + 20% $W_{80}5EC$ | IN | 36 | 250 | 0.5 | 10 |
| 7 | Fluzone ® + 20% $W_{80}5EC$ | IN | 22.5 | 250 | 0.5 | 10 |
| 8 | Fluzone ® + 20% $W_{80}5EC$ | IN | 7.5 | 250 | 0.5 | 10 |
| 9 | Fluzone ® | IN | 36 | 250 | 0.5 | 9 |
| 10 | Fluzone ® | IM | 45 | 250/thigh | 0.5 | 9 |
| 11 | PBS | IN | 0 | 250 | 0.5 | 9 |

Fluvirin® and Fluzone® are commercial influenza vaccines. The influenza antigens present in the vaccines change each flu seasons.

Fluzone® is a licensed commercial vaccine manufactured by sanofi pasteur and is approved for intramuscular (IM) administration in the U.S. The vaccine is available in a single dose or multi-dose presentation. Each 0.5 mL dose contains a total of 45 µg of influenza virus hemagglutinin (HA) from each of the following 3 strains: (A/Solomon Islands/3/2006 (H1N1), A/Wisconsin/67/2005 (H3N2), and B/Malaysia/2506/2004.

Fluvirin® is a licensed commercial vaccine manufactured by Novartis Vaccines and is approved for intramuscular (IM) administration in the U.S. The vaccine is available in a single dose or multi-dose presentation. Each 0.5 mL dose contains a total of 45 µg of influenza virus hemagglutinin (HA), from each of the following 3 strains: A/Solomon Islands/3/2006 (H1N1), A/Wisconsin/67/2005 (H3N2), and B/Malaysia/2506/2004.

Prior to blood collection, animals were anesthetized and blood was collected on Day 12 (prior to vaccination), Day 27 (prior to revaccination), Day 48 (prior to challenge), and Day 63 (post challenge).

3.3 Challenge and Monitoring of Ferrets:

The A/Wisconsin/67/2005 strain was chosen as the challenge strain. On Day 49 ferrets were challenged with $10^7$ $EID_{50}$/mL of A/Wisconsin/67/2005. At the time of challenge, ferrets were first anesthetized I, followed by intranasal (I.N.) administration of virus with a total of $1 \times 10^7$ $EID_{50}$/mL of A/Wisconsin/67/2005 in a volume of 1.0 ml PBS, delivered to the nostrils (0.5 ml/nostril) according to standard procedures.

Ferrets were examined daily for clinical signs of infection including weight loss, change in temperature, nasal and ocular discharge, dyspnea, neurological signs. In this study, the animals were observed twice daily for morbidity and mortality. In addition, clinical signs, body weights and body temperatures were evaluated weekly.

3.4 Collection of Ferret Nasal Wash, Lungs, Nasal Turbinate and Lung Samples:

Ferrets were sedated and weighed. Nasal wash (NW) samples were collected by flushing the nares with PBS, 1% BSA and antibiotic solution (0.5 ml/nare), allowing the ferret to sneeze into a Petri dish and collection of the expelled PBS solution on Days 2-5, 27, 30-33, from group 1 and day 48 before challenge and days 50-55(from all groups of animals) and processed according to standard procedures. Nasal washes were collected in tubes, placed on dry ice and subsequently stored at ≤−70° C. until viral load determination was done in embroynated eggs.

On Day 53, three or four animals per group were necropsied and lung and nasal turbinates were collected and stored at −80° C. until viral load determination was done in embroynated hens' eggs.

3.5 Hemagglutination Inhibition Determination in Serum Samples of Vaccinated Animals:

The experiment was performed according to the procedure described in Example 2, section 2.6.

3.6 Viral Load Determination in Nasal Wash Samples:

The protocol described in Example 2, section 2.7 was followed, except that the embryonated chicken eggs were incubated for approximately 48 hours at 33° C. without $CO_2$ following inoculation.

3.7 Cross Reactivity with Other Antigens:

Vaccinated ferrets were tested for antibody titers against A/Wisconsin after one and two vaccinations, A/Solomon Islands and B/Malaysia after one vaccination, or with five H3N2 antigens, A/California, A/New York, A/Wyoming, A/Wellington and A/Panama after two vaccinations.

3.8 Results

Clinical Assessment of Vaccinated Ferrets

The average daily weight change for each group of surviving ferrets relative to baseline weight at the day of challenge was recorded. The change in weight of the control as well as treatment groups was within 4-5% of their baseline weight during the course of the study. The temperature change of the control and the treated groups varied between +2.5% and −2.5% of their original temperature at the day of challenge. No drastic weight or temperature change of the ferrets was observed.

Immune Response of Vaccinated Ferrets

Figure 7:
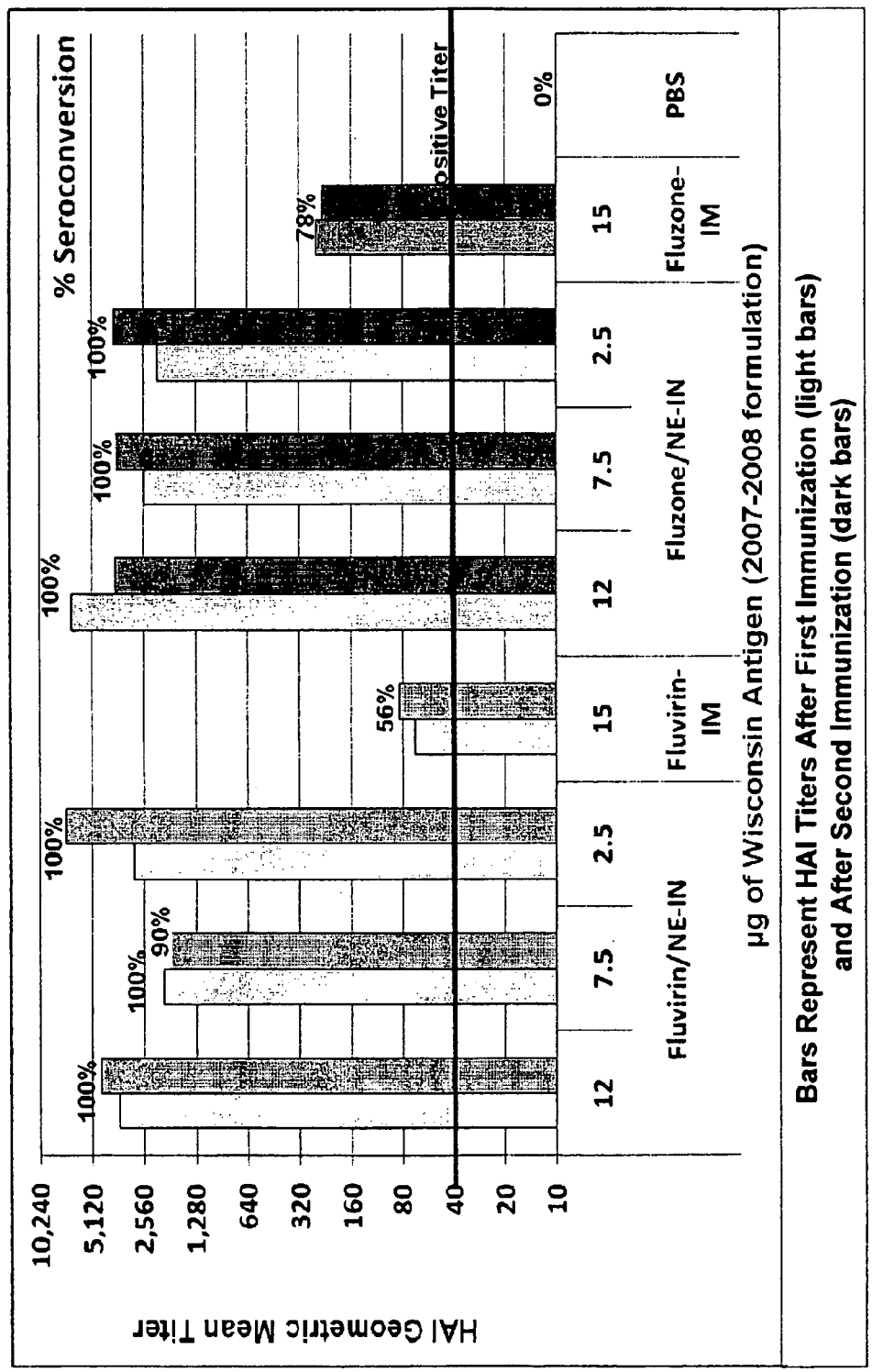
FIG. 7 shows the geometric mean HAI titer against Wisconsin antigen in response to the nanoemulsion vaccine described in Example 3 in ferrets following one- or two-immunizations.

The immune response of control and vaccinated ferrets to the Wisconsin antigen present in Fluvirin® and Fluzone® is given in FIG. 7. The "Positive Titer" line in FIG. 7 denotes the titer at which protection is exhibited. Thus, above the "Positive Titer" line protection against the listed strain is observed, and below the "Positive Titer" line no protection against the listed strain is observed. Doses of $W_{80}5EC$-adjuvanted commercial vaccines as low as 7.5 µg total HA antigen resulted in geometric mean titers (GMT)>2200 for A/Wisconsin (H3N2) following a single vaccination in naïve male ferrets (Table 8). This represents a >220-times increase from baseline and a 32-times increase compared to Fluvirin® IM and >8-times increase compared to Fluzone® IM. Notably, all ferrets given Fluvirin® or Fluzone®+20% $W_{80}5EC$ responded with HAI titers >40 (Table 8).

TABLE 8

Ferret Study #2: A/Wisconsin (H3N2) HAI Titers and Seroconversion in Ferrets Following a Single Intranasal Dose of Commercial Vaccines ± 20% $W_{80}5EC$-Adjuvant

| Treatment | Route/N | Total Antigen Dose (µg HA) | GMT[1] | Responders[2] | Hemagglutination Inhibition Titer Ranges Min | Max |
|---|---|---|---|---|---|---|
| Fluvirin® + 20% $W_{80}5EC$ | IN[3]/9 | 36 | 4064 | 100% | 2560 | 10240 |
| Fluvirin® + 20% $W_{80}5EC$ | IN/10 | 22.5 | 2255 | 100% | 240 | 10240 |
| Fluvirin® + 20% $W_{80}5EC$ | IN/10 | 7.5 | 2976 | 100% | 480 | 20480 |
| Fluvirin® | IN/9 | 36 | 710 | 89% | 10 | 5120 |
| Fluvirin® | IM[4]/9 | 45 | 68 | 56% | 10 | 960 |
| Fluzone® + 20% $W_{80}5EC$ | IN/10 | 36 | 7241 | 100% | 2560 | 20480 |
| Fluzone® + 20% $W_{80}5EC$ | IN/10 | 22.5 | 2776 | 100% | 960 | 10240 |
| Fluzone® + 20% $W_{80}5EC$ | IN/10 | 7.5 | 2217 | 100% | 960 | 10240 |
| Fluzone® | IN/9 | 36 | 669 | 78% | 10 | 10240 |
| Fluzone® | IM/9 | 45 | 257 | 78% | 10 | 40960 |
| PBS | IN/9 | 0 | 10 | 0% | 10 | 15 |

[1]Geometric Mean Titer to Wisconsin H3N2
[2]Responder defined as HAI >40
[3]IN Intranasal
[4]IM Intramuscular In study #2, HAI titers to antigens for A/Solomon Islands (H1N1) and B/Malaysia contained in the $W_{80}5EC$-adjuvanted commercial vaccines were also determined and demonstrated ≈100-times increase and ≥25-times increase relative to baseline, respectively. In addition, for Solomon Islands there was a >40-times increase in the adjuvanted arm compared to Fluvirin® IM and >13-times increase compared to Fluzone® IM. For B/Malaysia there was a >11-times increase compared to Fluvirin® IM and a >7 times increase compared to Fluzone® IM (Table 9).

TABLE 9

Ferret Study #2: HAI Titers and Seroconversion to the Three Influenza Vaccine Strains in Ferrets Following a Single Intranasal Dose of Commercial Vaccines ± 20% $W_{80}5EC$-Adjuvant

| Treatment | Route/N | Total Antigen Dose (µg HA) | Solomon Islands (H1N1) GMT[1] | %[2] | isconsin H3N2 GMT | % | /Malaysia GMT | % |
|---|---|---|---|---|---|---|---|---|
| Fluvirin® + 20% $W_{80}5EC$ | IN[3]/9 | 36 | 1314 | 100% | 4064 | 100% | 686 | 100% |

TABLE 9-continued

Ferret Study #2: HAI Titers and Seroconversion to the Three Influenza Vaccine Strains in Ferrets Following a Single Intranasal Dose of Commercial Vaccines ± 20% $W_{80}5EC$-Adjuvant

| Treatment | Route/N | Total Antigen Dose (µg HA) | Solomon Islands (H1N1) GMT[1] | %[2] | isconsin H3N2) GMT | % | /Malaysia GMT | % |
|---|---|---|---|---|---|---|---|---|
| Fluvirin® + 20% $W_{80}5EC$ | IN/10 | 22.5 | 1405 | 100% | 2255 | 100% | 297 | 100% |
| Fluvirin® + 20% $W_{80}5EC$ | IN/10 | 7.5 | 927 | 100% | 2976 | 100% | 244 | 100% |
| Fluvirin® | IN/9 | 36 | 388 | 100% | 710 | 89% | 69 | 78% |
| Fluvirin® | IM[4]/9 | 45 | 20 | 22% | 68 | 56% | 22 | 33% |
| Fluzone® + 20% $W_{80}5EC$ | IN/10 | 36 | 3559 | 100% | 7241 | 100% | 694 | 100% |
| Fluzone® + 20% $W_{80}5EC$ | IN/10 | 22.5 | 2154 | 100% | 2776 | 100% | 383 | 100% |
| Fluzone® + 20% $W_{80}5EC$ | IN/10 | 7.5 | 2417 | 100% | 2217 | 100% | 463 | 100% |
| Fluzone® | IN/9 | 36 | 441 | 100% | 669 | 78% | 71 | 78% |
| Fluzone® | IM/9 | 45 | 152 | 89% | 257 | 78% | 50 | 67% |
| PBS | IN/9 | 0 | 10 | % | 10 | 0% | 10 | 0% |

Figure 8:
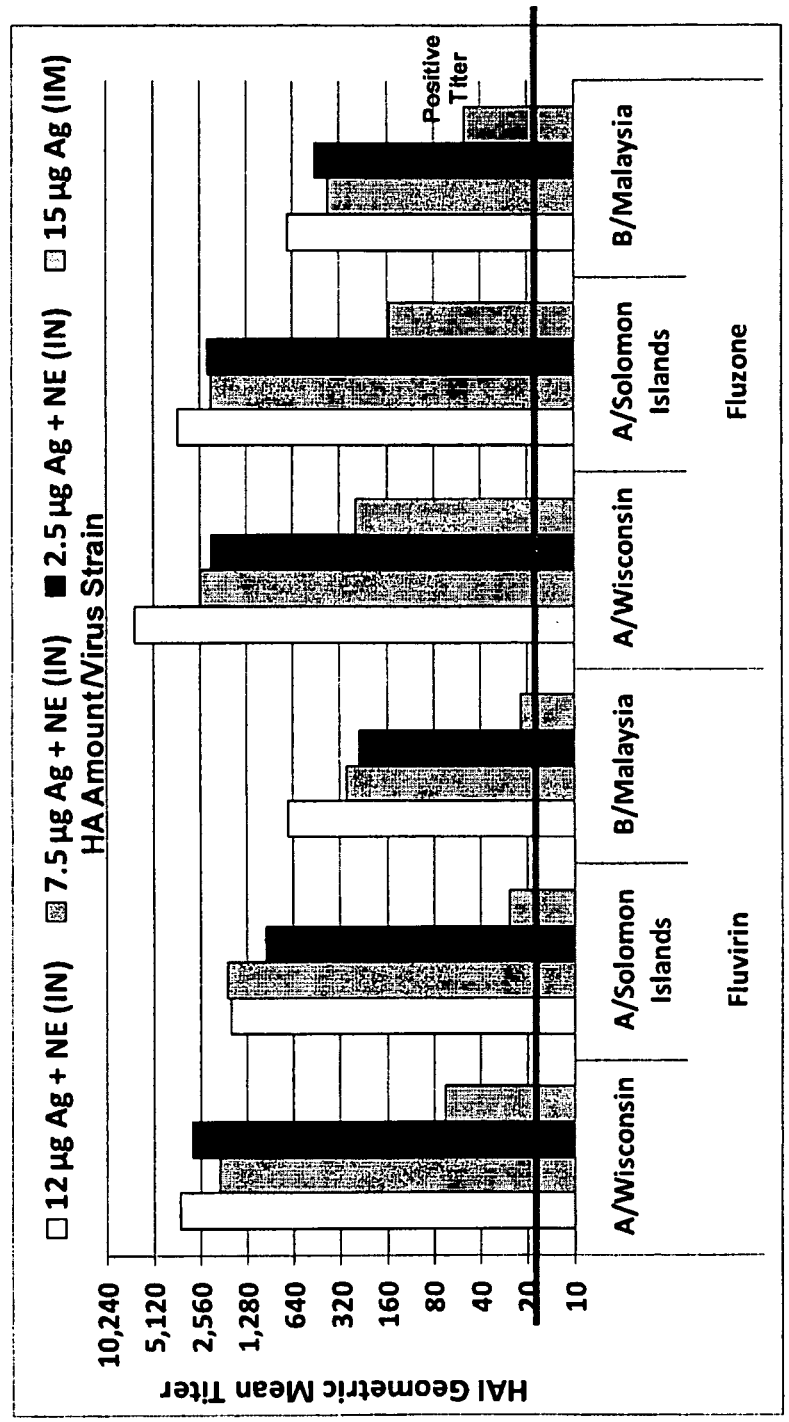
FIG. 8 shows the HAI titers against Wisconsin, A/Solomon Islands and B/Malaysia antigen in ferrets immunized with the vaccine as described in Example 3.

[1]Geometric Mean Titer
[2]% seroconversion defined as HAI >40
[3]IN Intranasal
[4]IM Intramuscular In ferret study #2, HAI titers to H3N2 strains not contained in the commercial vaccines were determined on Day 48 following two intranasal vaccine doses (Day 0 and Day 28) and are summarized in Table 10 and FIG. 8. The 20% $W_{80}5EC$-adjuvanted vaccines elicited 25-times to 720-times increases from baseline HAI titers and significant (≥70%) seroconversion to all strains tested for Fluvirin®+20% $W_{80}5EC$ and all strains except Wellington and Panama in animals receiving Fluzone®+20% $W_{80}5EC$. The IM control groups had significantly lower rates of seroconversion.

strain. These ferrets did not show evidence of virus in their nasal washes on days 2-6 following the challenge.

Cross Reactivity

Figure 9:
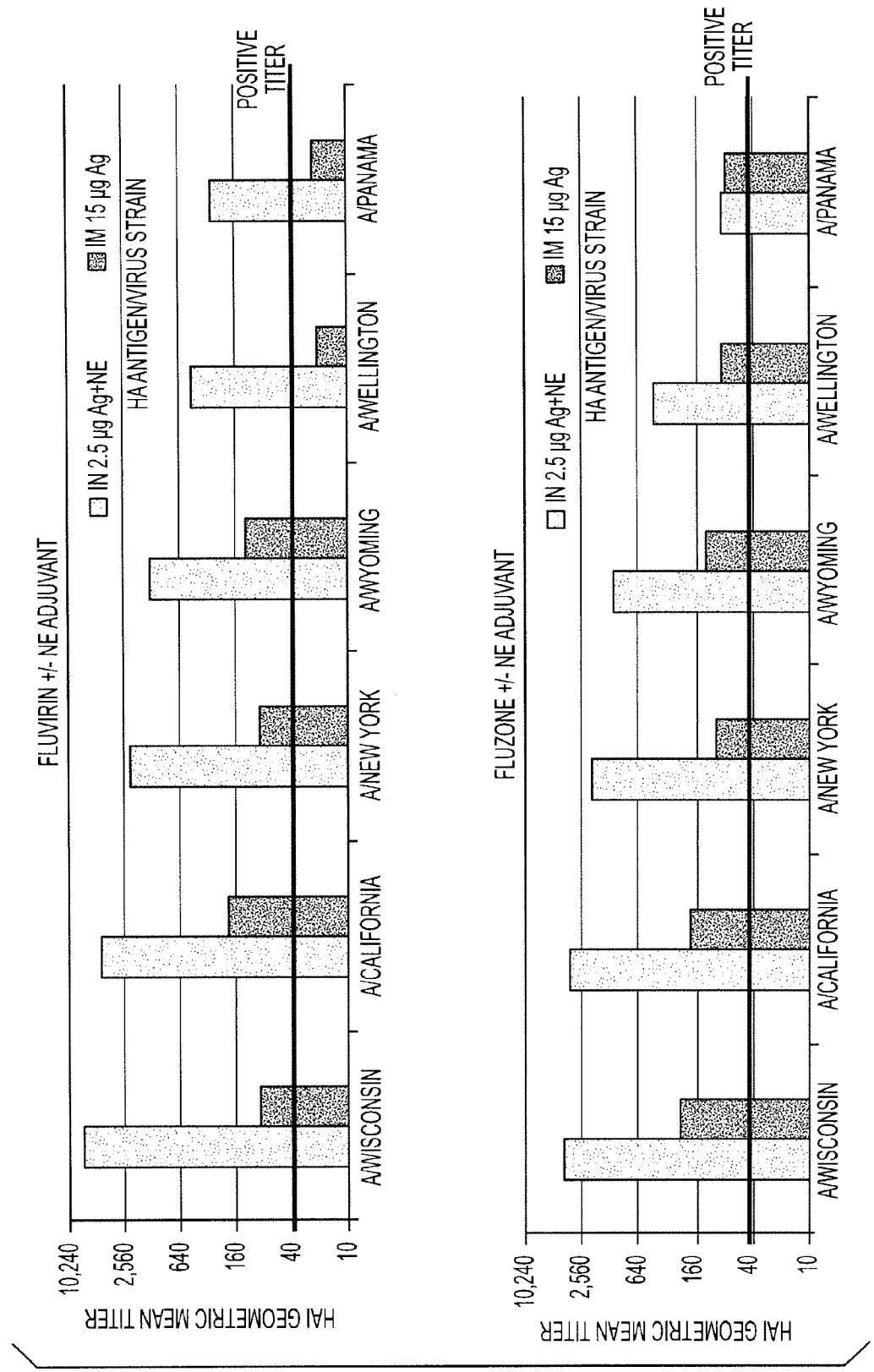
FIG. 9 shows the cross reactivity of ferrets immunized with the vaccine as described in Example 3 against other influenza A virus strains following two immunizations.

As shown in FIG. 9, the ferrets immunized with a small dose of the NE-adjuvanted vaccine exhibit cross reactivity against all the H3N2 strain tested (A/California, A/NewYork, A/Wyoming, A/Wellington and A/Panama). HAI titers were higher compared with the IM vaccine. Antigen sparing was observed with the NE-adjuvanted vaccine compared with the

TABLE 10

Ferret Study #2: HAI Titers and Seroconversion to Wisconsin and Other H3N2 Influenza Strains Following Two Intranasal Doses of Commercial Vaccines ± 20% $W_{80}5EC$-Adjuvant (Day 48)

| Treatment | Route | Total Antigen Dose (µg HA) | Wisconsin GMT[1] | % | Wyoming GMT | % | California GMT | % | Wellington GMT | % | New York GMT | % | Panama GMT | % |
|---|---|---|---|---|---|---|---|---|---|---|---|---|---|---|
| Fluvirin® + 20% $W_{80}5EC$ | IN[2] | 7.5 | 7288 | 100% | 1386 | 90% | 4510 | 100% | 253 | 70% | 1370 | 100% | 311 | 90% |
| Fluvirin® | IM[3] | 45 | 84 | 44% | 127 | 56% | 195 | 56% | 16 | 11% | 79 | 44% | 15 | 11% |
| Fluzone® + 20% $W_{80}5EC$ | IN | 7.5 | 3835 | 100% | 1085 | 90% | 3418 | 100% | 54 | 40% | 1405 | 100% | 56 | 50% |
| Fluzone® | IM | 45 | 238 | 44% | 129 | 44% | 198 | 56% | 50 | 33% | 54 | 33% | 77 | 44% |

[1]Geometric Mean Titer
[2]IN Intranasal
[3]IM Intramuscular
[4]% seroconversion defined as HAI >40

In addition, in study #2, ferrets that received 7.5 total µg HA antigen (Fluzone® or Fluvirin®) with 20% $W_{80}5EC$ were challenged with $10^7$ $EID_{50}$ of A/Wisconsin (H3N2) IM non-adjuvanted vaccine. The "Positive Titer" line in FIG. 9 denotes the titer at which protection is exhibited. Thus, above the "Positive Titer" line protection against the listed strain is observed, and below the "Positive Titer" line no protection against the listed strain is observed.

3.9 Summary

Intranasal vaccination with nanoemulsion adjuvanted commercial vaccine in naive ferrets resulted in an unexpectedly robust immune response to a single intranasal dose, even when the dose of influenza antigen was six-fold lower than most commercial seasonal vaccines. Not only were the HAI titers high, all animals receiving the nanoemulsion-inactivated vaccine seroconverted. A higher immune response was observed when the nanoemulsion was used to inactivate influenza virus, the best response after a single vaccination was seen with the lowest amount of antigen, 2.5 µg/subtype. A second vaccination with NE-adjuvanted influenza vaccine boosted nearly all the ferrets to high HAI titers, signifying the potential of the nanoemulsion to act as an adjuvant to even dose-sparing amounts of influenza antigen. The immune response resulting from nanoemulsion inactivation of virus represents a potential paradigm shift in vaccinology.

This vaccination using nanoemulsion adjuvanted commercial vaccine resulted in high cross reactivity against the H3N2 subtypes tested (California, New York, Wyoming, Wellington and Panama). This would indicate that the NE-adjuvanted influenza vaccine will not result in protection of only the vaccinated strain but they had a big potential to extend the protection to other strains not incorporated in the administered vaccine.

Example 4

Efficacy of Nanoemulsion Influenza Vaccine in Combination of a Commercial Vaccine in Animal Model The goal of this study was to determine the efficacy of a nanoemulsion influenza vaccine in combination of a commercial vaccine, Fluzone® (2007-2008), in a ferret model.

Ferret Study #3

Ferret study #3 was designed to further explore antigen-sparing activity and cross-reactivity following a single intranasal 20% $W_{80}5EC$-adjuvanted vaccine dose.

4.1 Animals:

The ferrets were prepared and handled according to essentially the same protocol as described in Example 2, section 2.1. The animals were observed twice daily for morbidity and mortality and no abnormal observations or altered activity was noted. In addition, clinical signs, body weights and body temperatures were evaluated weekly 4.2 Treatment (Dosing):

The formulations were stored at 4° C. prior to use. Four groups of ferrets (N=6/group) were treated on days 0 and 28. The treatment schedule was as given in Table 11 below:

TABLE 11

Dosing of ferrets with test article

| Dose Group | Vaccine Material | Immunization Route | Immunization Dose (µg) | Immunization Volume | # Animals |
|---|---|---|---|---|---|
| 1 | Fluzone ® + 20% $W_{80}5EC$ | IN | 7.5 | 0.25 mL/nare | 6 |
| 2 | Fluzone ® + 20% $W_{80}5EC$ | IN | 3 | 0.25 mL/nare | 6 |
| 3 | Fluzone ® + 20% $W_{80}5EC$ | IN | 0.9 | 0.25 mL/nare | 6 |
| 4 | Fluzone ® | IM | 45 | 0.5 mL | 6 |

4.3 Preparation and Characterization of Influenza Virus for Challenge:

Stock viruses received from the Centers for Disease Control and Prevention and amplified in embryonated chicken eggs according to standard protocol. The influenza virus was prepared and characterized according to the same protocol described in Example 2, section 2.3. For challenge, the virus was adjusted to $10^7$ $EID_{50}$/mL.

4.4 Challenge and Monitoring of Ferrets:

On Day 28 ferrets were challenged with $10^7$ $EID_{50}$/mL of A/Wisconsin/67/2005. At the time of challenge, ferrets were first anesthetized, followed by intranasal (I.N.) administration of virus with a total of $1 \times 10^7$ $EID_{50}$/mL of A/Wisconsin/67/2005 in a volume of 1.0 ml PBS, delivered to the nostrils (0.5 ml/nostril) according to standard procedures.

Ferrets were examined daily for clinical signs of infection including weight loss, change in temperature, nasal and ocular discharge, dyspnea, neurological signs.

4.6 Hemagglutination Inhibition Determination in Serum Samples of Vaccinated Animals:

The experiment was performed according to the procedure described in Example 2, section 2.6.

4.8 Cross Reactivity with Other Antigens:

Vaccinated ferrets were tested for antibody titers against A/New York, A/California, A/Wyoming, A/Wellington and A/Panama after only one vaccination.

4.9 Results

Immune Response of Vaccinated Ferrets

Figure 10:
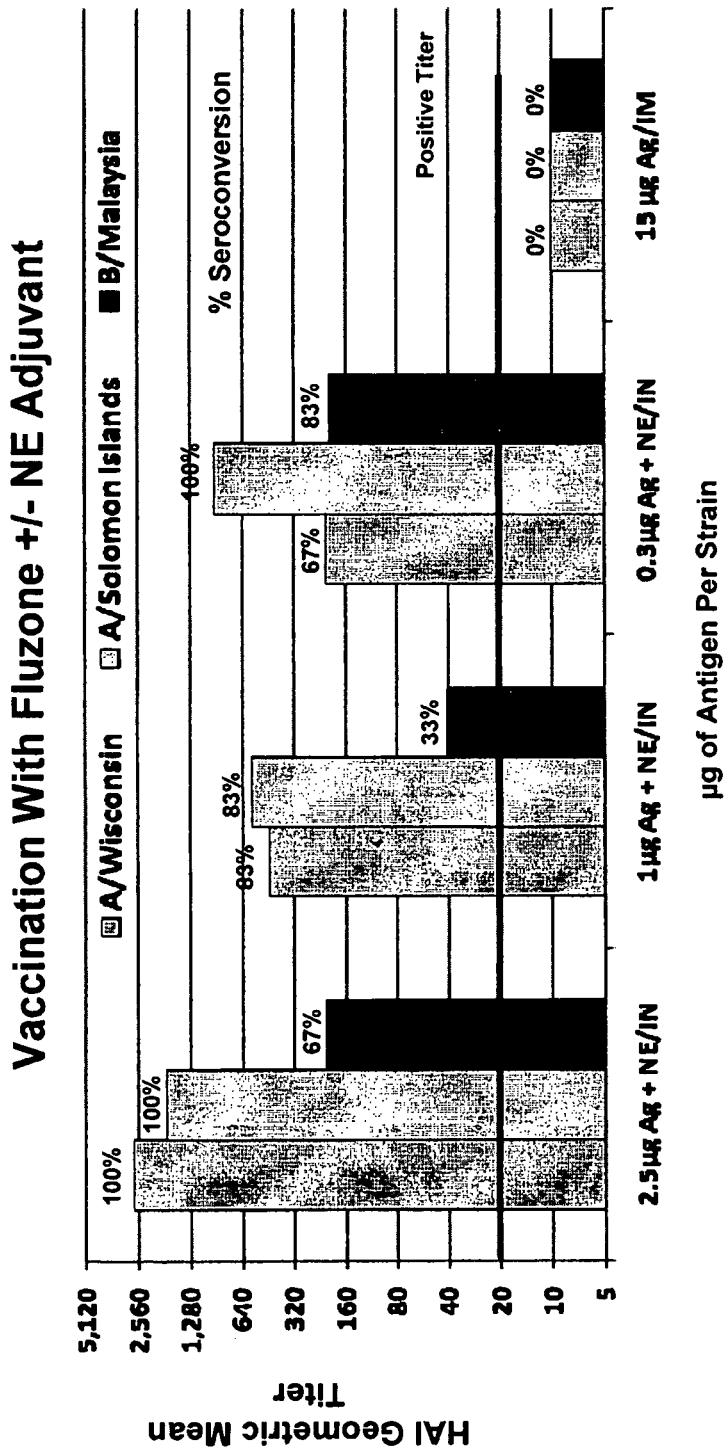
FIG. 10 shows the geometric mean HAI titer response to the nanoemulsion vaccine described in Example 4 in ferrets following a single dose vaccination.

The immune response of control and vaccinated ferrets is given in FIG. 10. The vaccine produced high HAI titers after only one immunization and demonstrated a significant dose-sparing effect. Positive titers were achieved with approximately ⅟₅₀ of the commercial antigen dose adjuvanted with NE. The "Positive Titer" line in FIG. 10 denotes the titer at which protection is exhibited. Thus, above the "Positive Titer" line protection against the listed strain is observed, and below the "Positive Titer" line no protection against the listed strain is observed.

The lowest total antigen dose from study #2 (7.5 µg total antigen) was replicated and antigen-sparing activity was assessed by administration of lower doses of 3 and 0.9 µg total antigen. All 20% $W_{80}5EC$-adjuvanted commercial vaccine doses elicited immune responses that were significantly enhanced when compared to an intramuscular control that received 37.5 µg Fluzone® (Table 12).

TABLE 12

Ferret Study #3: HAI Titers and Seroconversion to the Three Influenza Vaccine Strains in Ferrets Following a Single Intranasal Dose of Commercial Vaccine Fluzone ® (2007-2008) ± 20% $W_{80}5EC$-Adjuvant

| Treatment | Route | Total Antigen Dose (µg HA) | A/Solomon Islands (H1N1) | | A/Wisconsin (H3N2) | | B/ Malaysia | |
|---|---|---|---|---|---|---|---|---|
| | | | GMT[1] | %[2] | GMT | % | GMT | % |
| Fluzone ® + 20% $W_{80}5EC$ | IN[3] | 7.5 | 1725 | 100 | 2663 | 100 | 206 | 67 |
| Fluzone ® + 20% $W_{80}5EC$ | IN | 3 | 554 | 83 | 440 | 83 | 40 | 33 |
| Fluzone ® + 20% $W_{80}5EC$ | IN | 0.9 | 905 | 100 | 206 | 67 | 196 | 83 |
| Fluzone ® | IM[4] | 37.5 | 10 | 0 | 10 | 0 | 10 | 0 |

Figure 11:
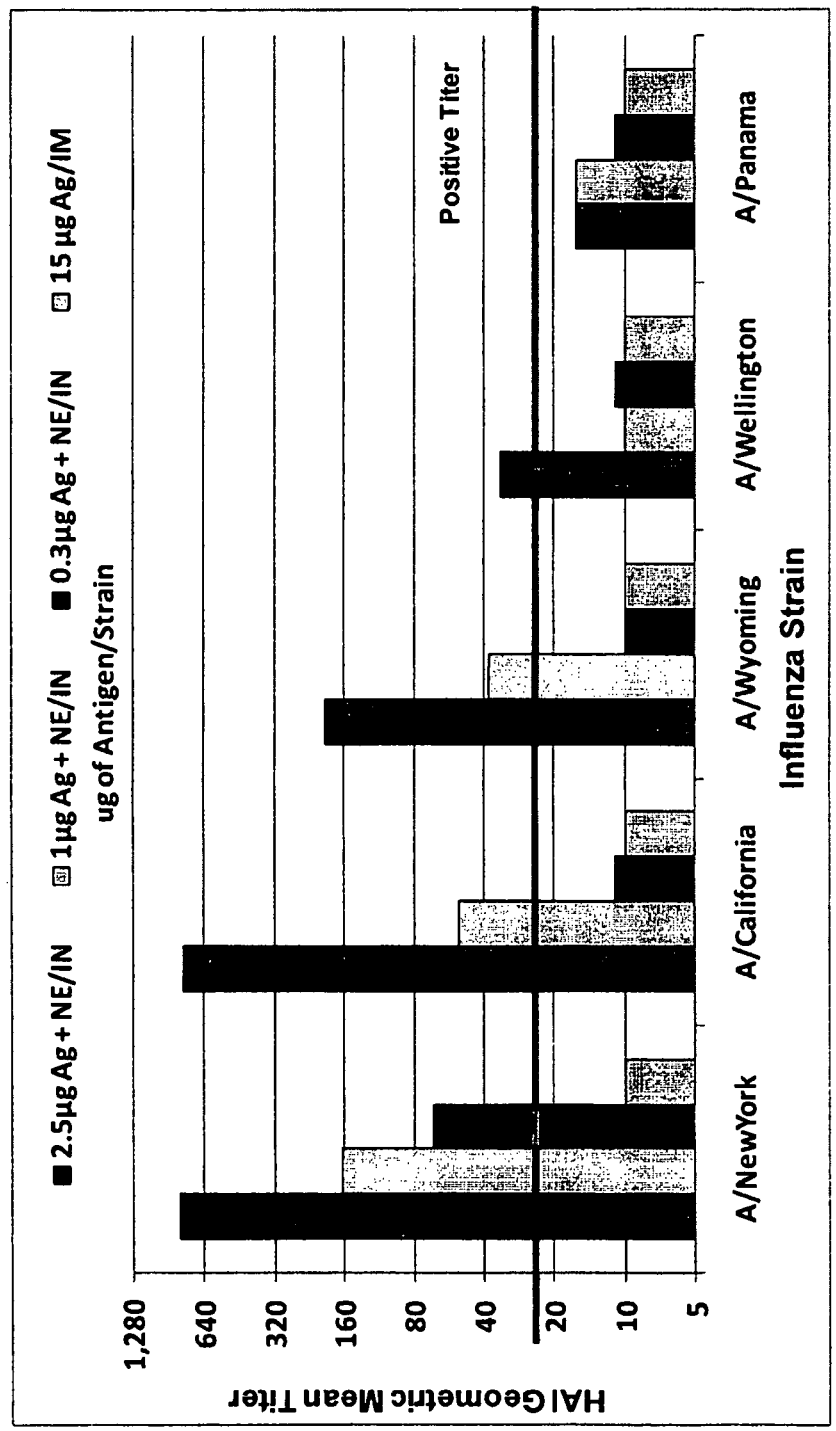
FIG. 11 shows the cross reactivity of ferrets immunized with the vaccine as described in Example 4 against other influenza virus strains following two vaccinations.

[1]Geometric Mean Titer
[2]% seroconversion defined as HAI >40
[3]Intranasal
[4]Intramuscular Cross Reactivity In ferret study #3, HAI titers for A/Wisconsin and other H3N2 influenza strains not contained in the commercial vaccine were determined and robust immune responses at a total antigen dose of 7.5 µg were demonstrated (Table 13 and FIG. 11), with cross-reactivity at lower antigen concentrations and for Wellington and Panama following a single vaccination at the 7.5 µg dose. The "Positive Titer" line has the same meaning as in FIG. 9.

TABLE 13

Ferret Study #3: HAI Titers and Seroconversion to A/Wisconsin and Other H3N2 Influenza Strains in Ferrets Following a Single Intranasal Dose of Commercial Vaccine Fluzone ® ± 20% $W_{80}5EC$-Adjuvant

| Treatment | Route | Total Antigen Dose (µg HA) | Wisconsin | | Wyoming | | California | | Wellington | | New York | | Panama | |
|---|---|---|---|---|---|---|---|---|---|---|---|---|---|---|
| | | | GMT[1] | %[2] | GMT | % | GMT | % | GMT | % | GMT | % | GMT | % |
| Fluzone ® + 20% $W_{80}5EC$ | IN[3] | 7.5 | 2663 | 100% | 192 | 67% | 784 | 83% | 34 | 33% | 806 | 83% | 16 | 17% |
| Fluzone ® + 20% $W_{80}5EC$ | IN | 3 | 440 | 83% | 38 | 33% | 51 | 33% | 10 | 0% | 163 | 67% | 16 | 17% |
| Fluzone ® + 20% $W_{80}5EC$ | IN | 0.9 | 206 | 67% | 10 | 0% | 11 | 0% | 11 | 0% | 65 | 50% | 11 | 0% |
| Fluzone ® | IM[4] | 37.5[5] | 10 | 0% | 10 | 05 | 10 | 0% | 10 | 0% | 10 | 0% | 10 | 0% |

[1]Geometric Mean Titer
[2]% seroconversion defined as HAI >40
[3]Intranasal
[4]Intramuscular
[5]The vaccine titer was reported here as 37.5 µg/0.5 mL according to SRID test performed prior to vaccination which showed that there was loss of the Wisconsin vaccine potency. The average reading on the SRID was 12.5 µg instead of 15 µg. It was assumed that the other 2 strains were reduced in similar pattern and all the vaccine doses were calculated accordingly.

Example 5

Efficacy and Dose Ranging of Nanoemulsion Adjuvanted Commercial Influenza Vaccine in Animal Model The goal of this study was to evaluate the efficacy of the nanoemulsions according to the present invention in a ferret model. This study was designed to compare the efficacy of different concentrations of the NE, different volumes and doses of the antigen to determine the dose response curve of the NE seasonal vaccine in a ferret model.

Ferret Study #4

The experiments were performed as described in the foregoing examples. Six ferrets were used in each testing group and two doses were given 4 weeks apart to each animal. The vaccine used in these ferrets was Fluzone® 2008-2009 formulation: A/Brisbane/59/2007(H1N1); A/Uruguay/716/2007 (H3N2), an A/Brisbane/10/2007-like strain; and B/Florida/4/2006.

Figure 12:
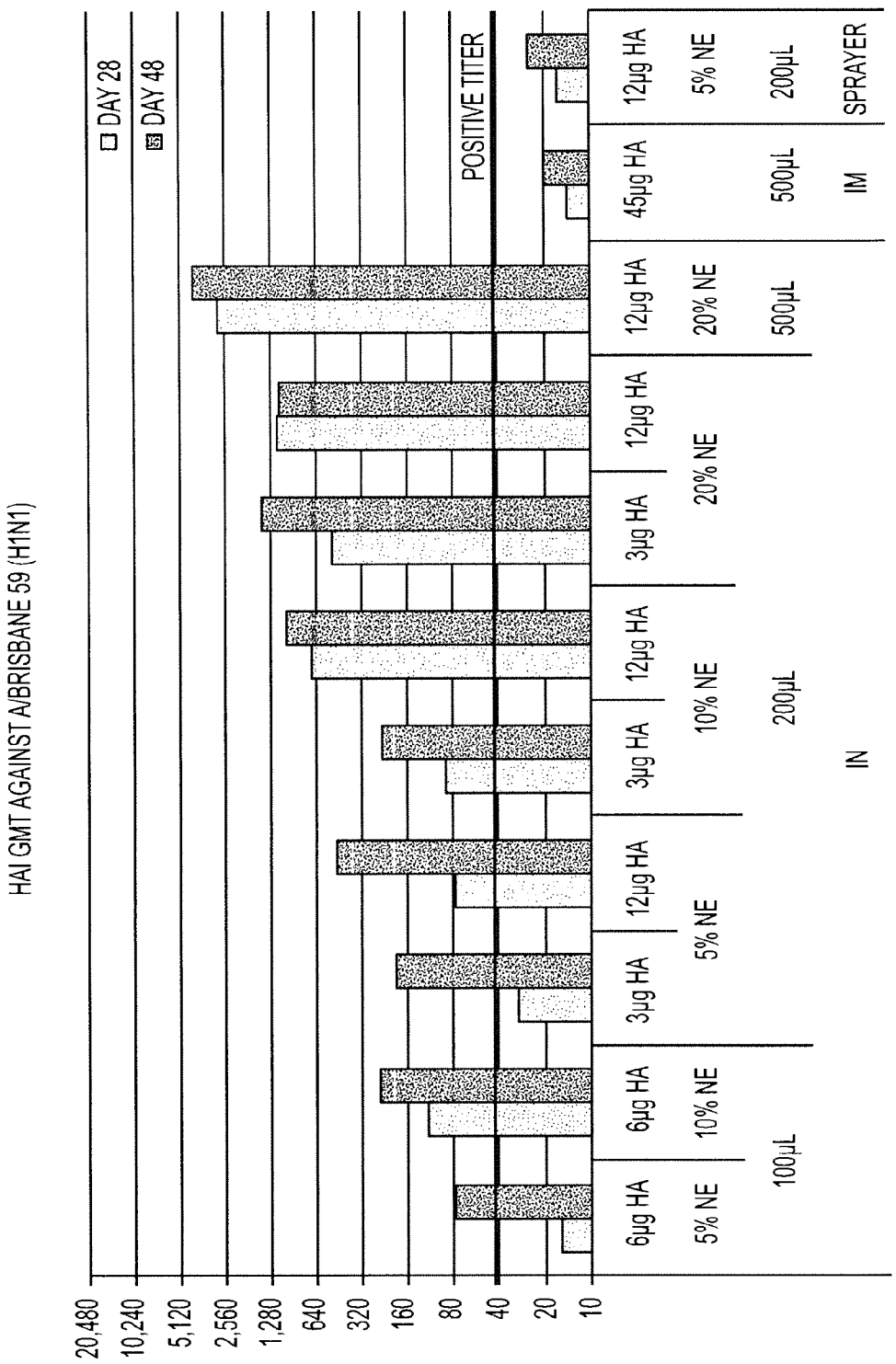
FIG. 12 shows the geometric mean HAI titer response to the nanoemulsion vaccine described in Example 5 in ferrets against A/Brisbane 59 (H1N1).
Figure 13:
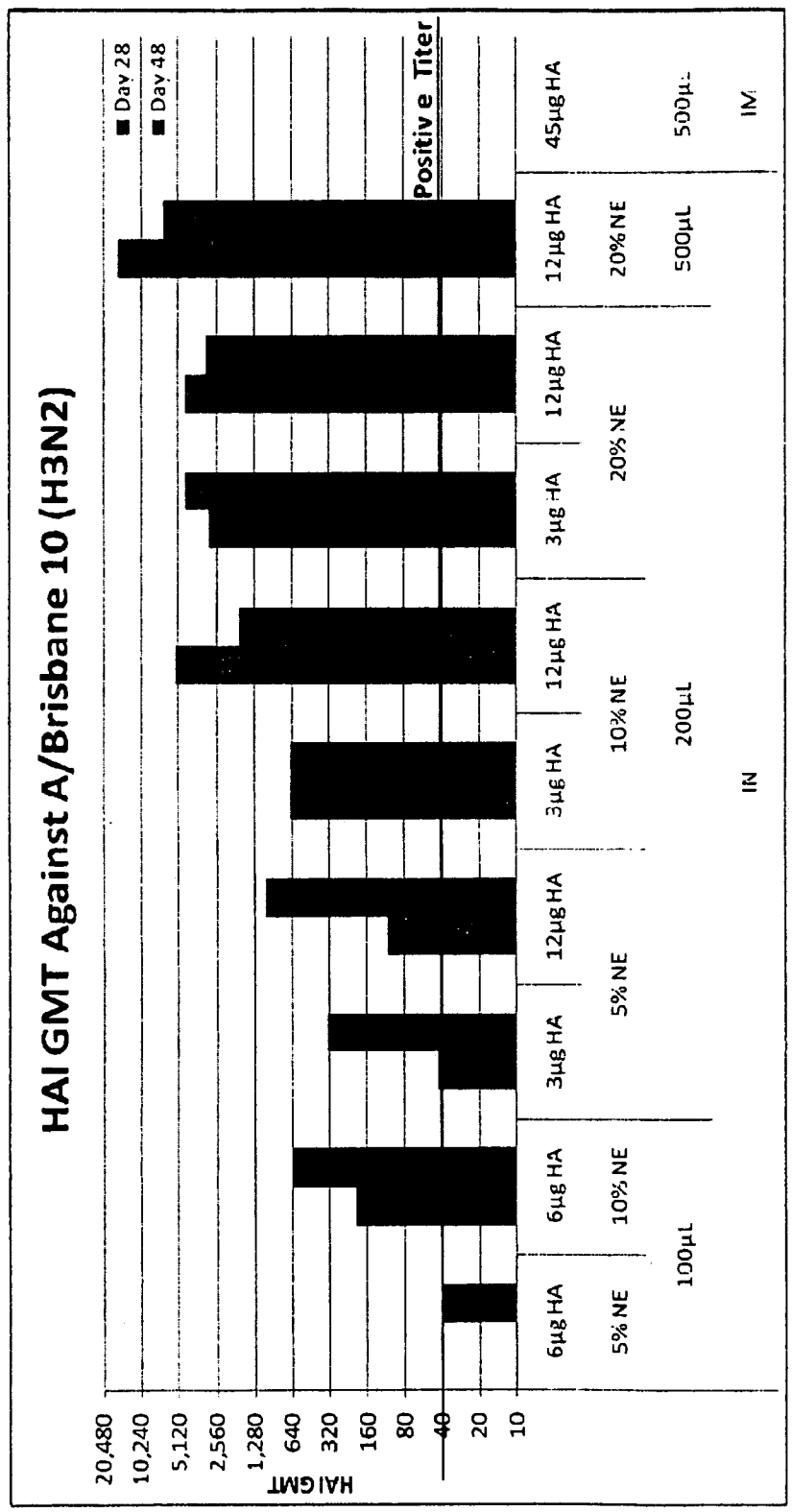
FIG. 13 shows the geometric mean HAI titer response to the nanoemulsion vaccine described in Example 5 in ferrets against A/Brisbane 10 (H3N2).
Figure 14:
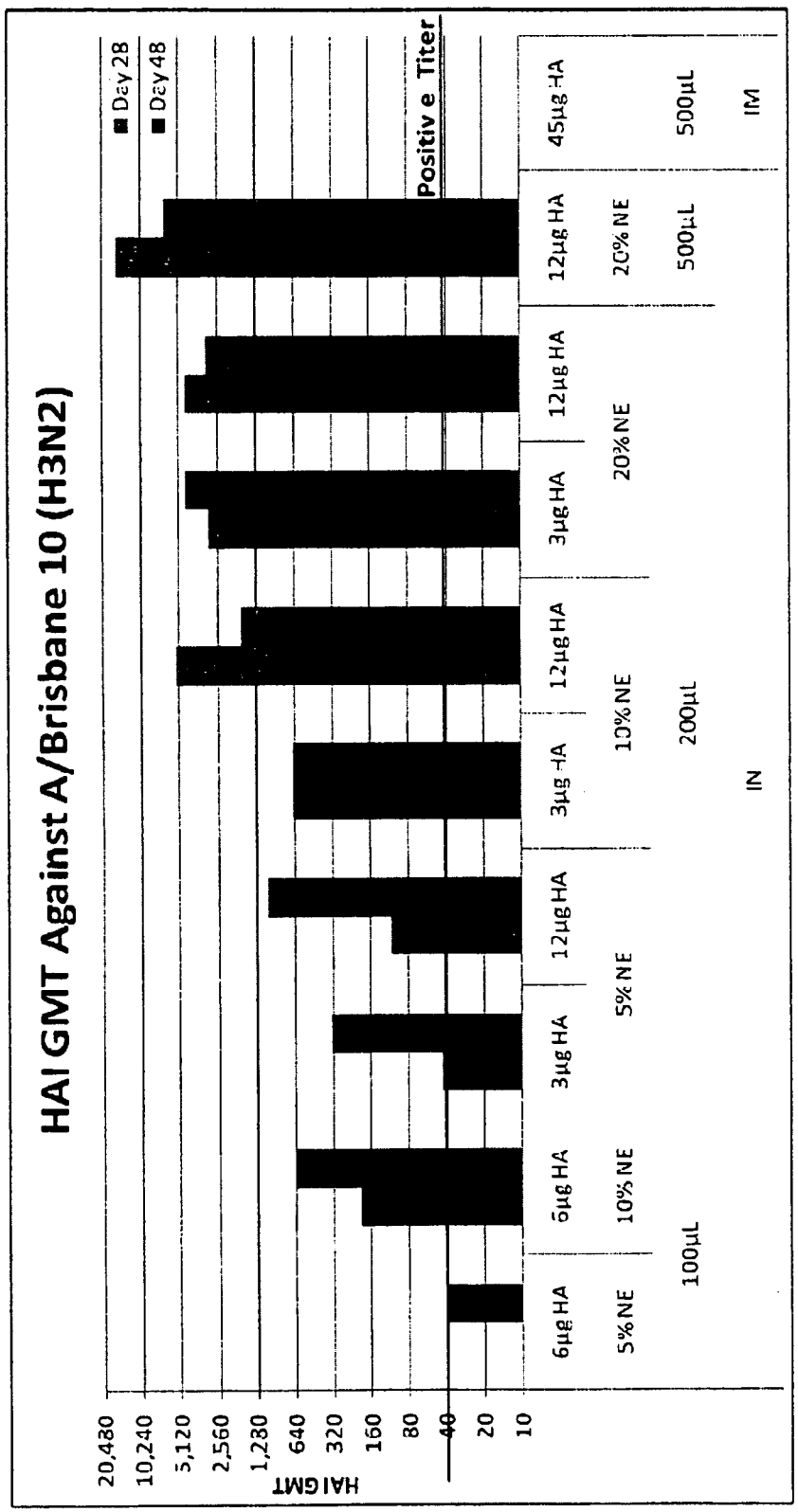
FIG. 14 shows the geometric mean HAI titer response to the nanoemulsion vaccine described in Example 5 in ferrets against B/Florida.
Figure 15:
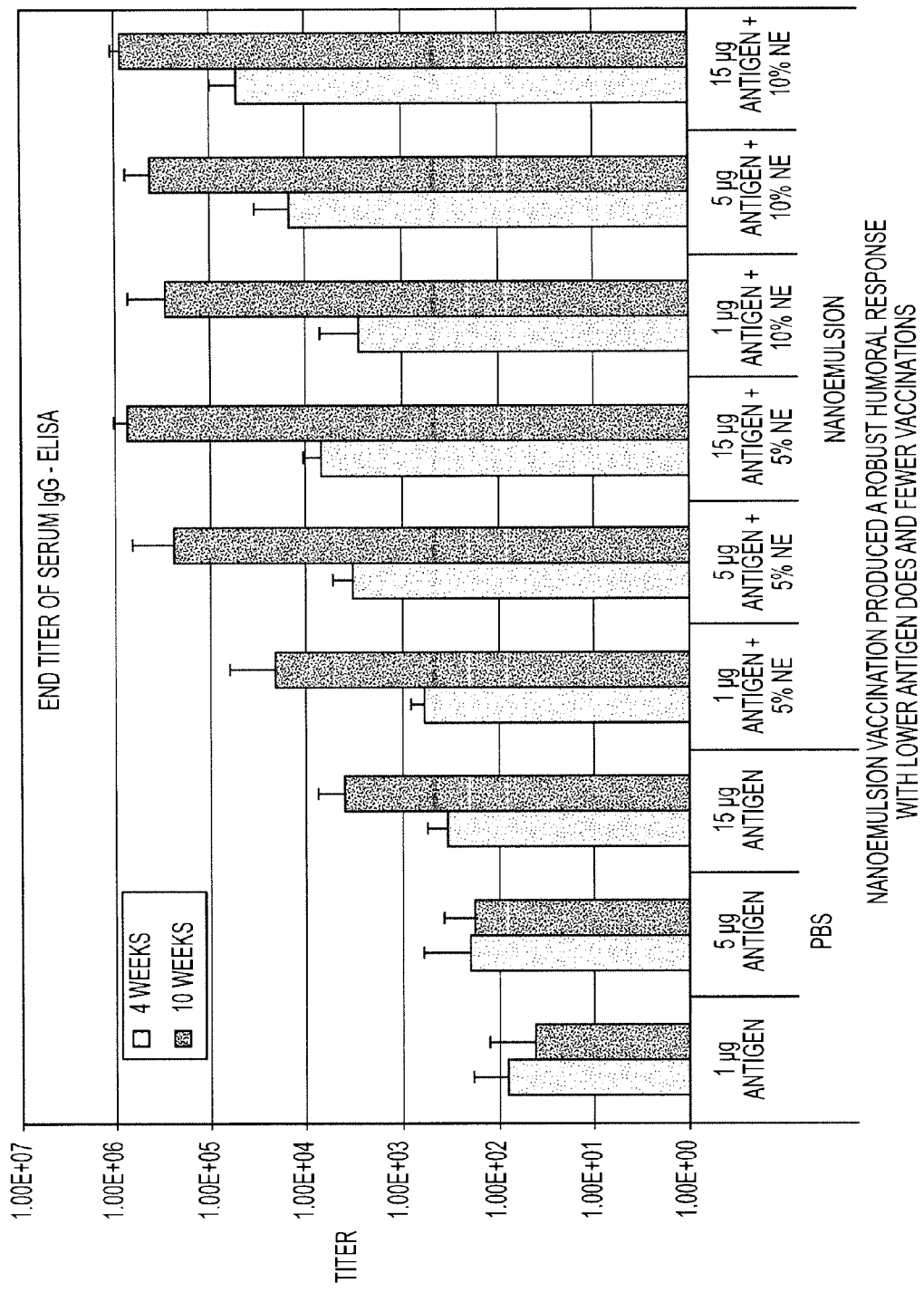
FIG. 15 shows serum IgG titer by ELISA for rH5/Indonesia (clade 2.1) antigen after two intranasal immunizations using different concentrations of H5 adjuvanated with 5% or 10% $W_{80}5EC$ into CD1 mice.
Figure 16:
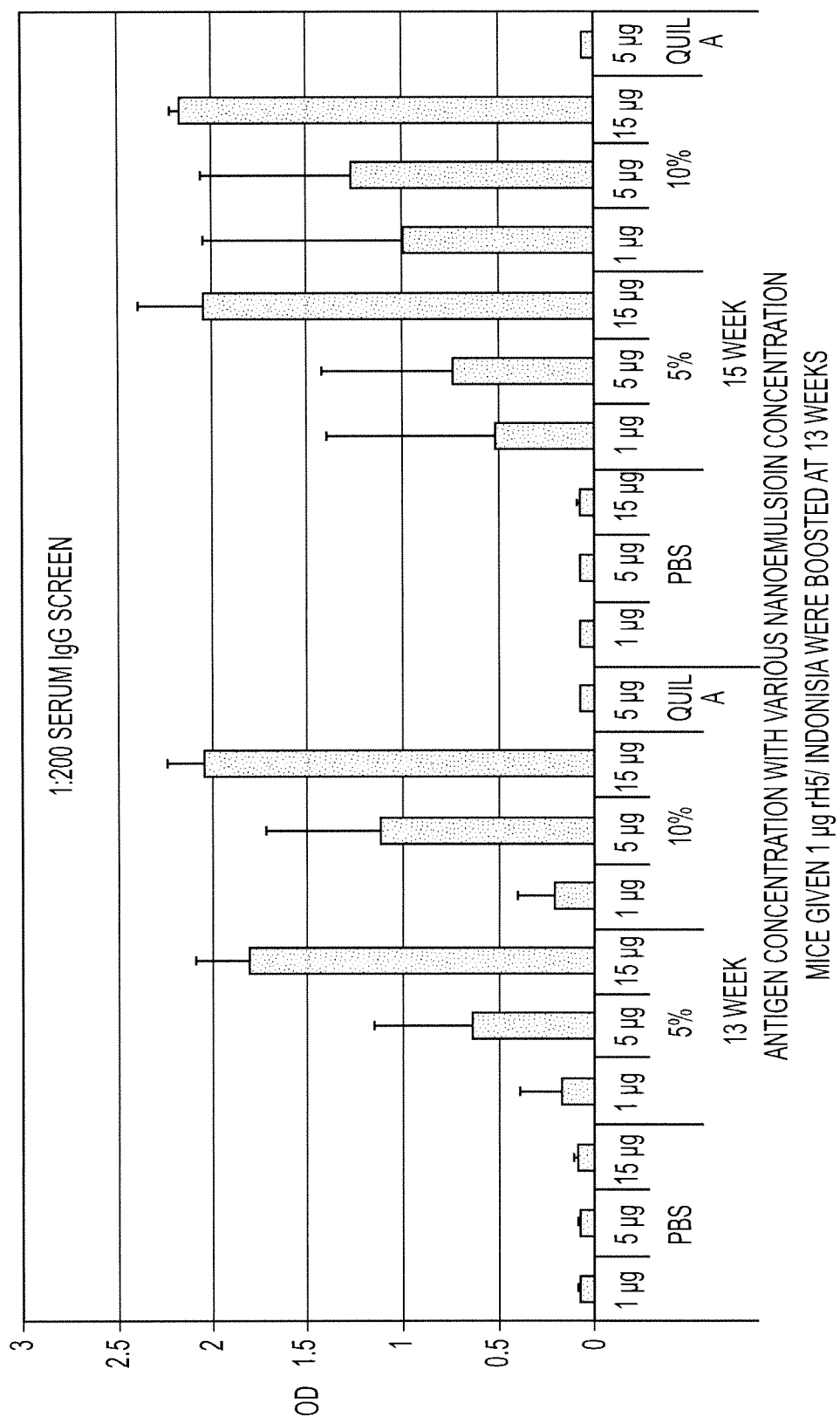
FIG. 16 shows increase in serum IgG following two immunizations (15 µg rH5) or three immunizations with 1 µg rH5/Indonesia antigen adjuvanted with 5% or 10% W805EC (boost given at 13 weeks), intranasally administered into CD1 mice.
Figure 18:
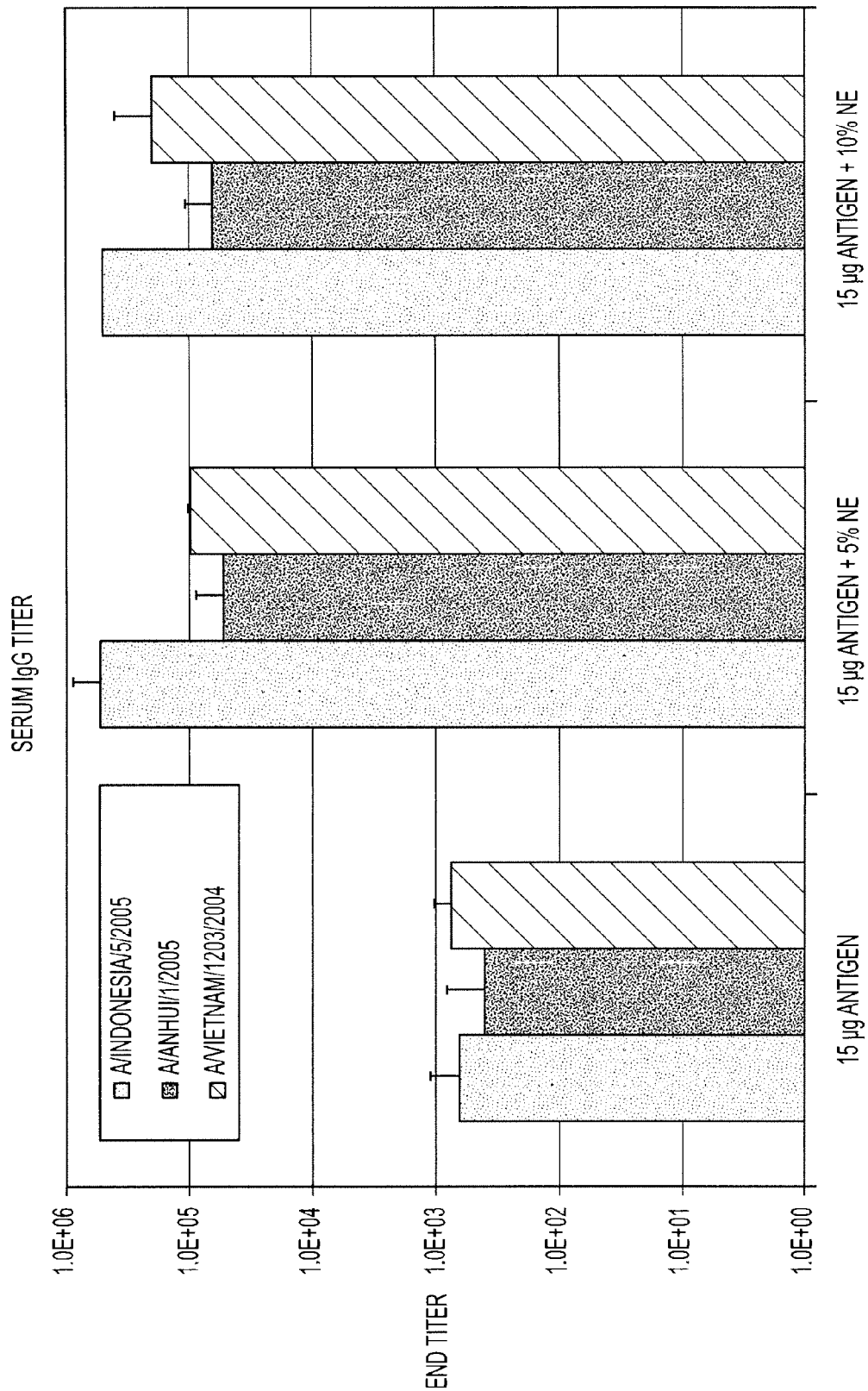
FIG. 18 shows that the immune response to the nanoemulsion adjuvanted rH5 vaccine has cross reactivity to distant clades of avian influenza.
Figure 19:
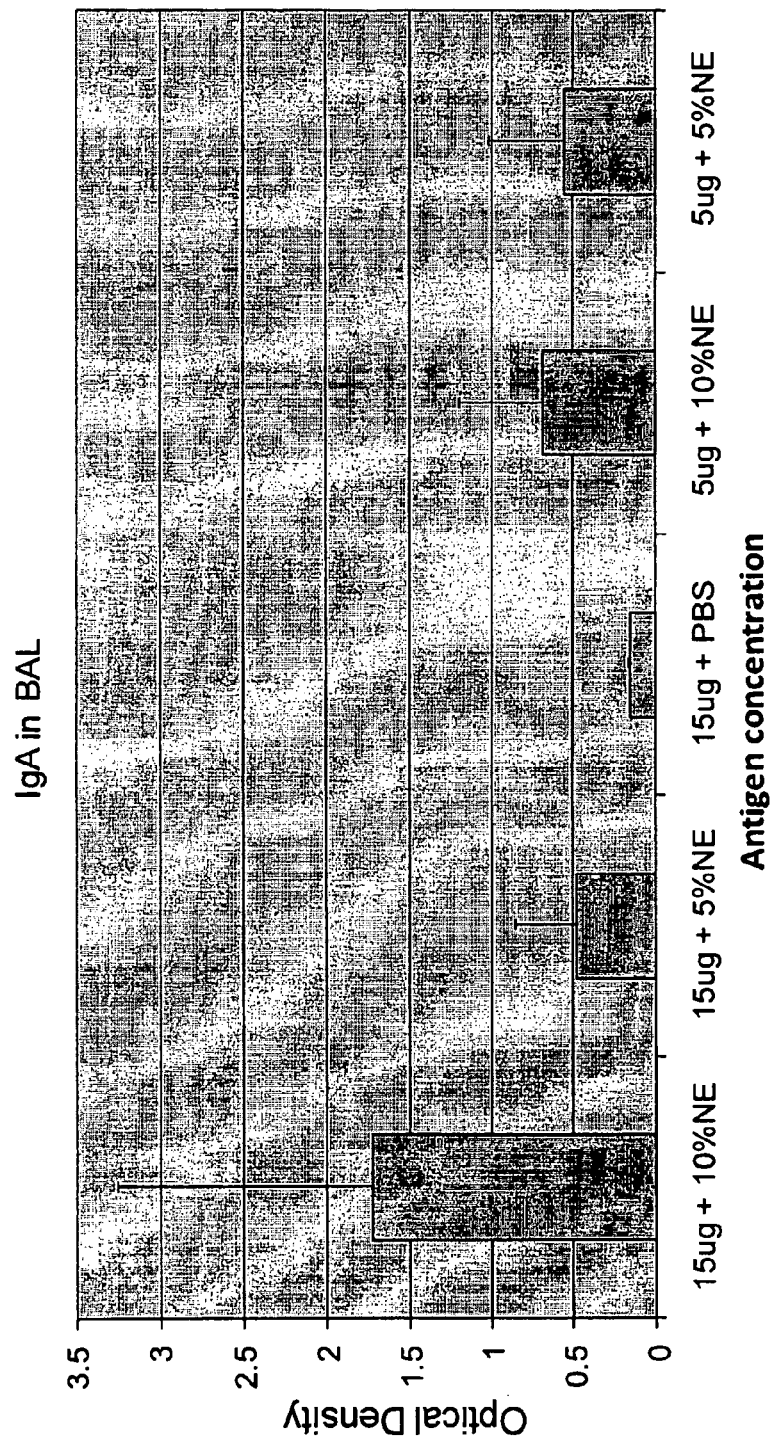
FIG. 19 shows that intranasal vaccination with $W_{80}5EC$-adjuvanted rH5/Indonesia produced secretory IgA in the bronchial aveolar lavage fluid in mice.
Figure 20:
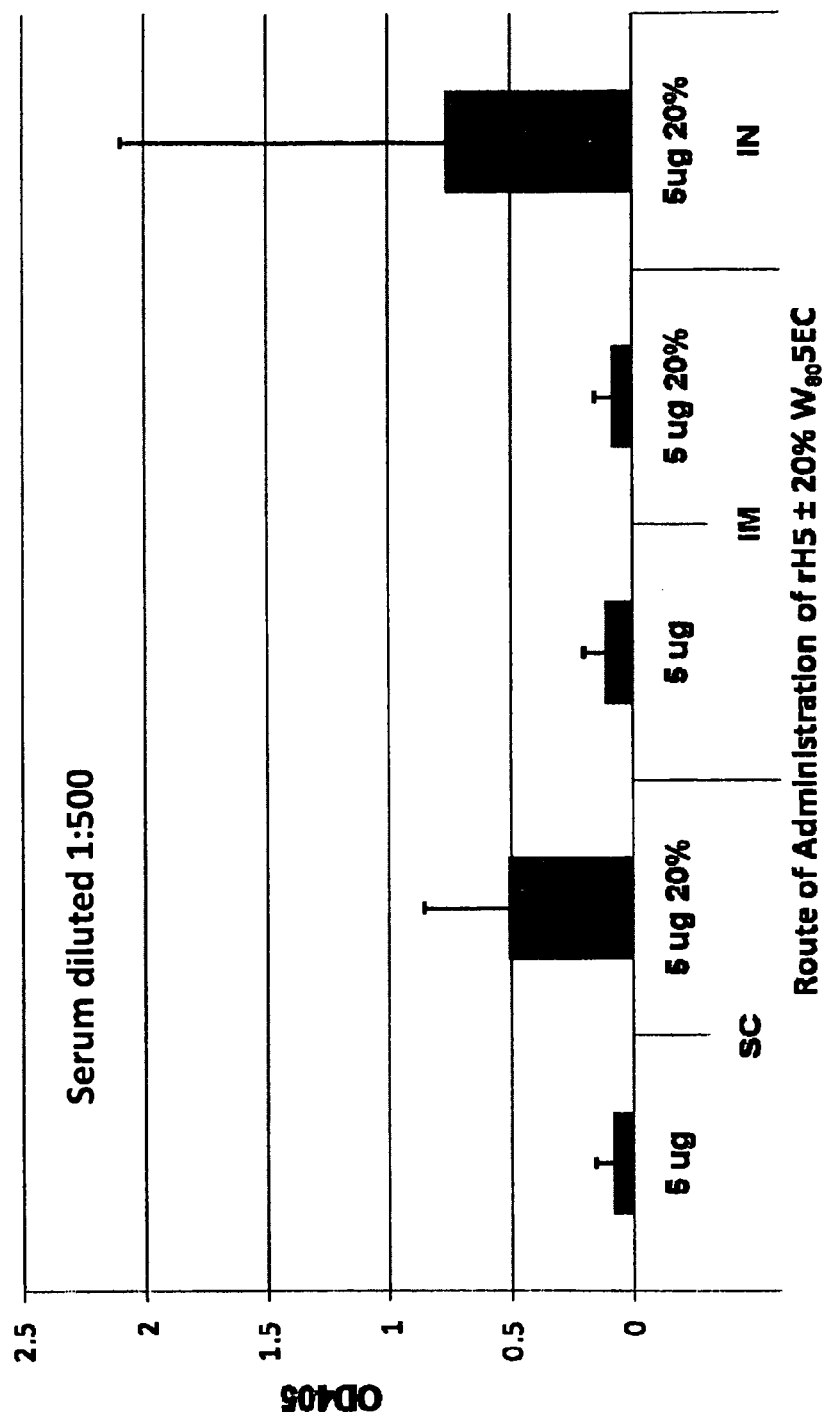
FIG. 20 shows the results of a serum IgG screen for CD1 mice four weeks following prime immunization (via SC, IM or IN) with recombinant H5 (rH5) antigen from A/Indonesia/05/05 combined with 20% $W_{80}5EC$ nanoemulsion vaccine adjuvant.

The study design is summarized in Table 14 and data are displayed in Tables 15 and 16 and graphically in FIGS. 12-14.

TABLE 14

Ferret Study #4: Fluzone ® (2008-2009) Commercial Vaccine + $W_{80}5EC$-Adjuvant Immunogenicity Study in Ferrets

| Route | Tx Group | N | Doses | $W_{80}5EC$-Adjuvant Concentration | Total Antigen (Fluzone ®) (2008-2009) (µg) | Total Volume (µL) | Rationale |
|---|---|---|---|---|---|---|---|
| IN | 1 | 6 | 2 | 20% | 12 | 500 | Replicate prior study |
|  | 2 | 6 | 2 | 5% | 12 | 200 | Assess effect of |
|  | 3 | 6 | 2 | 5% | 3 | 200 | nanoemulsion |
|  | 4 | 6 | 2 | 10% | 12 | 200 | concentration and |
|  | 5 | 6 | 2 | 10% | 3 | 200 | antigen dose on |
|  | 6 | 6 | 2 | 20% | 12 | 200 | immune response |
|  | 7 | 6 | 2 | 20% | 3 | 200 |  |
|  | 8 | 6 | 2 | 5% | 6 | 100 | Assess effect of |
|  | 9 | 6 | 2 | 10% | 6 | 100 | lower dose volume on immune response |
| IM | 10 | 6 | 2 | NA | 45 | 500 | IM Control |

As shown in FIGS. 12-14, the immune response to Fluzone® 12 µg+20% $W_{80}5EC$-adjuvant administered at 500 µL was very similar to the prior experience obtained in earlier studies. Increasing the $W_{80}5EC$-adjuvant concentration from 5% to 10% or to 20% at an equivalent antigen dose resulted in increased GMT response and increased seroconversion at 3, 6 and 12 µg total HA doses, respectively. It appears that increasing the volume from 200 µL to 500 µL at an equivalent 12 µg total HA dose also increased the immune response. The IM control elicited a minimal immune response and performed as expected based upon prior experience. Robust immune responses were demonstrated after one and two vaccinations using 10% $W_{80}5EC$- and 20% $W_{80}5EC$-adjuvant each with 12 µg total HA.

TABLE 15

Ferret Study #4: HAI Titers and Seroconversion to the Three Influenza Vaccine Strains in Ferrets Following a Single Intranasal Dose of Commercial Vaccine Fluzone ® (2008-2009) ± 20% $W_{80}5EC$-Adjuvant (Day 28)

| Treatment | Route/N | Total Volume Administered (µL) | Total Antigen Dose (µg HA) | A/Brisbane 59 (H1N1) GMT[1] | %[2] | A/Brisbane 10 (H3N2) GMT | % | B/Florida/ 04/2006 GMT | % |
|---|---|---|---|---|---|---|---|---|---|
| Fluzone ® + 20% $W_{80}5EC$ | IN[3]/6 | 500 | 12 | 2849 | 100% | 15494 | 100% | 698 | 100% |
| Fluzone ® + 5% $W_{80}5EC$ | IN/6 | 200 | 12 | 80 | 67% | 108 | 50% | 16 | 17% |
| Fluzone ® + 5% $W_{80}5EC$ | IN/6 | 200 | 3 | 30 | 33% | 43 | 33% | 13 | 17% |
| Fluzone ® + 10% $W_{80}5EC$ | IN/6 | 200 | 12 | 698 | 100% | 5325 | 100% | 108 | 83% |
| Fluzone ® + 10% $W_{80}5EC$ | IN/6 | 200 | 3 | 92 | 67% | 653 | 83% | 10 | 0% |
| Fluzone ® + 20% $W_{80}5EC$ | IN/6 | 200 | 12 | 1163 | 100% | 4434 | 100% | 153 | 100% |
| Fluzone ® + 20% $W_{80}5EC$ | IN/6 | 200 | 3 | 518 | 100% | 2930 | 100% | 76 | 67% |
| Fluzone ® + 5% $W_{80}5EC$ | IN/6 | 100 | 6 | 16 | 17% | 10 | 0% | 10 | 0% |
| Fluzone ® + 10% $W_{80}5EC$ | IN/6 | 100 | 6 | 21 | 7% | 96 | 7% | 0 | 50% |
| Fluzone ® | IM[4]/6 | 500 | 45 | 4 | 7% | 0 | % | 0 | 0% |

TABLE 16

Ferret Study #4: HAI Titers and Seroconversion to the Three Influenza Vaccine Strains in Ferrets Following Two Intranasal Doses of Commercial Vaccine Fluzone ® (2008-2009) ± 20% $W_{80}5EC$-Adjuvant (Day 48)

| Treatment | Route/N | Total Volume Administered (µL) | Total Antigen Dose (µg HA) | A/Brisbane 59 (H1N1) GMT[1] | %[2] | A/Brisbane 10 (H3N2) GMT | % | B/Florida/ 04/2006 GMT | % |
|---|---|---|---|---|---|---|---|---|---|
| Fluzone ® + 20% $W_{80}5EC$ | IN[3]/6 | 500 | 12 | 4144 | 100% | 6597 | 100% | 2261 | 100% |

TABLE 16-continued

Ferret Study #4: HAI Titers and Seroconversion to the Three Influenza Vaccine Strains in Ferrets
Following Two Intranasal Doses of Commercial Vaccine Fluzone ® (2008-2009) ± 20%
$W_{80}5EC$-Adjuvant (Day 48)

| Treatment | Route/N | Total Volume Administered (µL) | Total Antigen Dose (µg HA) | A/Brisbane 59 (H1N1) GMT[1] | %[2] | A/Brisbane 10 (H3N2) GMT | % | B/Florida/ 04/2006 GMT | % |
|---|---|---|---|---|---|---|---|---|---|
| Fluzone ® + 5% $W_{80}5EC$ | IN/6 | 200 | 12 | 479 | 100% | 1041 | 100% | 65 | 67% |
| Fluzone ® + 5% $W_{80}5EC$ | IN/6 | 200 | 3 | 196 | 83% | 328 | 83% | 10 | 0% |
| Fluzone ® + 10% $W_{80}5EC$ | IN/6 | 200 | 12 | 1036 | 100% | 1677 | 100% | 411 | 100% |
| Fluzone ® + 10% $W_{80}5EC$ | IN/6 | 200 | 3 | 242 | 83% | 653 | 83% | 57 | 50% |
| Fluzone ® + 20% $W_{80}5EC$ | IN/6 | 200 | 12 | 1140 | 100% | 3074 | 100% | 264 | 100% |
| Fluzone ® + 20% $W_{80}5EC$ | IN/6 | 200 | 3 | 1491 | 100% | 4434 | 100% | 392 | 83% |
| Fluzone ® + 5% $W_{80}5EC$ | IN/6 | 100 | 6 | 80 | 67% | 40 | 33% | 13 | 17% |
| Fluzone ® + 10% $W_{80}5EC$ | IN/6 | 100 | 6 | 242 | 83% | 634 | 83% | 121 | 83% |
| Fluzone ® | IM[4]/6 | 500 | 45 | 20 | 33% | 10 | 0% | 10 | 0% |

Example 6

H5N1 Influenza Study in Animal Model

The goal of this study was to assess the nanoemulsion as an adjuvant of a recombinant H5 influenza antigen (rH5) in inducing an immune response in mice.

6.1 Antigen Source

The recombinant H5 (A/Indonesia/05/2005) antigen used in this study was prepared and purified in tobacco plants (Shoji et al., Vaccine; 27:1087-92 (2008)).

6.2 Animal Studies

The study was designed according to Table 17, in which CD1 mice received two intransal immunizations of NE-adjuvanted vaccine 4 weeks apart. Ten groups of CD1 mice were tested, five in each group. Test animals received two doses intransally (IN) four weeks apart. The mice were bled at two, four, and six weeks respectively and samples were collected at each time point. Quil A was the adjuvant used as a control for intramuscular administration (IM), This group (#10) received 3 subcutaneous (SC) doses of the Quil A adjuvanted vaccine at two-week intervals. Four out of five Quil A mice died within 36 hours of the first dose. The surviving Quil A mouse was boosted at two and four weeks.

TABLE 17

Study Design

| Group | Dose | Route and frequency |
|---|---|---|
| 1 | 1 μg antigen | IN - 0 and 4 weeks |
| 2 | 5 μg antigen | IN - 0 and 4 weeks |
| 3 | 15 μg antigen | IN - 0 and 4 weeks |
| 4 | 1 μg antigen + 5% NE | IN - 0 and 4 weeks |
| 5 | 5 μg antigen + 5% NE | IN - 0 and 4 weeks |
| 6 | 15 μg antigen + 5% NE | IN - 0 and 4 weeks |
| 7 | 1 μg antigen + 10% NE | IN - 0 and 4 weeks |
| 8 | 5 μg antigen + 10% NE | IN - 0 and 4 weeks |
| 9 | 15 μg antigen + 10% NE | IN - 0 and 4 weeks |
| 10 | 5 μg antigen + 10 μg Quil A | SC - 0, 2 and 4 weeks |

Using commercial antigens produced in HEK293 cells, mice sera were tested for cross-reactivity to other clades of avian influenza, clades 1 and 2.3 (FIG. 17).

Results

Sera were tested for specific antibody titers against rH5. The serum IgG titers at 4 weeks and at 10 weeks are shown in FIG. 15. Four weeks after the initial vaccination, there was a significant humoral response that could be boosted. Two weeks following a second boost with 1 μg rH5/Indonesia antigen adjuvanted with 5% or 10% $W_{80}$5EC (boost given at 13 weeks), there was a significant increase in anti-H5 serum IgG for these arms (FIG. 16).

Intranasal vaccination with $W_{80}$5EC-adjuvanted rH5/Indonesia produced secretory IgA in the bronchial lavage fluid in mice (FIG. 19). It has been previously shown that serum and mucosal antibodies independently contribute to resistance to infection The antibodies induced with $W_{80}$5EC-adjuvanted clade 2.1 rH5/Indonesia were cross-reactive to the heterologous clades and subclades (FIG. 18).

Example 7

The purpose of this example was to evaluate the serum IgG levels of mice following subcutaneous (SC), intramuscular (IM) and intransal (IN) immunization with a recombinant H5 antigen (rH5) produced in plant cells (see Example 6) combined with a nanoemulsion adjuvant according to the invention.

Four weeks prior to the prime immunization, serum was collected, diluted 1:500 and screened for IgG specific to recombinant H5 (rH5) antigen from A/Indonesia/05/05, a clade 2.1 avian influenza strain.

CD-1 mice were immunized with either 20 μl (SC) or intramuscularly (IM)) or 12 μl (IN) of recombinant H5 (rH5) antigen from A/Indonesia/05/05 mixed with 20% $W_{80}$5EC nanoemulsion vaccine adjuvant, on day 0. As shown in FIG. 20, both the intranasal and subcutaneous route of administration provided IgG responses following a single immunization.

Example 8
Efficacy of Nanoemulsion Adjuvanted Commercial Influenza Vaccine in Animal Model This study was done in White New Zealand rabbits to determine the immunogenicity of a Nanoemulsion adjuvanted commercial vaccine.

An exemplary influenza vaccine was prepared, composed of a nanoemulsion adjuvant (60% $W_{80}5EC$) mixed with Fluzone® (2008-2009) commercial vaccine. This formulation was designated "NB-1008 Vaccine". NB-1008 is composed of (a) commercial influenza vaccine [Fluzone® (2008-2009)]; (b) the oil-in-water nanoemulsion adjuvant (designated as "60% $W_{80}5EC$") described above, and (c) phosphate-buffered saline (PBS), where indicated, to achieve $W_{80}5EC$-adjuvant concentrations of 5, 10 and 20%.

A total number of 130 rabbits were used in the study. Two doses of the vaccines were administered intranasally to the rabbits at 0 and 2 weeks. The immunization was carried out according to the schedule of Table 18.

TABLE 18

Dosing of rabbits with test article

| Group # | Treatment | Days of Dosing | Total μg Fluzone ® | Number of Animals | Volume Administered (mL) |
|---|---|---|---|---|---|
| 1 | PBS | 1 and 15 | 0 | 10 | 0.5 |
| 2 | Fluzone ® + 10% $W_{80}5EC$ | 1 and 15 | 15 | 20 | 0.5 |
| 3 | Fluzone ® + 10% $W_{80}5EC$ | 1 and 15 | 30 | 20 | 0.5 |
| 4 | 10% $W_{80}5EC$ | 1 and 15 | 0 | 10 | 0.5 |
| 5 | Fluzone ® + 20% $W_{80}5EC$ | 1 and 15 | 15 | 20 | 0.5 |
| 6 | Fluzone ® + 20% $W_{80}5EC$ | 1 and 15 | 30 | 20 | 0.5 |
| 7 | 20% $W_{80}5EC$ | 1 and 15 | 0 | 10 | 0.5 |
| 8 | Fluzone ® | 1 and 15 | 30 | 20 | 0.5 |

Figure 22:
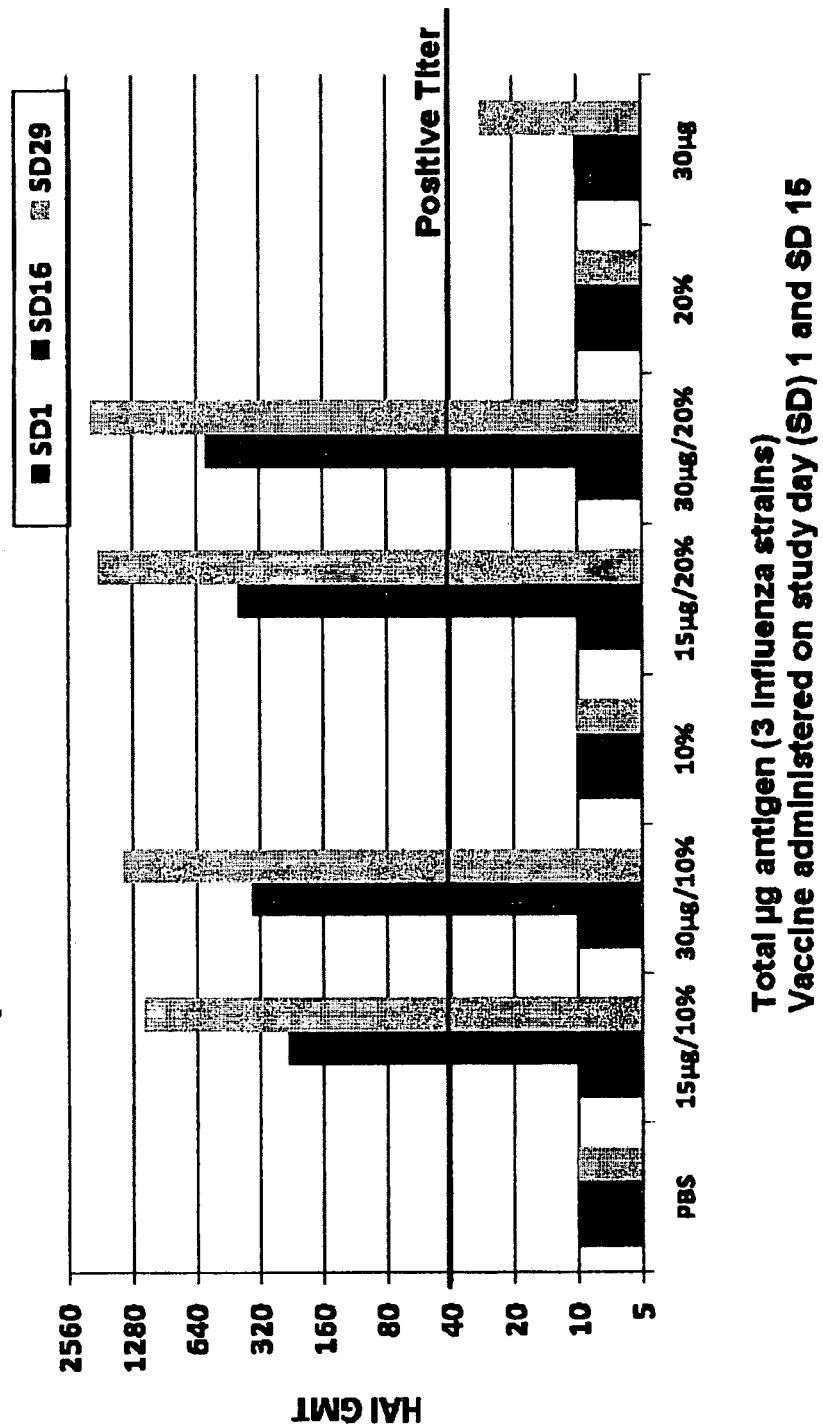
FIG. 22 shows the geometric mean HAI titer response to the nanoemulsion vaccine described in Example 7 in rabbits against A/Brisbane 10 (H3N2).
Figure 23:
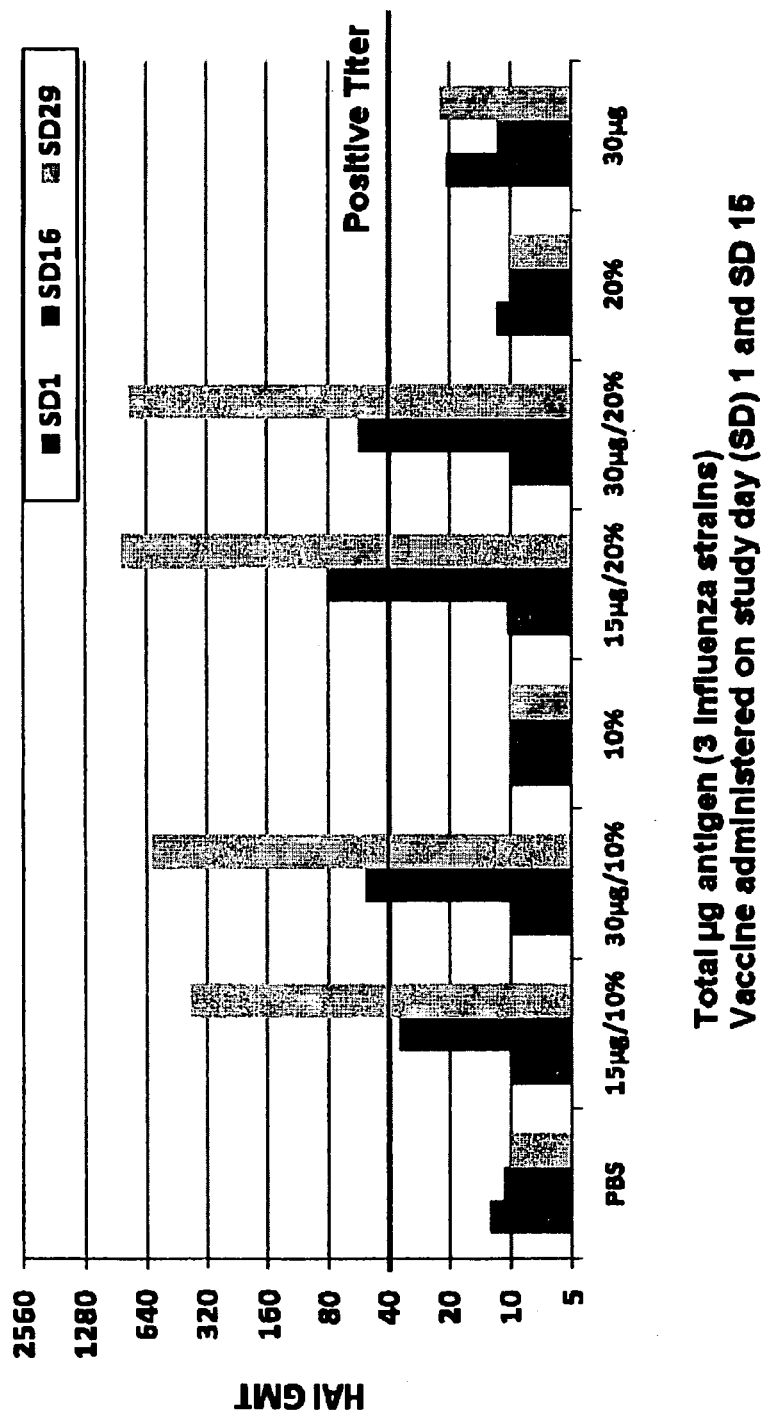
FIG. 23 shows the geometric mean HAI titer response to the nanoemulsion vaccine described in Example 7 in rabbits against B/Florida.
Figure 24:
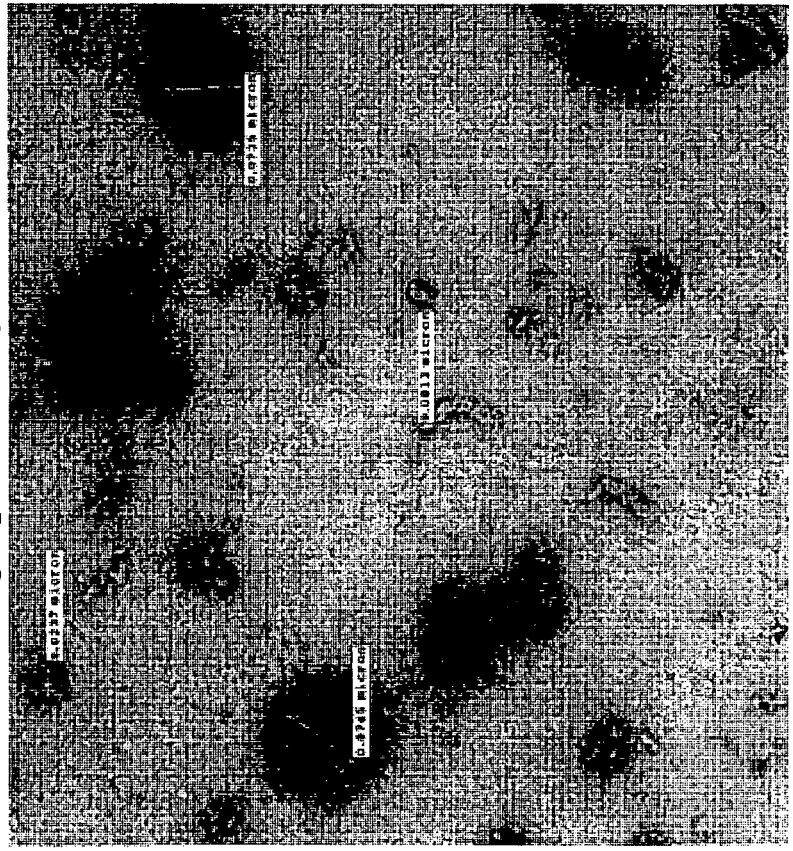
FIG. 24 depicts a transmission electron micrograph of Fluzone® 2008-2009 vaccine. Three distinct structures are shown, corresponding to viral antigen particles contained in Fluzone® 2008-2009 vaccine [≈25 nm (round), and ≈100 nm (crescent)].
Figure 25:
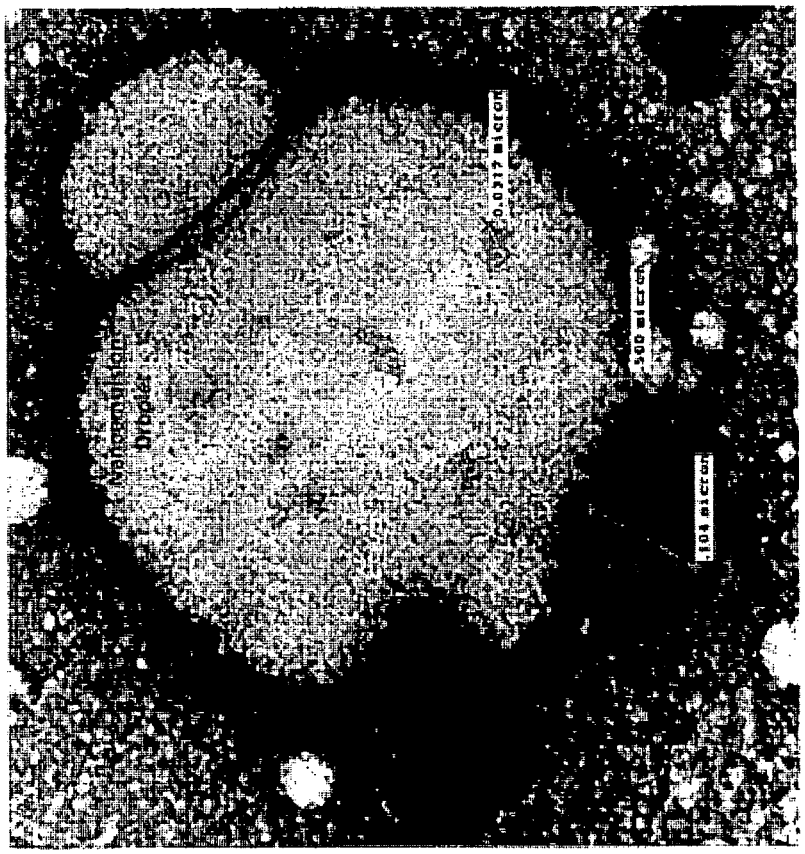
FIG. 25 depicts a transmission electron micrograph of a nanoemulsion, 5% $W_{80}5EC$ mixed with 7.5 µg of Fluzone® 2008-2009 vaccine. The majority of viral antigen particles are associated with the nanoemulsion droplets.
Figure 26:
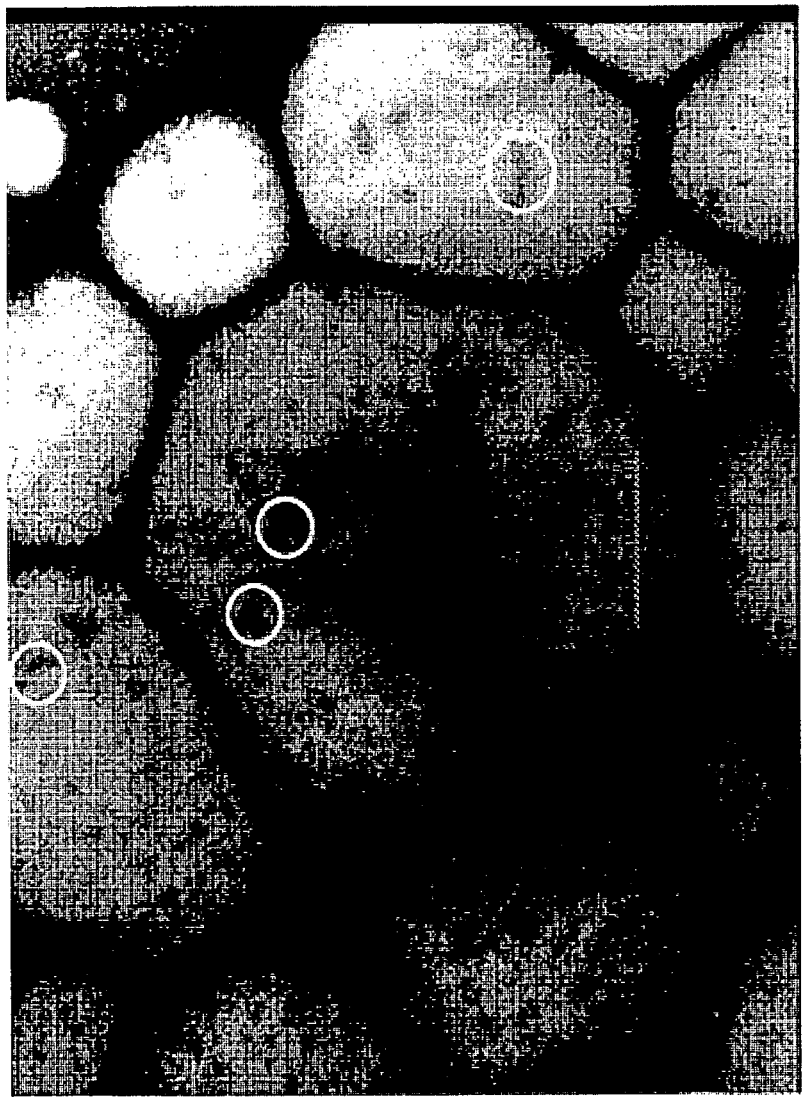
FIG. 26 depicts a transmission electron micrograph of a nanoemulsion, 20% $W_{80}5EC$ mixed with 7.5 µg of Fluzone®. Viral antigen particles can be seen associated with the nanoemulsion droplets. (Circled areas are representative of viral antigen particles.)

The results of HAI assay against three influenza strains, A/Brisbane 59 (H1N1), A/Brisbane 10 (H3N2) and B/Florida, are displayed in Table 19 and FIGS. 21, 22 and 23, respectively. Rabbits vaccinated with NE-adjuvanted vaccine showed high titers against all the strains on day 28. There was no immune response from either the nanoemulsion alone or the antigen alone. The data showed that the NE adjuvant can enhance the immune response.

TABLE 19

Day 29 HAI Titers and Seroconversion to the Three Influenza Vaccine Strains in Rabbits Following Two Intranasal Doses (Day 1 and Day 15) of Commercial Vaccine Fluzone ® (2008-2009) ± 20% $W_{80}5EC$-Adjuvant (Bridge Study #1819-08796)

| Treatment | Route/ N/Sex | Total Antigen Dose (μg HA) | A/Brisbane/59/2007 (H1N1) GMT[1] | % seroconversion[2] | A/Uruguay/ 716/2007 (H3N2) GMT | % seroconversion | B/Florida/04/2006 GMT | % seroconversion |
|---|---|---|---|---|---|---|---|---|
| PBS | IN[3]/2 | 0 | 10 | 0% | 10 | 0% | 10 | 0% |
| Fluzone ® + 10% $W_{80}5EC$ | IN/4 | 15 | 173 | 88% | 1116 | 100% | 381 | 100% |
| Fluzone ® + 10% $W_{80}5EC$ | IN/4 | 30 | 197 | 100% | 1396 | 100% | 595 | 100% |
| 10% $W_{80}5EC$ | IN/2 | 0 | 10 | 0% | 10 | 0% | 10 | 0% |
| Fluzone ® + 20% $W_{80}5EC$ | IN[4]/4 | 15 | 269 | 100% | 1810 | 100% | 830 | 100% |
| Fluzone ® + 20% $W_{80}5EC$ | IN/4 | 30 | 235 | 100% | 1974 | 100% | 761 | 100% |
| 20% $W_{80}5EC$ | IN/2 | 0 | 12 | 0% | 10 | 0% | 10 | 0% |
| Fluzone ® | IN/4 | 30 | 17 | 13% | 28 | 50% | 22 | 25% |

[1]Geometric Mean Titer
[2]Responder defined as HAI > 40
[3]IN Intranasal

Example 9
Safety of IN Nanoemulsion Adjuvanted Influenza Vaccine

Safety in Ferrets

A total of 249 ferrets received at least one dose on intransal $W_{80}5EC$-adjuvant plus influenza antigen. All animals were observed twice daily for morbidity and mortality and no abnormal observations or altered activity was noted. In addition, clinical signs, body weights and body temperatures were evaluated weekly. No significant clinical signs or effects on body weights or body temperatures were reported in this study. Intranasal administration of $W_{80}5EC$-adjuvanted vaccines has been well tolerated without significant treatment-related clinical abnormalities A Repeat Intranasal Dose Toxicity Study in the New Zealand White Rabbit A GLP toxicity study was conducted with rabbits employing the design shown in Table 20.

Methods

The vaccine was prepared extemporaneously for each individual rabbit by mixing the appropriate volume of Fluzone® (2008-2009) plus phosphate-buffered saline (PBS), as required, and 60% $W_{80}5EC$-adjuvant. The total antigen dose administered to rabbits was 15 μg (3×5 μg) and 30 μg (3×10 μg) total HA antigen from the Fluzone® (2008-2009) vaccine. Each antigen dose was administered in final $W_{80}5EC$-adjuvant concentrations of 10% and 20%. A total volume of 500 μL (250 μL/nare) was administered to each rabbit. The rabbits were anesthetized and placed in a dorsal recumbent position. The required vaccine dose was withdrawn from the vial and administered intranasally in a drop wise fashion into each nare using a 1 mL syringe and rounded 18 gauge gavage needle. Each drop was approximately 10-25 μL and approximately 10-20 drops were delivered in each nare. The vaccine was administered on two occasions two weeks apart (Day 1 and Day 15).

TABLE 20

$W_{80}5EC$-Adjuvanted Fluzone ® (2008-2009 Vaccine): A Repeat Intranasal Dose Toxicity and Immunogenicity Study in the New Zealand White Rabbit

| Treatment Group | Treatment | Amount of Influenza Antigen (Total μg HA)[a] | Route | N (F/M) | Number of Doses[b] | Total Volume (250 μL/nare) |
|---|---|---|---|---|---|---|
| 1 | PBS | 0 | IN | 5/5 | 2 | 500 |
| 2 | Fluzone ® + 10% $W_{80}5EC$ | 15 | IN | 10/10 | 2 | 500 |
| 3 | Fluzone ® + 10% $W_{80}5EC$ | 30 | IN | 10/10 | 2 | 500 |
| 4 | 10% $W_{80}5EC$ | 0 | IN | 5/5 | 2 | 500 |
| 5 | Fluzone ® + 20% $W_{80}5EC$ | 15 | IN | 10/10 | 2 | 500 |
| 6 | Fluzone ® + 20% $W_{80}5EC$ | 30 | IN | 10/10 | 2 | 500 |
| 7 | 20% $W_{80}5EC$ | 0 | IN | 5/5 | 2 | 500 |
| 8 | Fluzone ® | 30 | IN | 10/10 | 2 | 500 |

[a] A/Brisbane/59/2007 (H1N1), A/Uruguay/716/2007 (H3N2) and B/Florida/04/2006.
[b] Doses were administered on Day 1 and 15. Samples for HAI titers were collected on Day 0, 16 and on Day 29.

In this study, there were no significant clinical signs or altered behavior, no significant effects on body weights or food consumption, no significant effects on temperature, no findings on ophthalmic examination and no significant changes in serum chemistry or urinary parameters. Changes in absolute neutrophil count in groups treated with $W_{80}$5EC-adjuvant alone or $W_{80}$5EC-adjuvant in combination with Fluzone® were minimal and reversible and were not considered adverse. Gross pathology was unremarkable. Microscopically, reversible, superficial, minimal to mild, focal accumulations of neutrophils within or adjacent to the nasal or nasopharyngeal mucosa in rabbits receiving $W_{80}$5EC-adjuavnt alone or $W_{80}$5EC-adjuvant in combination with Fluzone® were the only treatment related microscopic findings. All were reversible and not considered adverse.

Example 10

The purpose of the example was to visualize the effect of combining a nanoemulsion adjuvant according to the invention with a commercial vaccine, such as Fluzone® using transmission electron microscopy.

Fluzone® is a licensed commercial vaccine manufactured by sanofi pasteur and is approved for intramuscular (IM) administration in the U.S. The vaccine is available in a single dose or multi-dose presentation. Each 0.5 mL dose contains a total of 45 μg of influenza virus hemagglutinin (HA) and for the 2008/2009 season included 15 μg of each of the following 3 strains: A/Brisbane/59/2007 (H1N1), A/Uruguay/716/2007, [A/Brisbane/10/2007-like strain] (H3N2), and B/Florida/04/2006.

Three transmission electron micrographs are presented. The first transmission electron micrograph, shown in FIG. 24, depicts Fluzone® 2008-2009 vaccine. Three distinct structures are shown, corresponding to viral antigen particles contained in Fluzone® 2008-2009 vaccine [≈25 nm (round), ≈100 nm (round), and ≈100 nm (crescent)]. The second transmission electron micrograph, shown in FIG. 25, depicts a nanoemulsion vaccine according to the invention (5% $W_{80}$5EC; see Table 1.1) mixed with 7.5 μg of Fluzone® 2008-2009 vaccine. The majority of viral antigen particles are associated with the nanoemulsion droplets. Finally, the third transmission electron micrograph, shown in FIG. 26, depicts a nanoemulsion vaccine according to the invention at a higher concentration (20% $W_{80}$5EC; see Table 1.1) mixed with 7.5 μg of Fluzone®. Viral antigen particles can be seen associated with the nanoemulsion droplets. (Circled areas are representive of viral antigen particles.)

Example 11

Stability of Nanoemulsion Vaccine Adjuvants

The purpose of this example was to evaluate the stability of a nanoemulsion vaccine adjuvant over various time points.

Table 21 provides 3 month stability data for a nanoemulsion vaccine adjuvant according to the invention (60% $W_{80}$5EC nanoemulsion vaccine adjuvant). Tables 22 and 23 below, present stability data at 12 months and at 18 months, respectively, for a nanoemulsion vaccine according to the invention (60% $W_{80}$5EC nanoemulsion vaccine adjuvant). In addition, Table 24 provides data regarding antimicrobial effectiveness.

The nanoemulsion vaccine adjuvant was stable at all temperatures tested over the 12 month period and the nanoemulsion adjuvant was stable at refrigerated and room temperature for up to 18 months. There was moderate separation of the emulsion at 40 C at 18 months.

TABLE 21

3 month stability data for 60% $W_{80}5EC$-

| Storage Condition | Storage Interval (months)[a] | Appearance | pH | Particle Size, Mean (nm) | Zeta Potential (mV)[b] | CPC Potency (Percent Label Claim) |
|---|---|---|---|---|---|---|
| | Initial | Passes | 4.9 | 467 | 25.9 | 99.2, 100.5 |
| 5° C. | 1 | Passes | 5.2 | 468 | NT | 105.2, 106.0 |
| 5° C. | 3 | Passes | 5.2 | 422 | 41.7 | 105.1, 107.7 |
| 25° C. | 1 | Passes | 5.1 | 477 | NT | 107.3, 99.9 |
| 25° C. | 3 | Passes | 5.1 | 429 | 56.9 | 102.4, 105.4 |
| 40° C./75% RH | 1 | Passes | 5.0 | 450 | NT | 106.7, 108.3 |
| 40° C./75% RH | 3 | Passes | 4.1 | 419 | 48.9 | 97.8, 99.2 |

TABLE 22

Stability data for 60% $W_{80}5EC$ at 12 months

| Storage temp. | Appearance (Degree of separation) | | Particle size (nm) | | pH | | CPC (% recovery) | |
|---|---|---|---|---|---|---|---|---|
| (°) | Initial | 12 months | Initial | 12 months | Initial | 12 months | Initial | 12 months |
| 5 ± 3° C. | Pass | Pass | N/A | 437.6 | N/A | 5.22 | N/A | 108.1 |
| 22 ± 3° C. | Pass | Pass | 444 | 448.2 | 5.11 | 5.21 | 101.4 | 105.3 |
| 40 ± 2° C. | Pass | Pass | N/A | 447.7 | N/A | 4.71 | N/A | 99.8 |

TABLE 23

Stability data for 60% $W_{80}5EC$ at 18 months

| Storage temp. | Appearance (Degree of separation) | | Particle size (nm) | | pH | | CPC (% recovery) | |
|---|---|---|---|---|---|---|---|---|
| (°) | Initial | 18 months | Initial | 18 months | Initial | 18 months | Initial | 18 months |
| 5 ± 3° C. | Pass | Pass | N/A | 474.2 | N/A | 5.28 | N/A | 105.6 |
| 22 ± 3° C. | Pass | Pass | 444 | 469.45 | 5.11 | 5.11 | 101.4 | 99.9 |
| 40 ± 2° C. | Pass | moderate | N/A | 469.5 | N/A | 4.68 | N/A | 106.1 |

CPC recovery for 18 months is w/v

TABLE 24

Antimicrobial Effectiveness, Category 2 Products, USP<51>

| | S. aureus | P. aeruginosa | E. coli | C. Albicans | A. niger |
|---|---|---|---|---|---|
| Time = 0 | PASS More than 2.6 log reduction from the initial count at 14 days, and no increase from the 14 days' count at 28 days. | PASS More than 4.5 log reduction from the initial count at 14 days, and no increase from the 14 days' count at 28 days. | PASS More than 4.5 log reduction from the initial count at 14 days, and no increase from the 14 days' count at 28 days. | PASS No increase from the initial calculated count at 14 and 28 days. | PASS No increase from the initial calculated count at 14 and 28 days. |

Example 12

Stability

The purpose of this example was to evaluate the stability of an influenza vaccine comprising a nanoemulsion vaccine adjuvant according to the invention.

Two influenza formulations were tested, as shown in Table 25 below. The nanoemulsion vaccine adjuvant used in this example was $W_{80}\%$ 5EC, described above. $W_{80}$ 5EC at 5% and at 20% were mixed with Fluzone® influenza vaccine (sanofi pasteur, 2008-2009) and the stability of the adjuvanted Fluzone® influenza vaccines was evaluated.

TABLE 25

| Sample Type | Sample Description |
|---|---|
| Nanoemulsion/Fluzone ®/PBS mixture | 5% $W_{80}5EC$ NE + 30 µg Fluzone ® <br> 20% $W_{80}5EC$ NE + 30 µg Fluzone ® |

The particle size was determined on a Malvern Zetasizer Nano ZS, a dynamic light scattering instrument. The samples were prepared as follows: All prepared mixtures for particle size were diluted further using 0.2 μm filtered DI water in the ratio corresponding to the requirements of the nanoemulsion dilution. Each of these preparations were then observed by microscopy prior to analysis, and a small population of particulate (around 4-6 μm) was observed. Particle size analyses were then conducted on each mixture at 0, 8, 24, and 48 hours from preparation.

The results are shown in Table 26.

TABLE 26

Average Particle Size over Time for Fluzone ® + NE adjuvant Formulations

| Formulation | Time (hours) | | | |
|---|---|---|---|---|
| | 0 | 8 | 24 | 48 |
| 5% $W_{80}$5EC NE + 30 μg Fluzone ® | 456 nm | 474 nm | 477 nm | 468 nm |
| 20% $W_{80}$5EC NE + 30 μg Fluzone ® | 454 nm | 454 nm | 447 nm | 462 nm |

The data demonstrate stability of the adjuvanted vaccine compositions over a 48 hour period.

Example 13

Stability

The purpose of this example was to evaluate the stability of a nanoemulsion adjuvanted vaccine according to the invention.

The stability of $W_{80}$5EC adjuvanted nanoemulsion vaccine was evaluated. The preparations tested were 20% $W_{80}$5EC-60 μg Fluzone®/mL and 20% $W_{80}$5EC-30 μg Fluzone®/mL in phosphate buffered saline (PBS). After preparation, the vaccines were stored at room temperature (22° C.) and refrigerated (5° C.) for up to 2 weeks.

20% $W_{80}$ 5EC is a nanoemulsion adjuvant comprising soybean oil, Tween-80, ethanol, PBS and cetylpyridinium chloride (CPC). Fluzone® 2008-2009 is an influenza virus vaccine for intramuscular injection manufactured by sanofi pasteur Inc. Fluzone® contains 90 μg total HA antigen/mL.

$W_{80}$5EC adjuvanted nanoemulsion vaccine stability was determined at room temperature and in refrigerated conditions. Stability time points were 2 days, 5 days, 1 week, and 2 weeks for the refrigerated samples and at 1 week and 2 weeks for the room temperature samples. Stability was assessed by product appearance, pH, zeta potential, particle size, and appearance.

Results

From the data it was concluded that both influenza vaccine mixtures were stable for at least two weeks under both storage conditions. Specifically, both NE-adjuvanted vaccines were visually stable in the 2 weeks stability assessment period. Appearance testing showed no difference between the 20% $W_{80}$5EC-60 μg Fluzone®/mL and 20% $W_{80}$5EC-30 μg Fluzone®/mL in PBS. Slight settling was observed at the 5 day and 7 day time points. Mild settling was observed at the 14 day time point. Mild settling is defined as in terms of a gradient from bottom to top, in that the appearance of the emulsion appears more opaque toward the top of the emulsion with no distinct phase separation. Settling is an acceptable observation for any emulsion. There was no phase separation at any time point for any of the samples.

The pH of both NE vaccines was neutral at all time points, with all values being 7.0 to 7.1. The mean particle size range was 426 to 445 nm. The zeta potential reading ranged from −2.3 to 3.6, with an average of 0.4.

The results are summarized in Tables 27-31, below.

TABLE 27

Time = 0

| | Storage | Settling | Separation | pH | Particle Size (nm) | Zeta Potential (mV) |
|---|---|---|---|---|---|---|
| 20% W805EC-60 μg Fluzone/mL | initial | no | no | 6.99 | 429.1 | 0.09 |
| 20% W805EC-30 μg Fluzone/mL in PBS | initial | no | no | 7.06 | 428.0 | 1.44 |

TABLE 28

Measurements Day Two

| | Storage | Settling | Separation | pH | Particle Size (nm) | Zeta Potential (mV) |
|---|---|---|---|---|---|---|
| 20% W805EC- | 5 C. | no | no | 7.07 | 444.8 | −0.11 |
| 60 μg Fluzone/mL | 22 C. | no | no | n/a | n/a | n/a |
| 20% W805EC- | 5 C. | no | no | 7.08 | 428.9 | 1.68 |
| 30 μg Fluzone/mL in PBS | 22 C. | no | no | n/a | n/a | n/a |

TABLE 29

Measurements Day Five

| | Storage | Settling | Separation | pH | Particle Size (nm) | Zeta Potential (mV) |
|---|---|---|---|---|---|---|
| 20% W805EC- | 5 C. | slight | no | 7.07 | 432.4 | 1.56 |
| 60 μg Fluzone/mL | 22 C. | slight | no | n/a | n/a | n/a |
| 20% W805EC- | 5 C. | slight | no | 7.00 | 440.4 | −0.93 |
| 30 μg Fluzone/mL in PBS | 22 C. | slight | no | n/a | n/a | n/a |

TABLE 30

Measurements Week One

| | Storage | Settling | Separation | pH | Particle Size (nm) | Zeta Potential (mV) |
|---|---|---|---|---|---|---|
| 20% W805EC- | 5 C. | slight | no | 7.04 | 428.1 | −2.30 |
| 60 μg Fluzone/mL | 22 C. | slight | no | 7.07 | 430.1 | −0.003 |
| 20% W805EC- | 5 C. | slight | no | 7.07 | 427.2 | 0.0003 |
| 30 μg Fluzone/mL in PBS | 22 C. | slight | no | 7.00 | 430.9 | −1.40 |

TABLE 31

Measurements at Week Two

| | Storage | Settling | Separation | pH | Particle Size (nm) | Zeta Potential (mV) |
|---|---|---|---|---|---|---|
| 20% W805EC- 60 µg Fluzone/mL | 5 C. | mild | no | 7.06 | 427.7 | 0.98 |
| | 22 C. | mild | no | 7.05 | 433.5 | 0.38 |
| 20% W805EC- 30 µg Fluzone/mL in PBS | 5 C. | mild | no | 7.07 | 425.5 | 3.61 |
| | 22 C. | mild | no | 7.06 | 437.9 | −0.09 |

Example 14

Stability

The purpose of this example was to evaluate the potency of Fluzone® influenza vaccine mixed with a nanoemulsion vaccine adjuvant according to the invention.

The nanoemulsion vaccine adjuvant used in this example was $W_{80}$% 5EC, described above. $W_{80}$% 5EC at 5% and at 20% were mixed with Fluzone® influenza vaccine (sanofi pasteur, 2008-2009) and the potency of the adjuvanted Fluzone® influenza vaccines was compared to the potency of Fluzone® influenza vaccine alone. The Fluzone® influenza vaccine (2008-2009) had a concentration of 30 µg/mL HA antigen/viral strain. The testing was accomplished by determining the haemagglutinin (HA) concentration of Fluzone® influenza vaccine for each strain of influenza virus contained in the vaccine, namely A/Brisbane/59/2007, A/Uruguay/716/2007, and B/Florida/4/2006. This was because the major antigenic determinant of Influenza A and B virus is haemagglutinin (HA).

The stability of both adjuvanted Fluzone® influenza vaccines was also examined after 8, 24, and 48 hours.

The single radial immunodiffusion (SRID) technology was first described by Schild et al. for the assay of influenza HA antigen (Schild et al., "A Single Radial Immunodiffusion Technique for the Assay of Influenza Haemagglutinin Antigen: Proposals for an Assay Method for the Haemagglutinin Content of Influenza Vaccines," *Bull. WHO*, 52:223-231 (1975)). The assay is based on the diffusion of disrupted whole virus or viral antigens into agarose gel containing specific anti-HA serum. The interaction between antigen and antibody produces a zone of precipitation whose size is directly proportional to the amount of antigen applied. The assay has proved to be an accurate and reproducible method for potency assays of inactivated whole virus and subunit influenza vaccines (Wood et al., "An Improved Single Radial Immunodiffusion Technique for the Assay of Influenza Haemagglutinin Antigen; Application for Potency Determinators of Inactivated Whole Virus and Subunit Vaccines," *J. Biol. Stand.*, 5:237-247 (1977)).

Materials

The reference antigens used in this experiment were as follows: (1) A/Brisbane/59/2007 (H1N1), 83 µg/mL HA antigen; (2) A/Uruguay/716/2007 (also known as A/Brisbane/10/2007-like) (H3N2), 46 µg/mL HA antigen; and (3) B/Florida/4/2006, 45 µg/mL HA antigen. All antigens were obtained from the National Institute for Biological Standards and Control (NIBSC).

Methods

The two Fluzone® nanoemulsion adjuvanted vaccines used in the example are 5% $W_{80}$% 5EC nanoemulsion +20 µg/mL HA and 20% $W_{80}$% 5EC nanoemulsion +20 µg/mL HA The samples were prepared at the same time for consistency and assayed on the plates after 0, 8, 24, and 48 hours. The samples were stored in glass vials at 4° C. for each of the time points. Each Fluzone nanoemulsion adjuvanted vaccine preparation were treated with Zwittergent 3-14 detergent for 30 min. (i.e., 1000 µL test article and 110 µL 10% w/v zwittergent) and diluted to 15 µg/mL, 10 µg/mL, and 7.5 µg/mL with PGS as shown in Table 32.

TABLE 32

Dilution of Fluzone nanoemulsion adjuvanted vaccines

| | | Volume (µL) | |
|---|---|---|---|
| Sample | Concentration (µg/mL) | Detergent Treated Sample | PBS |
| Antigens | 20 | 460 | 0 |
| | 15 | 300 | 100 |
| | 10 | 200 | 200 |
| | 7.5 | 150 | 250 |

The Fluzone® vaccine was diluted in PBS to adjust its concentration to 20 µg/mL HA Ag/strain. Only one control article was needed for both formulations since their HA content was the same. See Table 33.

TABLE 33

Fluzone ® Vaccine Control

| Name | Total Volume (mL) | Fluzone ® (mL) | PBS (mL) |
|---|---|---|---|
| 20 µg/mL HA | 8 | 5.333 | 2.667 |

The diluted Fluzone® vaccine was treated with zwittergent 3-14 detergent (i.e., 1000 µL vaccine and 110 µL 10% w/v zwittergent) and diluted to 15 µg/mL, 10 µg/mL, and 7.5 µg/mL with PBS.

The reference antigens were reconstituted in distilled water at 20 µg HA/mL as described in Table 34.

TABLE 34

Reconstitution of the Reference Antigens

| Antigen | Quantity of HA antigen (µg) | Volume of Water (mL) |
|---|---|---|
| A/Brisbane/59/2007 (H1N1) | 83 | 4.15 |
| A/Uruguay/716/2007 (H3N2) | 46 | 2.3 |
| B/Florida/4/2006 | 45 | 2.225 |

The reference antigens were treated with zwittergent 3-14 detergent (i.e., 1000 µL test article and 110 µL 10% w/v zwittergent) and diluted to 15 µg/mL, 10 µg/mL, and 7.5 µg/mL in PBS.

Antisera were also obtained from NIBSC: (1) Influenza anti-A/Brisbane/59/2007 (IVR148) (H1N1) HA; (2) Influenza anti-A/Brisbane/10/2007-like HA (referred to as anti-A/Uruguay/716/2007 HA) (H3N2); and (3) Influenza anti-B/Florida/4/2006 HA.

The antisera from the antigens present in the vaccine were used to confirm the level of antigen present in the vaccine. The antisera were added to the agarose gel before plating in the volumes shown in Table 35.

TABLE 35

Preparation of Immunogels

| Antisera | Volume of Antisera (μL) | Volume of agarose gel (mL) |
|---|---|---|
| A/Brisbane/59/2007 | 182 | 13 |
| A/Uruguay/716/2007 | 156 | 13 |
| B/Florida/4/2006 | 182 | 13 |

20 μL of each reference antigen, control article, and test formulation dilutions were added into corresponding wells in duplicate. Reference antigens were inoculated in wells 1-4 and 5-8 from concentration 20 μg/mL to 7.5 μg/mL.

Results

Appearance: Both solutions of Fluzone®+5% nanoemulsion vaccine adjuvant and Fluzone®+20% nanoemulsion vaccine adjuvant were assessed for their appearance at each time point. No separation was observed for the formulations, and all stages of creaming, settling, and separation were acceptable and indicated that the formulations were stable.

Potency: Each antigen, control article, and test formulation was inoculated in duplicate on each plate and six plates were inoculated per antiserum (A/Brisbane/59/2007, A/Uruguay/716/2007, and B/Florida/4/2006), for a total of 18 plates per antiserum at each time point. On staining day, all the plates were stained. Diameters of the rings were measured across the longest axis and at a 90° angle thus generating two diameters per ring. The geometric mean (d) was then calculated and the square ($d^2$) of this value was plotted versus the antigen concentration if $d^2$ was in the range of 30-100 for all dilutions. The coefficient of determination ($r^2$) was determined from the regression line equation and the assay was validated when $r^2 \geq 0.95$. The slope ratio, common intercept (CI), and potency value (in μg/mL) were calculated. Potency values (μg/mL) were determined for each of the following at 0 hours, 8 hours, 24 hours, and at 48 hours (data not shown): (1) Fluzone® vs. A/Brisbane/59/2007; (2) Fluzone® vs. A/Uruguay/716/2007; (3) Fluzone® vs. B/Florida/4/2006; (4) Fluzone®+5% nanoemulsion vaccine vs. A/Brisbane/59/2007; (5) Fluzone®+5% nanoemulsion vaccine vs. A/Uruguay/716/2007; (6) Fluzone®+5% nanoemulsion vaccine vs. B/Florida/4/2006; (7) Fluzone®+20% nanoemulsion vaccine vs. A/Brisbane/59/2007; (8) Fluzone®+20% nanoemulsion vaccine vs. A/Uruguay/716/2007; and (9) Fluzone®+20% nanoemulsion vaccine vs. B/Florida/4/2006. A summary of the results is shown in Table 36.

TABLE 36

Summary of Potency Values in μg/mL Obtained for Each Formulation

| Antiserum | Formulation | 0 hours | 8 hours | 24 hours | 48 hours |
|---|---|---|---|---|---|
| A/Brisbane/59/2007 (H1N1) | Fluzone ® | 20 | 22 | 20 | 22 |
| | Fluzone ® + 5% NE | 19 | 21 | 20 | 18 |
| | Fluzone ® + 20% NE | 17 | 17 | 19 | 16 |
| A/Uruguay/716/2007 (H3N2) | Fluzone ® | 24 | 26 | 23 | 24 |
| | Fluzone ® + 5% NE | 20 | 24 | 21 | 21 |
| | Fluzone ® + 20% NE | 18 | 15 | 17 | 16 |
| B/Florida/4/2006 | Fluzone ® | 18 | 22 | 22 | 19 |
| | Fluzone ® + 5% NE | 17 | 18 | 15 | 17 |
| | Fluzone ® + 20% NE | 13 | 16 | 16 | 18 |

As shown in the data above, overall the potency values for A/Brisbane/59/2007, A/Uruguay/716/2007, and B/Florida/4/2006 were found to be stable over 48 hours in the presence or absence of the nanoemulsion vaccine adjuvant. It was also shown that the nanoemulsion vaccine adjuvant has a minimal effect on the concentration of HA antigen for each virus strain as compared to the non-adjuvanted Fluzone® influenza vaccine. Nanoemulsion adjuvanted vaccines were visually stable for up to 48 hours (not tested past 48 hours).

It will be apparent to those skilled in the art that various modifications and variations can be made in the methods and compositions of the present invention without departing from the spirit or scope of the invention. Thus, it is intended that the present invention cover the modifications and variations of this invention provided they come within the scope of the appended claims and their equivalents.

What is claimed is:

1. A method for inducing an immune response to influenza in a subject comprising intranasally administering to a subject a nanoemulsion vaccine, wherein the nanoemulsion vaccine comprises:
   (a) a nanoemulsion comprising:
      (i) droplets having an average diameter of less than about 1000 nm;
      (ii) an aqueous phase;
      (iii) about 1% to about 80% (v/v) soybean oil;
      (iv) about 0.001% to about 10% (v/v) of at least one surfactant, wherein the surfactant is Polysorbate 80, Polysorbate 20, or a combination thereof;
      (v) about 0.01% to about 50% (v/v) of at least one organic solvent, wherein the organic solvent is an alcohol; and
      (vi) less than about 5% (v/v) cetylpyridinium chloride (CPC); and
   (b) one or more influenza immunogens or recombinant influenza proteins from an influenza strain, or an immunogenic fragment thereof, selected from the group consisting of:
      (1) an influenza A virus strain, or an immunogenic fragment of an influenza A virus strain;
      (2) an influenza B virus strain or an immunogenic fragment of an influenza B virus strain;
      (3) an influenza C virus strain or an immunogenic fragment of an influenza C virus strain;
      (4) A/New Caledonia/20/99 lineage;
      (5) A/Fujian/411/2002 lineage;
      (6) A/Kumamoto/102/2002 lineage;
      (7) A/Wyoming/3/2003 lineage;
      (8) A/Wellington/1/2004 lineage;
      (9) A/California/7/2004 lineage;
      (10) A/New York/55/2004 lineage;
      (11) A/Solomon Islands/3/2006 lineage;
      (12) A/Wisconsin/67/2005 lineage;
      (13) A/Hiroshima/52/2005 lineage;
      (14) A/Brisbane/10/2007 lineage;
      (15) B/Hong Kong/330/2001 lineage;
      (16) B/Shandong/7/97 lineage;
      (17) B/Hong Kong/1434/2002 lineage;
      (18) B/Brisbane/32/2002 lineage;
      (19) B/Shanghai/361/2002 lineage;
      (20) B/Jiangsu/10/2003 lineage;
      (21) B/Jilin/20/2003 lineage;
      (22) B/Malaysia/2506/2004 lineage;
      (23) B/Florida/4/2006 lineage,
      (24) B/Nictoria/2/87 lineage,
      (25) B/Yamagata/16/88 lineage,
      (26) C/Aichi/1/99 lineage,
      (27) C/Sao Paulo/378/82 lineage,
      (28) C/Yamagata/26/81 lineage,

(29) C/Aichi/1/81 lineage,
(30) C/Aomori/74 lineage,
(31) C/Mississippi/80 lineage, and
(32) any combination thereof,
wherein the total amount of influenza immunogen and/or influenza protein is present at about 0.9 µg up to about 22.5 µg, per dose;
wherein the nanomulsion does not comprise Triton X-100;
wherein the subject produces a protective immune response after a single administration of the nanoemulsion vaccine; and
wherein administration of the nanoemulsion vaccine to a subject results in an equal or greater immune response as compared to that generated by administration of an influenza vaccine comprising the same influenza immunogen and/or recombinant influenza protein in the absence of the nanoemulsion vaccine.

2. The method of claim 1, wherein the nanoemulsion is administered sequentially with the influenza immunogen and/or recombinant influenza proteins, or via any suitable pharmaceutical route.

3. The method of claim 1, wherein the recombinant influenza protein is an influenza antigen.

4. The method of claim 3, wherein the recombinant influenza protein is recombinant H5 influenza antigen.

5. The method of claim 1, wherein the influenza immunogen or influenza protein is from an influenza strain selected from the group consisting of influenza H3N2 Strain A/Wisconsin (H3N2), A/Solomon Islands (H1N1), B/Malaysia, A/Brisbane, A/Uruguay, B/Florida, A/Indonesia, and any combination thereof.

6. A method for inducing an immune response to influenza in a subject comprising intranasally administering to a subject (i) a nanoemulsion, and (ii) one or more influenza vaccines, wherein the nanoemulsion comprises:
(a) droplets having an average diameter of less than about 1000 nm;
(b) an aqueous phase;
(c) about 1% to about 80% (v/v) soybean oil;
(d) about 0.001% to about 10% (v/v) of at least one surfactant, wherein the surfactant is Polysorbate 80, Polysorbate 20, or a combination thereof;
(e) about 0.1% to about 50% (v/v) of at least one organic solvent, wherein the organic solvent is an alcohol; and
(f) less than about 5% (v/v) cetylpyridinium chloride (CPC);
wherein the one or more influenza vaccines are combined with the nanoemulsion, or the nanoemulsion is sequentially administered with one or more influenza vaccines;
wherein the subject produces a protective immune response after a single administration of the nanoemulsion vaccine; and
wherein administration of the nanoemulsion and one or more influenza vaccines to a subject results in a greater immune response as compared to that generated by administration of the one or more influenza vaccines in the absence of the nanoemulsion; and
wherein the nanomulsion does not comprise Triton X-100.

7. The method of claim 1, wherein the nanoemulsion vaccine is formulated into a dosage form selected from the group consisting of a liquid dispersion, gel, aerosol, nasal aerosol, ointment, cream, semi-solid dose forms, and suspensions.

8. The method of claim 1, wherein the nanoemulsion vaccine is a controlled release formulation, sustained release formulation, immediate release formulation, or any combination thereof.

9. The method of claim 1, wherein the nanoemulsion vaccine is formulated into a transdermal delivery system such as a patch or administered by a pressurized or pneumatic device.

* * * * *